US012790350B2

(12) United States Patent
Brom et al.

(10) Patent No.: US 12,790,350 B2
(45) Date of Patent: Nov. 10, 2026

(54) THIAZOLOPYRIMIDINONE DERIVATIVES

(71) Applicant: Hoffmann-La Roche Inc., Little Falls, NJ (US)

(72) Inventors: Virginie Brom, Blotzheim (FR); Cosimo Dolente, Allschwil (CH); Delphine Gaufreteau, Kembs (FR); Nadine Grether, Moehlin (CH); Fionn Susannah O'Hara, Basel (CH); Matilde Piras, Basel (CH); Hasane Ratni, Habsheim (FR); Michael Reutlinger, Freiburg (DE); Walter Vifian, Sissach (CH); Claudio Zambaldo, Basel (CH)

(73) Assignee: Hoffmann-La Roche Inc., Branchburg, NJ (US)

( * ) Notice: Subject to any disclaimer, the term of this patent is extended or adjusted under 35 U.S.C. 154(b) by 317 days.

(21) Appl. No.: 18/468,378

(22) Filed: Sep. 15, 2023

(65) Prior Publication Data

US 2024/0018163 A1 Jan. 18, 2024

Related U.S. Application Data

(63) Continuation of application No. PCT/EP2022/056586, filed on Mar. 15, 2022.

(30) Foreign Application Priority Data

Mar. 17, 2021 (EP) .................................... 21163259

(51) Int. Cl.
*C07D 519/00* (2006.01)
*C07D 513/04* (2006.01)

(52) U.S. Cl.
CPC ......... *C07D 519/00* (2013.01); *C07D 513/04* (2013.01)

(58) Field of Classification Search
CPC ........................... C07D 513/04; C07D 519/00
See application file for complete search history.

(56) References Cited

U.S. PATENT DOCUMENTS

2020/0165256 A1 5/2020 Woll et al.

FOREIGN PATENT DOCUMENTS

| | | | |
|---|---|---|---|
| WO | 1993/16050 | A1 | 8/1993 |
| WO | 1994/00458 | A1 | 1/1994 |
| WO | 2021/207550 | A1 | 10/2002 |
| WO | 2013/057253 | A1 | 4/2013 |
| WO | 2013/119916 | A2 | 8/2013 |
| WO | 2015/048245 | A1 | 4/2015 |
| WO | 2015/173181 | A1 | 11/2015 |
| WO | 2017/081111 | A1 | 5/2017 |
| WO | 2019/005980 | A1 | 1/2019 |
| WO | 2019/005993 | A1 | 1/2019 |
| WO | 2019/057740 | A1 | 3/2019 |
| WO | 2020/005873 | A1 | 1/2020 |
| WO | 2020/005877 | A1 | 1/2020 |
| WO | 2020/005882 | A1 | 1/2020 |
| WO | 2021/207530 | A1 | 10/2021 |
| WO | 2022/194800 | A1 | 9/2022 |
| WO | 2022/194802 | A1 | 9/2022 |
| WO | 2023/064879 | A1 | 4/2023 |
| WO | 2023/170115 | A1 | 9/2023 |
| WO | 2023/225244 | A1 | 11/2023 |
| WO | 2024/218207 | A1 | 10/2024 |
| WO | 2025/111408 | A1 | 5/2025 |
| WO | 2026/087399 | A1 | 4/2026 |

OTHER PUBLICATIONS

"International Preliminary Report on Patentability—PCT/EP2022/056585" (Report Issuance Date: Sep. 12, 2023; Chapter I), :pp. 1-8 (Sep. 28, 2023).
"International Preliminary Report on Patentability—PCT/EP2022/056587" (Report Issuance Date: Sep. 12, 2023; Chapter I), :pp. 1-8 (Sep. 28, 2023).
International Preliminary Report on Patentability—PCT/EP2022/056586, (Report Issuance Date: Sep. 12, 2023; Chapter I),:pp. 1-8 (Sep. 28, 2023).
"International Search Report—PCT/EP2022/056585" (w/Written Opinion), :pp. 1-12 (Jun. 24, 2022).
"International Search Report—PCT/EP2022/056587" (w/Written Opinion), :pp. 1-14 (May 27, 2022).
"International Search Report—PCT/EP2022/056586" (w/Written Opinion), :pp. 1-12 (May 25, 2022).

(Continued)

*Primary Examiner* — Laura L Stockton

(74) *Attorney, Agent, or Firm* — Robert C. Hall; Genentech, Inc.

(57) ABSTRACT

The invention relates to a compound of formula (I)

(I)

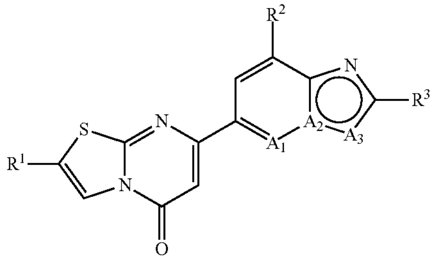

wherein $R^1$-$R^4$ and $A_1$-$A_3$ are as defined in the description and in the claims. The compound of formula (I) can be used as a medicament.

22 Claims, No Drawings

(56) References Cited

OTHER PUBLICATIONS

Lee, J., et al., "Huntington's disease onset is determined by length of uninterrupted CAG, not encoded poly glutamine, and is modified by DNA maintenance mechanisms" BIORXIV—Cold Spring Harbor Lab 529768:1-72 (Jan. 24, 2019).
Tabrizi, S., et al., "Huntingtin Lowering Strategies for Disease Modification in Huntington's Disease" NEURON—Cell Press 101(5):801-819 (Mar. 6, 2019).
Tabrizi, S., et al., "Potential endpoints for clinical trials in premanifest and early Huntington's disease in the TRACK-HD study: analysis of 24 month observational data" Lancet Neurol (Epub: Dec. 2, 2011), 11(01):42-53 (Jan. 1, 2012).
Wang, N., et al., "Neuronal targets for reducing mutant huntingtin expression to ameliorate disease in a mouse model of Huntington's disease" Nature Med (Epub: Apr. 28, 2014), 20(5):536-541 (May 1, 2014).
Wild, E., et al., "Therapies targeting DNA and RNA in Huntington's disease" Lancet Neurol 16(10):837-847 (Oct. 1, 2017).
Jang, M.-Y et al., "Synthesis, immunosuppressive activity and structure-activity relationship study of a new series of 4-N-piperazinyl-thieno[2,3-d]pyrimidine analogues" Bioorganic & Medicinal Chemistry Letters 20(3):844-847 (2010).
Brighty, K.E et al., "Synthesis of (1a,5a,6a)-6-Amino-3-azabicyclo[3.1.0]hexane, a Novel Achiral Diamine" SYNLETT 11:pp. 1097-1099 (Nov. 1996).
CAS Registry Database, 2726461-18-1, (7-(8-Fluoro-2-methylimidazo[1,2-a]pyridin-6-yl)-2-(4- methyl-1-piperazinyl)-5H-1,3,4-thiadiazolo[3,2-a]pyrimidin-5-one), p. Nov. 1, 07, 2021.
CAS Registry Database, 2726461-23-8, (2-(4,7-diazaspiro[2.5]oct-7-yl)-7-(8-fluoro-2- methylimidazo[1,2-a]pyridin-6-yl)-5H-1,3,4-Thiadiazolo[3,2-a]pyrimidin-5-one), p. Nov. 1, 07, 2021.
CAS Registry Database, 2726462-68-4, (7-(8-Fluoro-2-methylimidazo[1,2-a]pyridin-6-yl)-2-(1- methyl-4-piperidinyl)-5H-1,3,4-thiadiazolo[3,2-a]pyrimidin-5-one), p. Nov. 1, 07, 2021.
CAS Registry Database, 2726462-72-0, (7-(8-Fluoro-2-methylimidazo[1,2-a]pyridin-6-yl)-2-(4- piperidinyl)-5H-1,3,4-thiadiazolo[3,2-a]pyrimidin-5-one), p. Nov. 1, 07, 2021.
CAS Registry Database, 2726462-78-6, (7-(8-Fluoro-2-methylimidazo[1,2-a]pyridin-6-yl)-2-(1- piperazinyl)-5H-1,3,4-thiadiazolo[3,2-a]pyrimidin-5-one), p. Nov. 1, 07, 2021.
CAS Registry Database, 2839514-70-2, (7-(8-Fluoro-2-methylimidazo[1,2-b]pyridazin-6-yl)-2-(4- piperidinyl)-5H-1,3,4-thiadiazolo[3,2-a]pyrimidin-5-one), p. Oct. 1, 13, 2022.
CAS Registry Database, 2923320-28-7, (7-(8-fluoro-2-methylimidazo[1,2-a]pyridin-6-yl)-2-(2,2,6,6- tetramethyl-4-piperidinyl)-5H-1,3,4-Thiadiazolo[3,2-a]pyrimidin-5-one), p. May 1, 11, 2023.
Frances et al., "Developing Splice Modifier Therapies at Roche: Learnings and Challenges" European Federation for Medicinal Chemistry - 10th International Symposium on Advances in Synthetic and Medicinal Chemistry:p. 1 (Sep. 1, 2025).
International Preliminary Report on Patentability --- PCT/EP2023/055838 issued Sep. 10, 2024, pp. 1-9.
"International Preliminary Report on Patentability -- PCT/EP2024/060533":pp. 1-7 (Oct. 16, 2025).
"International Search Report -- PCT/EP2025/080143" (w/Written Opinion),:pp. 1-12 (Dec 4, 2025).
"International Search Report -- PCT/EP2024/060533" (w/Written Opinion),:pp. 1-10 (Jul. 5, 2024).
International Search Report with Written Opinion --- PCT/EP2023/055838 mailed Apr. 26, 2023, pp. 1-15.
Katritzky, A.R et al., "The preparation and fungicidal activity of a series of thiazolyl- and isothiazolyl-diarylcarbinols" Can. J. Chem. 66(7):pp. 1617-1628 (Jul. 1988) https://doi.org/10.1139/v88-262.
Sanchez et al., "Huntington's Disease: Mechanisms of Pathogenesis and Therapeutic Strategies" Cold Spring Harbor Perspectives in Medicine 7:pp. 1-22 ( 2017) DOI: 10.1101/cshperspect.a024240.

THIAZOLOPYRIMIDINONE DERIVATIVES

This application is a Continuation of International Application No. PCT/EP2022/056586, filed on Mar. 15, 2022, which claims benefit of European Patent Application No. 21163259.1, filed on Mar. 17, 2021.

The present invention relates to new organic compounds useful for therapy and/or prophylaxis in a mammal, and in particular to compounds that reduce the protein level of huntingtin (HTT) and which are useful in the treatment of Huntington's disease.

In particular, the present invention relates to a compound of formula (I)

(I)

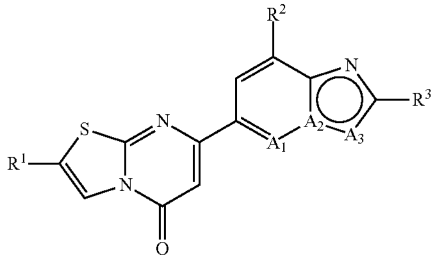

wherein $R^1$ is hydrogen, alkyl, cycloalkyl, aryl, heteroaryl or heterocycloalkyl, wherein each instance of cycloalkyl, aryl, heteroaryl and heterocycloalkyl is optionally substituted with one, two, three or four substituents independently selected from $R^4$;

$R^2$ is hydrogen, cycloalkyl, alkenyl, cyano, amino, hydroxy, halogen, alkyl, haloalkyl, haloalkoxy or alkoxy;

$R^3$ is alkyl, hydrogen, halogen or haloalkyl;

$R^4$ is halogen, alkyl, heterocycloalkyl, heterocycloalkylalkyl, alkylheterocycloalkyl, haloheterocycloalkyl, cycloalkyl, cycloalkylalkyl, alkylcycloalkyl, halocycloalkyl, cycloalkylamino, aryl, arylalkyl, alkylaryl, haloaryl, cyano, hydroxy, oxo, haloalkyl, alkylcarbonyl, alkoxy, haloalkoxy, alkoxyalkyl, alkoxycarbonyl, amino, alkylamino, dialkylamino, aminoalkyl, alkylaminoalkyl, dialkylaminoalkyl, aminoalkylamino, alkoxyalkylamino, alkylcarbonylamino, alkoxycarbonylamino, hydroxyalkyl, hydroxyalkoxyalkyl or hydroxyalkylamino; and (i) $A_1$ is —N—, $A^2$ is —N— and $A_3$ is —CH—;

(ii) $A_1$ is —N—, $A_2$ is —C— and $A_3$ is —O—; or (iii) $A_1$ is —CH—, $A_2$ is —C— and $A_3$ is —O—;

or a pharmaceutically acceptable salt thereof, provided that 2-(4,7-diazaspiro[2.5]octan-7-yl)-7-(2,8-dimethylimidazo[1,2-b]pyridazin-6-yl)thiazolo[3,2-a]pyrimidin-5-one;

is excluded.

Huntington's Disease (HD) is an inherited autosomal dominant neurodegenerative disease caused due to a CAG bases repeat expansion in the huntingtin (HTT) gene. Several lines of evidence indicate that the mutant HTT gene together with its gene product mHTT protein contributes to HD pathogenesis via a toxic gain of function mechanism.

The triplet repeat expansion in the exon 1 of the HTT gene translates into a polyglutamine repeat in the HTT protein which is prone to misfolding and aggregating in the cells. While the exact mechanisms of how mutant HTT disrupts cellular function is unclear, several processes ranging from interruption of RNA translation, toxic RNA species, protein aggregates, RNA translation, and stress granules have been implicated.

At a neural circuit level, HD has been shown to affects deep brains structures like the striatum as well as cortical regions to different extents. Seminal mouse genetic experiments coupled with human imaging experiments point to a key role of cortico-striatal connections in the pathogenicity of HD (Wang et al., "Neuronal targets of mutant huntingtin genetic reduction to ameliorate Huntington's disease pathogenesis in mice" Nature medicine 20.5 (2014): 536; Tabrizi et al.; "Potential endpoints for clinical trials in premanifest and early Huntington's disease in the TRACK-HD study: analysis of 24 month observational data." The Lancet Neurology 11.1 (2012): 42-53).

HD typically manifests around 30-50 years of age characterized by a multitude of symptoms spanning the motor, cognitive and affective domains eventually leading to death in 10-20 years after the onset of motor symptoms. CAG repeat length negatively correlates with age of onset of motor symptoms, however this only accounts for 50-70% of the variance in age of onset. In an effort to identify genetic modifiers of age of onset in HD, Lee et al. (2019, Huntington's disease onset is determined by length of uninterrupted CAG, not encoded polyglutamine, and is modified by DNA maintenance mechanisms. Bioarxiv doi: doi.org/10.1101/529768) conducted a large GWAS (genome-wide association study) that has uncovered additional genetic modifiers of age of onset.

Various mouse models have been characterized to model aspects of HD. The YAC128 mice expressing the full length mutant HTT transgene with 128 CAG repeats, BACHD mice expressing the full length mutant HTT genomic sequence with 97 CAG/CAA repeats, the R6/2 mice expressing exon 1 of the mutant human HTT gene with 110-135 CAG repeats). In addition to these mice that express the human transgene, there are also a series of mouse models, like the frequently used Q111, the Q175 knock in mice where the expanded repeats are knocked-in in the context of the mouse HTT locus.

There are currently no disease modifying therapies for Huntington's Disease while several are in development. The core disease process behind the symptomatology characterized by motor, cognitive and behavioral symptoms remains unmet by the various symptomatic treatments currently approved. Tetrabenazine and tiapride are currently approved for the treatment of motor symptoms namely HD-associated chorea. In addition, anticonvulsants, benzodiazepines, antidepressants, and antipsychotics are also used off-label to treat the motor, cognitive and psychiatric symptoms associated with HD.

Several therapeutic strategies targeting DNA and RNA are being investigated for HTT lowering (E. J. Wild, S. Tabrizi, Lancet Neurol. 2017 16(10): 837-847). HTT lowering is a promising therapeutic approach that aims to slow disease progression by getting at the core cause of Huntington's Disease. HTT lowering is thought to be transformative when treated in the pre-manifest or manifest stages of disease onset, thus preventing major neurodegenerative processes in the brain. However, the challenge lies in identifying the patients at the right disease stage, as age of onset is quite variable across the population (S. J. Tabrizi, R. Ghosh, B. R. Leavitt, Neuron, 2019, 102(4), 899).

The current clinical approaches are mainly based on antisense oligonucleotides (ASOs). In addition, a few allele specific lowering strategies such as SNP (single-nucleotide polymorphism) based ASO and zinc finger based gene editing approaches are investigated. While the use of small molecules to lower HTT expression has been postulated, this strategy has not yet been validated and none has proved successful so far.

Small molecules provide an opportunity to allow for HTT lowering in the brain as well as the periphery. In addition, a small molecule modality allows access to patient populations that could be difficult to reach with modalities like ASOs or gene therapy.

There is thus the need for new compounds capable of lowering mHTT and with favourable brain penetration properties.

The applicant has surprisingly found that the compounds of the invention are active in lowering mHTT and are therefore useful in the treatment of HD.

All publications, patent applications, patents, and other references mentioned herein are incorporated by reference in their entirety.

In the present description the term “alkyl”, alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert.-butyl, the isomeric pentyls, the isomeric hexyls, the isomeric heptyls and the isomeric octyls. Particular examples of “alkyl” are methyl, ethyl and isopropyl. Methyl and ethyl are particular examples of “alkyl” in the compound of formula (I).

In the present description the term “alkenyl”, alone or in combination, signifies a straight-chain or branched-chain alkenyl group with 2 to 8 carbon atoms and further comprising at least one double bond, particularly a straight or branched-chain alkenyl group with 2 to 4 carbon atoms and further comprising at least one double bond. Particular examples of “alkenyl” are ethenyl, propenyl, isopropenyl, butenyl, isobutenyl and tertbutenyl. Isopropenyl is a particular example of “alkenyl” in the compound of formula (I).

The term “cycloalkyl”, alone or in combination, signifies a cycloalkyl ring with 3 to 10 carbon atoms and particularly a cycloalkyl ring with 3 to 6 carbon atoms. Examples of “cycloalkyl” are cyclopropyl, cyclobutyl, cyclopentyl and cyclohexyl, cycloheptyl, cyclooctyl, cyclononyl and cyclodecyl. A particular example of “cycloalkyl” is cyclopropyl.

The term “aryl”, alone or in combination, signifies an aromatic mono- or bicyclic ring system comprising 6 to 10 carbon ring atoms. Examples of “aryl” include, but are not limited to, phenyl and naphthyl.

The term “heteroaryl”, alone or in combination, signifies an aromatic mono- or bicyclic ring system with 5 to 12 ring atoms, comprising 1, 2, 3 or 4 heteroatoms each independently selected from N, O and S, the remaining ring atoms being carbon. Examples of heteroaryl include, but are not limited to, furanyl, thiophenyl, 1H-pyrazolyl, 1H-imidazolyl, 1H-1,2,3-triazolyl, 4H-1,2,4-triazolyl, 1,2,4-oxadiazolyl, 1,3,4-oxadiazolyl, pyridinyl, pyridazinyl, pyrimidinyl, pyrazinyl, 1H-indolyl, 2H-indolyl, 1H-indazolyl, 2H-indazolyl, indolizinyl, benzofuranyl, 1H-benzimidazolyl, 1,3-benzoxazolyl, furo[2,3-b]pyridinyl, furo[2,3-c]pyridinyl, furo[3,2-b]pyridinyl, furo[3,2-c]pyridinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, 1H-pyrazolo[4,3-b]pyridinyl, 2H-pyrazolo[4,3-b]pyridinyl, 2H-pyrazolo[4,3-c]pyridinyl, pyrazolo[1,5-a]pyrazinyl, pyrazolo[1,5-a]pyrimidinyl, imidazo[1,2-a]pyridinyl, imidazo[1,2-a]pyrimidinyl, imidazo[1,2-a]pyrazinyl, imidazo[1,2-b]pyridazinyl, imidazo[1,2-c]pyrimidinyl, imidazo[1,5-a]pyridinyl, imidazo[2,1-b][1,3]thiazolyl, imidazo[2,1-b][1,3,4]thiadiazolyl, [1,3]oxazolo[4,5-b]pyridinyl, [1,2,4]triazolo[1,5-a]pyridinyl, [1,2,4]triazolo[1,5-b]pyridazinyl, benzo[d]oxazolyl and quinolinyl.

The term “alkoxy” or “alkyloxy”, alone or in combination, signifies a group of the formula alkyl-O— in which the term “alkyl” has the previously given significance, such as methoxy, ethoxy, n-propoxy, isopropoxy, n-butoxy, isobutoxy, sec-butoxy and tert.-butoxy. A particular example of “alkoxy” is methoxy.

The term “oxy”, alone or in combination, signifies the —O— group.

The terms “halogen” or “halo”, alone or in combination, signifies fluorine, chlorine, bromine or iodine and particularly fluorine, chlorine or bromine. One preferred example of halogen is fluorine. The term “halo”, in combination with another group, if not otherwise specified, denotes the substitution of said group with at least one halogen, particularly substituted with one to five halogens, particularly one to four halogens, i.e. one, two, three or four halogens.

The term “haloalkyl”, alone or in combination, denotes an alkyl group substituted with at least one halogen, particularly substituted with one to five halogens, particularly one to three halogens. Particular “haloalkyl” are fluoromethyl, trifluoromethyl, difluoromethyl, fluoroethyl, fluoropropyl and fluorobutyl. Further particular “haloalkyl” are difluoromethyl and trifluoromethyl.

The term “haloalkoxy”, alone or in combination, denotes an alkoxy group substituted with at least one halogen, particularly substituted with one to five halogens, particularly one to three halogens. Particular “haloalkoxy” are fluoromethoxy, fluoroethoxy, difluoromethoxy, difluoroethoxy, trifluoromethoxy and trifluoroethoxy. A further particular “haloalkoxy” is difluoromethoxy.

The terms “hydroxyl” and “hydroxy”, alone or in combination, signify the —OH group.

The term “carbonyl”, alone or in combination, signifies the —C(O)— group.

The term “amino”, alone or in combination, signifies the primary amino group (—$NH_2$), the secondary amino group (—NH—), or the tertiary amino group (—N—).

The term “cyano”, alone or in combination, signifies the —CN group.

The term “heterocycloalkyl”, alone or in combination, signifies a monocyclic or bicyclic saturated or monounsaturated ring system with 3 to 12 ring atoms, comprising 1, 2, 3 or 4 heteroatoms each independently selected from N, O and S, and the remaining ring atoms being carbon. In some particular embodiments the term “heterocycloalkyl”, alone or in combination, can signify a monocyclic or bicyclic saturated or monounsaturated ring system with 5 to 10 ring atoms, comprising 1 or 2 nitrogen atoms and the remaining ring atoms being carbon. Examples of “heterocycloalkyl” are piperazinyl, azetidinyl, morpholinyl, tetrahydropyranyl, tetrahydrofuranyl, 1,2,3,6-tetrahydropyridin-4-yl, 4,7-diazaspiro[2.5]octan-7-yl, (8aS)-3,4,6,7,8,8a-hexahydro-1H-pyrrolo[1,2-a]pyrazin-2-yl, (8aR)-3,4,6,7,8,8a-hexahydro-1H-pyrrolo[1,2-a]pyrazin-2-yl, 3,8-diazabicyclo[3.2.1]octan-8-yl, (1S,4S)-2,5-diazabicyclo[2.2.1]heptan-2-yl, 2,3,3a,4,6,6a-hexahydro-1H-pyrrolo[3,4-c]pyrrol-5-yl, pyrrolidinyl, 2,8-diazaspiro[4.5]decan-2-yl, piperidyl, (7R)-4-azaspiro[2.5]octan-7-yl, (7S)-4-azaspiro[2.5]octan-7-yl, 4-azaspiro[2.5]octan-7-yl, [rac-(1R,5S)-9-oxa-3-azabicyclo[3.3.1]nonan-7-yl], [rac-(1S,5R)-9-oxa-3-azabicyclo[3.3.1]

nonan-7-yl, and [rac-(1S,5R)-3-azabicyclo[3.1.0]hexan-6-yl]. Particular examples of "heterocycloalkyl" are piperazin-1-yl, 4-piperidyl, pyrrolidin-1-yl, 1,2,3,6-tetrahydropyridin-4-yl, (7S)-4-azaspiro[2.5]octan-7-yl and (8aR)-3,4,6,7,8,8a-hexahydro-1H-pyrrolo[1,2-a]pyrazin-2-yl.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and trifluoroacetic acid. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts formed with trifluoroacetic acid or hydrochloric acid.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), trityl (Trt), 2,4.dimethoxybenzyl (Dmb), 9-fluorenylmethyl carbamate (Fmoc), 2-trimethylsilylethyl carbamate (Teoc), carbobenzyloxy (Cbz) and p-methoxybenzyloxycarbonyl (Moz). A particular example of a protecting group is tert-butoxycarbonyl (Boc).

A certain embodiment of the invention relates to the compound of formula (I) as described herein, or a pharmaceutically acceptable salt thereof, wherein at least one substituent comprises at least one radioisotope. Particular examples of radioisotopes are $^{2}H$, $^{3}H$, $^{13}C$, $^{14}C$ and $^{18}F$.

Furthermore, the invention includes all optical isomers, i.e. diastereoisomers, diastereomeric mixtures, racemic mixtures, all their corresponding enantiomers and/or tautomers as well as their solvates, wherever applicable, of the compound of formula (I).

The compound of formula (I) may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

The term "asymmetric carbon atom" means a carbon atom with four different substituents. According to the Cahn-Ingold-Prelog Convention an asymmetric carbon atom can be of the "R" or "S" configuration.

The invention thus also relates in particular to:

A compound according to the invention wherein $R^1$ is heterocylcoalkyl optionally substituted with one, two, three or four substituents independently selected from $R^4$;

A compound according to the invention wherein $R^1$ is heterocylcoalkyl optionally substituted with one or two substituents independently selected from $R^4$;

A compound according to the invention wherein $R^1$ is piperazin-1-yl, 1,2,3,6-tetrahydropyridin-4-yl, 4,7-diazaspiro[2.5]octan-7-yl, (8aS)-3,4,6,7,8,8a-hexahydro-1H-pyrrolo[1,2-a]pyrazin-2-yl, 3,8-diazabicyclo[3.2.1]octan-8-yl, (8aR)-3,4,6,7,8,8a-hexahydro-1H-pyrrolo[1,2-a]pyrazin-2-yl, (1S,4S)-2,5-diazabicyclo[2.2.1]heptan-2-yl, 2,3,3a,4,6,6a-hexahydro-1H-pyrrolo[3,4-c]pyrrol-5-yl, pyrrolidin-1-yl, 2,8-diazaspiro[4.5]decan-2-yl, (7R)-4-azaspiro[2.5]octan-7-yl, (7S)-4-azaspiro[2.5]octan-7-yl, 4-piperidyl, [rac-(1R,5S)-9-oxa-3-azabicyclo[3.3.1]nonan-7-yl], [rac-(1S,5R)-9-oxa-3-azabicyclo[3.3.1]nonan-7-yl or [rac-(1S,5R)-3-azabicyclo[3.1.0]hexan-6-yl], and wherein $R^1$ is optionally substituted with one or two substituents independently selected from $R^4$;

A compound according to the invention wherein $R^1$ is piperazin-1-yl, 1,2,3,6-tetrahydropyridin-4-yl, 4,7-diazaspiro[2.5]octan-7-yl, (8aS)-3,4,6,7,8,8a-hexahydro-1H-pyrrolo[1,2-a]pyrazin-2-yl, 3,8-diazabicyclo[3.2.1]octan-8-yl, (8aR)-3,4,6,7,8,8a-hexahydro-1H-pyrrolo[1,2-a]pyrazin-2-yl, (1S,4S)-2,5-diazabicyclo[2.2.1]heptan-2-yl, 2,3,3a,4,6,6a-hexahydro-1H-pyrrolo[3,4-c]pyrrol-5-yl, pyrrolidin-1-yl, 2,8-diazaspiro[4.5]decan-2-yl, (7R)-4-azaspiro[2.5]octan-7-yl, (7S)-4-azaspiro[2.5]octan-7-yl or 4-piperidyl, and wherein $R^1$ is optionally substituted with one or two substituents independently selected from $R^4$;

A compound according to the invention wherein $R^1$ is piperazin-1-yl, 4-piperidyl, pyrrolidin-1-yl, 1,2,3,6-tetrahydropyridin-4-yl, (7S)-4-azaspiro[2.5]octan-7-yl, (7R)-4-azaspiro[2.5]octan-7-yl or (8aR)-3,4,6,7,8,8a-hexahydro-1H-pyrrolo[1,2-a]pyrazin-2-yl, and wherein $R^1$ is optionally substituted with one or two substituents independently selected from $R^4$;

A compound according to the invention wherein $R^1$ is piperazin-1-yl optionally substituted with one or two substituents independently selected from $R^4$;

A compound according to the invention wherein $R^1$ is 4-piperidyl optionally substituted with one or two substituents independently selected from $R^4$;

A compound according to the invention wherein $R^1$ is (7S)-4-azaspiro[2.5]octan-7-yl optionally substituted with one or two substituents independently selected from $R^4$;

A compound according to the invention wherein $R^1$ is (7R)-4-azaspiro[2.5]octan-7-yl optionally substituted with one or two substituents independently selected from $R^4$;

A compound according to the invention wherein $R^1$ is [rac-(1R,5S)-9-oxa-3-azabicyclo[3.3.1]nonan-7-yl], [rac-(1S,5R)-9-oxa-3-azabicyclo[3.3.1]nonan-7-yl or [rac-(1S,5R)-3-azabicyclo[3.1.0]hexan-6-yl], and wherein $R^1$ is optionally substituted with one or two substituents independently selected from $R^4$;

A compound according to the invention wherein $R^1$ is cycloalkyl, aryl, heteroaryl or heterocycloalkyl, wherein each instance of cycloalkyl, aryl, heteroaryl and heterocycloalkyl is optionally substituted with one, two, three or four substituents independently selected from $R^4$;

A compound according to the invention wherein $R^1$ is hydrogen or alkyl;

A compound according to the invention wherein $R^2$ is hydrogen, cycloalkyl, alkenyl, halogen, alkyl, haloalkyl, haloalkoxy or alkoxy;

A compound according to the invention wherein $R^2$ is hydrogen, cyclopropyl, isopropenyl, fluoro, methyl, ethyl, isopropyl, trifluoromethyl, difluoromethoxy or methoxy;

A compound according to the invention wherein $R^2$ is alkyl, haloalkyl or alkoxy;

A compound according to the invention wherein $R^2$ is methyl, ethyl, trifluoromethyl or methoxy;

A compound according to the invention wherein $R^3$ is alkyl or halogen;

A compound according to the invention wherein $R^3$ is methyl or chloro;

A compound according to the invention wherein $R^4$ is halogen, alkyl or heterocycloalkyl;

A compound according to the invention wherein $R^4$ is alkyl;

A compound according to the invention wherein $R^4$ is methyl;

A compound according to the invention wherein $R^4$ is halogen;

A compound according to the invention wherein $R^4$ is fluoro, methyl or pyrrolidinyl;

A compound according to the invention wherein $R^4$ is fluoro;

A compound according to the invention wherein $A_1$ is —N—, $A^2$ is —N— and $A_3$ is —CH—;

A compound according to the invention wherein $A_1$ is —N—, $A_2$ is —C— and $A_3$ is —O—; and A compound according to the invention wherein $A_1$ is —CH—, $A_2$ is —C— and $A_3$ is —O—.

The invention further also relates in particular to:

A compound of formula (Ia) according to the invention

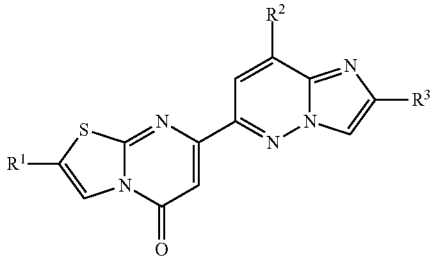

(Ia)

wherein the compound of formula (Ia) is a compound of formula (I) wherein $A_1$ is —N—, $A^2$ is —N— and $A_3$ is —CH—; and A compound of formula (Ib) according to the invention

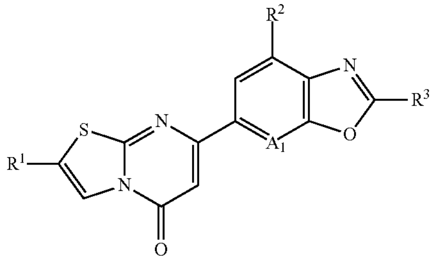

(Ib)

wherein the compound of formula (Ib) is a compound of formula (I) wherein $A_2$ is —C— and $A_3$ is —O—.

The invention further relates to a compound selected from 7-(2,8-dimethylimidazo[1,2-b]pyridazin-6-yl)-2-piperazin-1-yl-thiazolo[3,2-a]pyrimidin-5-one;

7-(2,8-dimethylimidazo[1,2-b]pyridazin-6-yl)-2-(1,2,3,6-tetrahydropyridin-4-yl)thiazolo[3,2-a]pyrimidin-5-one;

7-(2,8-dimethylimidazo[1,2-b]pyridazin-6-yl)-2-(3,3-dimethylpiperazin-1-yl)thiazolo[3,2-a]pyrimidin-5-one;

7-(4-fluoro-2-methyl-1,3-benzoxazol-6-yl)-2-piperazin-1-yl-thiazolo[3,2-a]pyrimidin-5-one;

7-(2,8-dimethylimidazo[1,2-b]pyridazin-6-yl)-2-[(3S)-3-methylpiperazin-1-yl]thiazolo[3,2-a]pyrimidin-5-one;

7-(2,8-dimethylimidazo[1,2-b]pyridazin-6-yl)-2-[(3R)-3-methylpiperazin-1-yl]thiazolo[3,2-a]pyrimidin-5-one;

7-(2,8-dimethylimidazo[1,2-b]pyridazin-6-yl)-2-(3,5-dimethylpiperazin-1-yl)thiazolo[3,2-a]pyrimidin-5-one;

7-(2,8-dimethylimidazo[1,2-b]pyridazin-6-yl)-2-[(8aS)-3,4,6,7,8,8a-hexahydro-1H-pyrrolo[1,2-a]pyrazin-2-yl]thiazolo[3,2-a]pyrimidin-5-one;

7-(2-methylimidazo[1,2-b]pyridazin-6-yl)-2-piperazin-1-yl-thiazolo[3,2-a]pyrimidin-5-one;

7-[2-methyl-8-(trifluoromethyl)imidazo[1,2-b]pyridazin-6-yl]-2-piperazin-1-yl-thiazolo[3,2-a]pyrimidin-5-one;

7-(8-ethyl-2-methyl-imidazo[1,2-b]pyridazin-6-yl)-2-piperazin-1-yl-thiazolo[3,2-a]pyrimidin-5-one;

7-(8-methoxy-2-methyl-imidazo[1,2-b]pyridazin-6-yl)-2-piperazin-1-yl-thiazolo[3,2-a]pyrimidin-5-one;

2-(3,8-diazabicyclo[3.2.1]octan-8-yl)-7-(2,8-dimethylimidazo[1,2-b]pyridazin-6-yl)thiazolo[3,2-a]pyrimidin-5-one;

7-(2,8-dimethylimidazo[1,2-b]pyridazin-6-yl)-2-[(8aR)-3,4,6,7,8,8a-hexahydro-1H-pyrrolo[1,2-a]pyrazin-2-yl]thiazolo[3,2-a]pyrimidin-5-one;

7-(2,8-dimethylimidazo[1,2-b]pyridazin-6-yl)-2-[(1S,4S)-2,5-diazabicyclo[2.2.1]heptan-2-yl]thiazolo[3,2-a]pyrimidin-5-one;
2-(2,3,3a,4,6,6a-hexahydro-1H-pyrrolo[3,4-c]pyrrol-5-yl)-7-(2,8-dimethylimidazo[1,2-b]pyridazin-6-yl)thiazolo[3,2-a]pyrimidin-5-one;
7-(8-cyclopropyl-2-methyl-imidazo[1,2-b]pyridazin-6-yl)-2-piperazin-1-yl-thiazolo[3,2-a]pyrimidin-5-one;
7-(8-isopropenyl-2-methyl-imidazo[1,2-b]pyridazin-6-yl)-2-piperazin-1-yl-thiazolo[3,2-a]pyrimidin-5-one;
7-(2,7-dimethyloxazolo[5,4-b]pyridin-5-yl)-2-piperazin-1-yl-thiazolo[3,2-a]pyrimidin-5-one;
7-(2,8-dimethylimidazo[1,2-b]pyridazin-6-yl)-2-[(3S)-3-pyrrolidin-1-ylpyrrolidin-1-yl]thiazolo[3,2-a]pyrimidin-5-one;
2-(2,8-diazaspiro[4.5]decan-2-yl)-7-(2,8-dimethylimidazo[1,2-b]pyridazin-6-yl)thiazolo[3,2-a]pyrimidin-5-one;
7-(8-isopropyl-2-methyl-imidazo[1,2-b]pyridazin-6-yl)-2-piperazin-1-yl-thiazolo[3,2-a]pyrimidin-5-one;
7-(2,8-dimethylimidazo[1,2-b]pyridazin-6-yl)-2-(4-piperidyl)thiazolo[3,2-a]pyrimidin-5-one;
7-[2-methyl-8-(trifluoromethyl)imidazo[1,2-b]pyridazin-6-yl]-2-[(8aR)-3,4,6,7,8,8a-hexahydro-1H-pyrrolo[1,2-a]pyrazin-2-yl]thiazolo[3,2-a]pyrimidin-5-one;
7-(2,8-dimethylimidazo[1,2-b]pyridazin-6-yl)-2-(4-fluoro-4-piperidyl)thiazolo[3,2-a]pyrimidin-5-one;
7-[8-(difluoromethoxy)-2-methyl-imidazo[1,2-b]pyridazin-6-yl]-2-piperazin-1-yl-thiazolo[3,2-a]pyrimidin-5-one;
7-[2-methyl-7-(trifluoromethyl)oxazolo[5,4-b]pyridin-5-yl]-2-piperazin-1-yl-thiazolo[3,2-a]pyrimidin-5-one;
7-(8-methoxy-2-methyl-imidazo[1,2-b]pyridazin-6-yl)-2-(4-piperidyl)thiazolo[3,2-a]pyrimidin-5-one;
7-(2,7-dimethyloxazolo[5,4-b]pyridin-5-yl)-2-(4-piperidyl)thiazolo[3,2-a]pyrimidin-5-one;
7-(2-chloro-8-methyl-imidazo[1,2-b]pyridazin-6-yl)-2-(4-piperidyl)thiazolo[3,2-a]pyrimidin-5-one;
7-(2,8-dimethylimidazo[1,2-b]pyridazin-6-yl)-2-[(3R,4R)-3-fluoro-4-piperidyl]thiazolo[3,2-a]pyrimidin-5-one;
7-(2,8-dimethylimidazo[1,2-b]pyridazin-6-yl)-2-[(3S,4S)-3-fluoro-4-piperidyl]thiazolo[3,2-a]pyrimidin-5-one;
7-(8-methoxy-2-methyl-imidazo[1,2-b]pyridazin-6-yl)-2-[(3R,4R)-3-fluoro-4-piperidyl]thiazolo[3,2-a]pyrimidin-5-one;
7-(8-methoxy-2-methyl-imidazo[1,2-b]pyridazin-6-yl)-2-[(3S,4S)-3-fluoro-4-piperidyl]thiazolo[3,2-a]pyrimidin-5-one;
7-(2,8-dimethylimidazo[1,2-b]pyridazin-6-yl)-2-[(7S)-4-azaspiro[2.5]octan-7-yl]thiazolo[3,2-a]pyrimidin-5-one;
7-(2,8-dimethylimidazo[1,2-b]pyridazin-6-yl)-2-[(7R)-4-azaspiro[2.5]octan-7-yl]thiazolo[3,2-a]pyrimidin-5-one;
7-(2,8-dimethylimidazo[1,2-b]pyridazin-6-yl)-2-[(3S,4R)-3-fluoro-4-piperidyl]thiazolo[3,2-a]pyrimidin-5-one;
7-(2,8-dimethylimidazo[1,2-b]pyridazin-6-yl)-2-[(3R,4S)-3-fluoro-4-piperidyl]thiazolo[3,2-a]pyrimidin-5-one;
7-(8-methoxy-2-methyl-imidazo[1,2-b]pyridazin-6-yl)-2-[(7S)-4-azaspiro[2.5]octan-7-yl]thiazolo[3,2-a]pyrimidin-5-one;
7-(8-methoxy-2-methyl-imidazo[1,2-b]pyridazin-6-yl)-2-[(7R)-4-azaspiro[2.5]octan-7-yl]thiazolo[3,2-a]pyrimidin-5-one;
2-(4-fluoro-4-piperidyl)-7-(8-methoxy-2-methyl-imidazo[1,2-b]pyridazin-6-yl)thiazolo[3,2-a]pyrimidin-5-one;
7-(2-chloro-8-methyl-imidazo[1,2-b]pyridazin-6-yl)-2-[(3R,4R)-3-fluoro-4-piperidyl]thiazolo[3,2-a]pyrimidin-5-one;
7-(2,7-dimethyloxazolo[5,4-b]pyridin-5-yl)-2-[(3R,4R)-3-fluoro-4-piperidyl]thiazolo[3,2-a]pyrimidin-5-one;
7-(8-methoxy-2-methyl-imidazo[1,2-b]pyridazin-6-yl)-2-[(3S,4R)-3-fluoro-4-piperidyl]thiazolo[3,2-a]pyrimidin-5-one;
7-(8-methoxy-2-methyl-imidazo[1,2-b]pyridazin-6-yl)-2-[(3R,4S)-3-fluoro-4-piperidyl]thiazolo[3,2-a]pyrimidin-5-one;
7-(2,8-dimethylimidazo[1,2-b]pyridazin-6-yl)-2-[rac-(1R,5S)-9-oxa-3-azabicyclo[3.3.1]nonan-7-yl]thiazolo[3,2-a]pyrimidin-5-one;
7-(2,8-dimethylimidazo[1,2-b]pyridazin-6-yl)-2-[rac-(1S,5R)-9-oxa-3-azabicyclo[3.3.1]nonan-7-yl]thiazolo[3,2-a]pyrimidin-5-one;
7-(8-methoxy-2-methyl-imidazo[1,2-b]pyridazin-6-yl)-2-[rac-(1R,5S)-9-oxa-3-azabicyclo[3.3.1]nonan-7-yl]thiazolo[3,2-a]pyrimidin-5-one;
7-(8-methoxy-2-methyl-imidazo[1,2-b]pyridazin-6-yl)-2-[rac-(1S,5R)-9-oxa-3-azabicyclo[3.3.1]nonan-7-yl]thiazolo[3,2-a]pyrimidin-5-one;
7-(8-methoxy-2-methyl-imidazo[1,2-b]pyridazin-6-yl)-2-[rac-(3R,4S)-3,4-difluoro-4-piperidyl]thiazolo[3,2-a]pyrimidin-5-one;
7-(8-methoxy-2-methyl-imidazo[1,2-b]pyridazin-6-yl)-2-[rac-(3S,4S)-3,4-difluoro-4-piperidyl]thiazolo[3,2-a]pyrimidin-5-one;
7-(2,8-dimethylimidazo[1,2-b]pyridazin-6-yl)-2-[rac-(3R,4S)-3,4-difluoro-4-piperidyl]thiazolo[3,2-a]pyrimidin-5-one;
7-(2,8-dimethylimidazo[1,2-b]pyridazin-6-yl)-2-[rac-(3S,4S)-3,4-difluoro-4-piperidyl]thiazolo[3,2-a]pyrimidin-5-one;
7-(2,8-dimethylimidazo[1,2-b]pyridazin-6-yl)-2-[rac-(1S,5R)-3-azabicyclo[3.1.0]hexan-6-yl]thiazolo[3,2-a]pyrimidin-5-one;
7-(8-methoxy-2-methyl-imidazo[1,2-b]pyridazin-6-yl)-2-[(3R,4S)-3,4-difluoro-4-piperidyl]thiazolo[3,2-a]pyrimidin-5-one;
7-(8-methoxy-2-methyl-imidazo[1,2-b]pyridazin-6-yl)-2-[(3S,4S)-3,4-difluoro-4-piperidyl]thiazolo[3,2-a]pyrimidin-5-one;
7-(8-methoxy-2-methyl-imidazo[1,2-b]pyridazin-6-yl)-2-[(3R,4R)-3,4-difluoro-4-piperidyl]thiazolo[3,2-a]pyrimidin-5-one; and
7-(8-methoxy-2-methyl-imidazo[1,2-b]pyridazin-6-yl)-2-[(3S,4R)-3,4-difluoro-4-piperidyl]thiazolo[3,2-a]pyrimidin-5-one;

or a pharmaceutically acceptable salt thereof.

The invention further relates to a compound selected from 7-(2,8-dimethylimidazo[1,2-b]pyridazin-6-yl)-2-piperazin-1-yl-thiazolo[3,2-a]pyrimidin-5-one;
7-(2,8-dimethylimidazo[1,2-b]pyridazin-6-yl)-2-(1,2,3,6-tetrahydropyridin-4-yl)thiazolo[3,2-a]pyrimidin-5-one;
7-(2,8-dimethylimidazo[1,2-b]pyridazin-6-yl)-2-(3,3-dimethylpiperazin-1-yl)thiazolo[3,2-a]pyrimidin-5-one;
7-(4-fluoro-2-methyl-1,3-benzoxazol-6-yl)-2-piperazin-1-yl-thiazolo[3,2-a]pyrimidin-5-one;
7-(2,8-dimethylimidazo[1,2-b]pyridazin-6-yl)-2-[(3S)-3-methylpiperazin-1-yl]thiazolo[3,2-a]pyrimidin-5-one;
7-(2,8-dimethylimidazo[1,2-b]pyridazin-6-yl)-2-[(3R)-3-methylpiperazin-1-yl]thiazolo[3,2-a]pyrimidin-5-one;
7-(2,8-dimethylimidazo[1,2-b]pyridazin-6-yl)-2-(3,5-dimethylpiperazin-1-yl)thiazolo[3,2-a]pyrimidin-5-one;
7-(2,8-dimethylimidazo[1,2-b]pyridazin-6-yl)-2-[(8aS)-3,4,6,7,8,8a-hexahydro-11H-pyrrolo[1,2-a]pyrazin-2-yl]thiazolo[3,2-a]pyrimidin-5-one;
7-(2-methylimidazo[1,2-b]pyridazin-6-yl)-2-piperazin-1-yl-thiazolo[3,2-a]pyrimidin-5-one;

7-[2-methyl-8-(trifluoromethyl)imidazo[1,2-b]pyridazin-6-yl]-2-piperazin-1-yl-thiazolo[3,2-a]pyrimidin-5-one;

7-(8-ethyl-2-methyl-imidazo[1,2-b]pyridazin-6-yl)-2-piperazin-1-yl-thiazolo[3,2-a]pyrimidin-5-one;

7-(8-methoxy-2-methyl-imidazo[1,2-b]pyridazin-6-yl)-2-piperazin-1-yl-thiazolo[3,2-a]pyrimidin-5-one;

2-(3,8-diazabicyclo[3.2.1]octan-8-yl)-7-(2,8-dimethylimidazo[1,2-b]pyridazin-6-yl)thiazolo[3,2-a]pyrimidin-5-one;

7-(2,8-dimethylimidazo[1,2-b]pyridazin-6-yl)-2-[(8aR)-3,4,6,7,8,8a-hexahydro-1H-pyrrolo[1,2-a]pyrazin-2-yl]thiazolo[3,2-a]pyrimidin-5-one;

7-(2,8-dimethylimidazo[1,2-b]pyridazin-6-yl)-2-[(1S,4S)-2,5-diazabicyclo[2.2.1]heptan-2-yl]thiazolo[3,2-a]pyrimidin-5-one;

2-(2,3,3a,4,6,6a-hexahydro-1H-pyrrolo[3,4-c]pyrrol-5-yl)-7-(2,8-dimethylimidazo[1,2-b]pyridazin-6-yl)thiazolo[3,2-a]pyrimidin-5-one;

7-(8-cyclopropyl-2-methyl-imidazo[1,2-b]pyridazin-6-yl)-2-piperazin-1-yl-thiazolo[3,2-a]pyrimidin-5-one;

7-(8-isopropenyl-2-methyl-imidazo[1,2-b]pyridazin-6-yl)-2-piperazin-1-yl-thiazolo[3,2-a]pyrimidin-5-one;

7-(2,7-dimethyloxazolo[5,4-b]pyridin-5-yl)-2-piperazin-1-yl-thiazolo[3,2-a]pyrimidin-5-one;

7-(2,8-dimethylimidazo[1,2-b]pyridazin-6-yl)-2-[(3S)-3-pyrrolidin-1-ylpyrrolidin-1-yl]thiazolo[3,2-a]pyrimidin-5-one;

2-(2,8-diazaspiro[4.5]decan-2-yl)-7-(2,8-dimethylimidazo[1,2-b]pyridazin-6-yl)thiazolo[3,2-a]pyrimidin-5-one;

7-(8-isopropyl-2-methyl-imidazo[1,2-b]pyridazin-6-yl)-2-piperazin-1-yl-thiazolo[3,2-a]pyrimidin-5-one;

7-(2,8-dimethylimidazo[1,2-b]pyridazin-6-yl)-2-(4-piperidyl)thiazolo[3,2-a]pyrimidin-5-one;

7-[2-methyl-8-(trifluoromethyl)imidazo[1,2-b]pyridazin-6-yl]-2-[(8aR)-3,4,6,7,8,8a-hexahydro-1H-pyrrolo[1,2-a]pyrazin-2-yl]thiazolo[3,2-a]pyrimidin-5-one;

7-(2,8-dimethylimidazo[1,2-b]pyridazin-6-yl)-2-(4-fluoro-4-piperidyl)thiazolo[3,2-a]pyrimidin-5-one;

7-[8-(difluoromethoxy)-2-methyl-imidazo[1,2-b]pyridazin-6-yl]-2-piperazin-1-yl-thiazolo[3,2-a]pyrimidin-5-one;

7-[2-methyl-7-(trifluoromethyl)oxazolo[5,4-b]pyridin-5-yl]-2-piperazin-1-yl-thiazolo[3,2-a]pyrimidin-5-one;

7-(8-methoxy-2-methyl-imidazo[1,2-b]pyridazin-6-yl)-2-(4-piperidyl)thiazolo[3,2-a]pyrimidin-5-one;

7-(2,7-dimethyloxazolo[5,4-b]pyridin-5-yl)-2-(4-piperidyl)thiazolo[3,2-a]pyrimidin-5-one;

7-(2-chloro-8-methyl-imidazo[1,2-b]pyridazin-6-yl)-2-(4-piperidyl)thiazolo[3,2-a]pyrimidin-5-one;

7-(2,8-dimethylimidazo[1,2-b]pyridazin-6-yl)-2-[(3R,4R)-3-fluoro-4-piperidyl]thiazolo[3,2-a]pyrimidin-5-one;

7-(2,8-dimethylimidazo[1,2-b]pyridazin-6-yl)-2-[(3S,4S)-3-fluoro-4-piperidyl]thiazolo[3,2-a]pyrimidin-5-one;

7-(8-methoxy-2-methyl-imidazo[1,2-b]pyridazin-6-yl)-2-[(3R,4R)-3-fluoro-4-piperidyl]thiazolo[3,2-a]pyrimidin-5-one;

7-(8-methoxy-2-methyl-imidazo[1,2-b]pyridazin-6-yl)-2-[(3S,4S)-3-fluoro-4-piperidyl]thiazolo[3,2-a]pyrimidin-5-one;

7-(2,8-dimethylimidazo[1,2-b]pyridazin-6-yl)-2-[(7S)-4-azaspiro[2.5]octan-7-yl]thiazolo[3,2-a]pyrimidin-5-one;

7-(2,8-dimethylimidazo[1,2-b]pyridazin-6-yl)-2-[(7R)-4-azaspiro[2.5]octan-7-yl]thiazolo[3,2-a]pyrimidin-5-one;

7-(2,8-dimethylimidazo[1,2-b]pyridazin-6-yl)-2-[(3S,4R)-3-fluoro-4-piperidyl]thiazolo[3,2-a]pyrimidin-5-one;

7-(2,8-dimethylimidazo[1,2-b]pyridazin-6-yl)-2-[(3R,4S)-3-fluoro-4-piperidyl]thiazolo[3,2-a]pyrimidin-5-one;

7-(8-methoxy-2-methyl-imidazo[1,2-b]pyridazin-6-yl)-2-[(7S)-4-azaspiro[2.5]octan-7-yl]thiazolo[3,2-a]pyrimidin-5-one;

7-(8-methoxy-2-methyl-imidazo[1,2-b]pyridazin-6-yl)-2-[(7R)-4-azaspiro[2.5]octan-7-yl]thiazolo[3,2-a]pyrimidin-5-one;

2-(4-fluoro-4-piperidyl)-7-(8-methoxy-2-methyl-imidazo[1,2-b]pyridazin-6-yl)thiazolo[3,2-a]pyrimidin-5-one;

7-(2-chloro-8-methyl-imidazo[1,2-b]pyridazin-6-yl)-2-[(3R,4R)-3-fluoro-4-piperidyl]thiazolo[3,2-a]pyrimidin-5-one or 7-(2,7-dimethyloxazolo[5,4-b]pyridin-5-yl)-2-[(3S,4S)-3-fluoro-4-piperidyl]thiazolo[3,2-a]pyrimidin-5-one;

7-(2,7-dimethyloxazolo[5,4-b]pyridin-5-yl)-2-[(3R,4R)-3-fluoro-4-piperidyl]thiazolo[3,2-a]pyrimidin-5-one or 7-(2,7-dimethyloxazolo[5,4-b]pyridin-5-yl)-2-[(3S,4S)-3-fluoro-4-piperidyl]thiazolo[3,2-a]pyrimidin-5-one;

7-(8-methoxy-2-methyl-imidazo[1,2-b]pyridazin-6-yl)-2-[(3S,4R)-3-fluoro-4-piperidyl]thiazolo[3,2-a]pyrimidin-5-one; and 7-(8-methoxy-2-methyl-imidazo[1,2-b]pyridazin-6-yl)-2-[(3R,4S)-3-fluoro-4-piperidyl]thiazolo[3,2-a]pyrimidin-5-one;

or a pharmaceutically acceptable salt thereof.

The invention further relates to a compound selected from 7-(2,8-dimethylimidazo[1,2-b]pyridazin-6-yl)-2-[rac-(1R,5S)-9-oxa-3-azabicyclo[3.3.1]nonan-7-yl]thiazolo[3,2-a]pyrimidin-5-one;

7-(2,8-dimethylimidazo[1,2-b]pyridazin-6-yl)-2-[rac-(1S,5R)-9-oxa-3-azabicyclo[3.3.1]nonan-7-yl]thiazolo[3,2-a]pyrimidin-5-one;

7-(8-methoxy-2-methyl-imidazo[1,2-b]pyridazin-6-yl)-2-[rac-(1R,5S)-9-oxa-3-azabicyclo[3.3.1]nonan-7-yl]thiazolo[3,2-a]pyrimidin-5-one;

7-(8-methoxy-2-methyl-imidazo[1,2-b]pyridazin-6-yl)-2-[rac-(1S,5R)-9-oxa-3-azabicyclo[3.3.1]nonan-7-yl]thiazolo[3,2-a]pyrimidin-5-one;

7-(8-methoxy-2-methyl-imidazo[1,2-b]pyridazin-6-yl)-2-[rac-(3R,4S)-3,4-difluoro-4-piperidyl]thiazolo[3,2-a]pyrimidin-5-one;

7-(8-methoxy-2-methyl-imidazo[1,2-b]pyridazin-6-yl)-2-[rac-(3S,4S)-3,4-difluoro-4-piperidyl]thiazolo[3,2-a]pyrimidin-5-one;

7-(2,8-dimethylimidazo[1,2-b]pyridazin-6-yl)-2-[rac-(3R,4S)-3,4-difluoro-4-piperidyl]thiazolo[3,2-a]pyrimidin-5-one;

7-(2,8-dimethylimidazo[1,2-b]pyridazin-6-yl)-2-[rac-(3S,4S)-3,4-difluoro-4-piperidyl]thiazolo[3,2-a]pyrimidin-5-one;

7-(2,8-dimethylimidazo[1,2-b]pyridazin-6-yl)-2-[rac-(1S,5R)-3-azabicyclo[3.1.0]hexan-6-yl]thiazolo[3,2-a]pyrimidin-5-one;

7-(8-methoxy-2-methyl-imidazo[1,2-b]pyridazin-6-yl)-2-[(3R,4S)-3,4-difluoro-4-piperidyl]thiazolo[3,2-a]pyrimidin-5-one;

7-(8-methoxy-2-methyl-imidazo[1,2-b]pyridazin-6-yl)-2-[(3S,4S)-3,4-difluoro-4-piperidyl]thiazolo[3,2-a]pyrimidin-5-one;

7-(8-methoxy-2-methyl-imidazo[1,2-b]pyridazin-6-yl)-2-[(3R,4R)-3,4-difluoro-4-piperidyl]thiazolo[3,2-a]pyrimidin-5-one; and 7-(8-methoxy-2-methyl-imidazo[1,2-b]pyridazin-6-yl)-2-[(3S,4R)-3,4-difluoro-4-piperidyl]thiazolo[3,2-a]pyrimidin-5-one;

or a pharmaceutically acceptable salt thereof.

The invention further relates to a compound selected from 7-(2,8-dimethylimidazo[1,2-b]pyridazin-6-yl)-2-piperazin-1-yl-thiazolo[3,2-a]pyrimidin-5-one;

7-(2,8-dimethylimidazo[1,2-b]pyridazin-6-yl)-2-(1,2,3,6-tetrahydropyridin-4-yl)thiazolo[3,2-a]pyrimidin-5-one;

7-(2,8-dimethylimidazo[1,2-b]pyridazin-6-yl)-2-[(3R)-3-methylpiperazin-1-yl]thiazolo[3,2-a]pyrimidin-5-one;

7-[2-methyl-8-(trifluoromethyl)imidazo[1,2-b]pyridazin-6-yl]-2-piperazin-1-yl-thiazolo[3,2-a]pyrimidin-5-one;

7-(8-ethyl-2-methyl-imidazo[1,2-b]pyridazin-6-yl)-2-piperazin-1-yl-thiazolo[3,2-a]pyrimidin-5-one;

7-(8-methoxy-2-methyl-imidazo[1,2-b]pyridazin-6-yl)-2-piperazin-1-yl-thiazolo[3,2-a]pyrimidin-5-one;

7-(2,8-dimethylimidazo[1,2-b]pyridazin-6-yl)-2-[(8aR)-3,4,6,7,8,8a-hexahydro-1H-pyrrolo[1,2-a]pyrazin-2-yl]thiazolo[3,2-a]pyrimidin-5-one;

7-(2,7-dimethyloxazolo[5,4-b]pyridin-5-yl)-2-piperazin-1-yl-thiazolo[3,2-a]pyrimidin-5-one;

7-(2,8-dimethylimidazo[1,2-b]pyridazin-6-yl)-2-(4-piperidyl)thiazolo[3,2-a]pyrimidin-5-one;

7-(2,8-dimethylimidazo[1,2-b]pyridazin-6-yl)-2-(4-fluoro-4-piperidyl)thiazolo[3,2-a]pyrimidin-5-one;

7-[8-(difluoromethoxy)-2-methyl-imidazo[1,2-b]pyridazin-6-yl]-2-piperazin-1-yl-thiazolo[3,2-a]pyrimidin-5-one;

7-(8-methoxy-2-methyl-imidazo[1,2-b]pyridazin-6-yl)-2-(4-piperidyl)thiazolo[3,2-a]pyrimidin-5-one;

7-(2,7-dimethyloxazolo[5,4-b]pyridin-5-yl)-2-(4-piperidyl)thiazolo[3,2-a]pyrimidin-5-one;

7-(2-chloro-8-methyl-imidazo[1,2-b]pyridazin-6-yl)-2-(4-piperidyl)thiazolo[3,2-a]pyrimidin-5-one;

7-(2,8-dimethylimidazo[1,2-b]pyridazin-6-yl)-2-[(3R,4R)-3-fluoro-4-piperidyl]thiazolo[3,2-a]pyrimidin-5-one;

7-(2,8-dimethylimidazo[1,2-b]pyridazin-6-yl)-2-[(3S,4S)-3-fluoro-4-piperidyl]thiazolo[3,2-a]pyrimidin-5-one;

7-(8-methoxy-2-methyl-imidazo[1,2-b]pyridazin-6-yl)-2-[(3R,4R)-3-fluoro-4-piperidyl]thiazolo[3,2-a]pyrimidin-5-one;

7-(8-methoxy-2-methyl-imidazo[1,2-b]pyridazin-6-yl)-2-[(3S,4S)-3-fluoro-4-piperidyl]thiazolo[3,2-a]pyrimidin-5-one;

7-(2,8-dimethylimidazo[1,2-b]pyridazin-6-yl)-2-[(7S)-4-azaspiro[2.5]octan-7-yl]thiazolo[3,2-a]pyrimidin-5-one;

7-(2,8-dimethylimidazo[1,2-b]pyridazin-6-yl)-2-[(7R)-4-azaspiro[2.5]octan-7-yl]thiazolo[3,2-a]pyrimidin-5-one;

7-(2,8-dimethylimidazo[1,2-b]pyridazin-6-yl)-2-[(3S,4R)-3-fluoro-4-piperidyl]thiazolo[3,2-a]pyrimidin-5-one;

7-(2,8-dimethylimidazo[1,2-b]pyridazin-6-yl)-2-[(3R,4S)-3-fluoro-4-piperidyl]thiazolo[3,2-a]pyrimidin-5-one;

7-(8-methoxy-2-methyl-imidazo[1,2-b]pyridazin-6-yl)-2-[(7S)-4-azaspiro[2.5]octan-7-yl]thiazolo[3,2-a]pyrimidin-5-one;

7-(8-methoxy-2-methyl-imidazo[1,2-b]pyridazin-6-yl)-2-[(7R)-4-azaspiro[2.5]octan-7-yl]thiazolo[3,2-a]pyrimidin-5-one;

2-(4-fluoro-4-piperidyl)-7-(8-methoxy-2-methyl-imidazo[1,2-b]pyridazin-6-yl)thiazolo[3,2-a]pyrimidin-5-one;

7-(8-methoxy-2-methyl-imidazo[1,2-b]pyridazin-6-yl)-2-[(3S,4R)-3-fluoro-4-piperidyl]thiazolo[3,2-a]pyrimidin-5-one;

7-(8-methoxy-2-methyl-imidazo[1,2-b]pyridazin-6-yl)-2-[(3R,4S)-3-fluoro-4-piperidyl]thiazolo[3,2-a]pyrimidin-5-one;

7-(8-methoxy-2-methyl-imidazo[1,2-b]pyridazin-6-yl)-2-[rac-(1S,5R)-9-oxa-3-azabicyclo[3.3.1]nonan-7-yl]thiazolo[3,2-a]pyrimidin-5-one;

7-(8-methoxy-2-methyl-imidazo[1,2-b]pyridazin-6-yl)-2-[rac-(3R,4S)-3,4-difluoro-4-piperidyl]thiazolo[3,2-a]pyrimidin-5-one;

7-(2,8-dimethylimidazo[1,2-b]pyridazin-6-yl)-2-[rac-(1S,5R)-3-azabicyclo[3.1.0]hexan-6-yl]thiazolo[3,2-a]pyrimidin-5-one; and 7-(8-methoxy-2-methyl-imidazo[1,2-b]pyridazin-6-yl)-2-[(3R,4S)-3,4-difluoro-4-piperidyl]thiazolo[3,2-a]pyrimidin-5-one;

or a pharmaceutically acceptable salt thereof.

The invention further relates to a compound selected from 7-(2,8-dimethylimidazo[1,2-b]pyridazin-6-yl)-2-piperazin-1-yl-thiazolo[3,2-a]pyrimidin-5-one;

7-(2,8-dimethylimidazo[1,2-b]pyridazin-6-yl)-2-(1,2,3,6-tetrahydropyridin-4-yl)thiazolo[3,2-a]pyrimidin-5-one;

7-(2,8-dimethylimidazo[1,2-b]pyridazin-6-yl)-2-[(3R)-3-methylpiperazin-1-yl]thiazolo[3,2-a]pyrimidin-5-one;

7-[2-methyl-8-(trifluoromethyl)imidazo[1,2-b]pyridazin-6-yl]-2-piperazin-1-yl-thiazolo[3,2-a]pyrimidin-5-one;

7-(8-ethyl-2-methyl-imidazo[1,2-b]pyridazin-6-yl)-2-piperazin-1-yl-thiazolo[3,2-a]pyrimidin-5-one;

7-(8-methoxy-2-methyl-imidazo[1,2-b]pyridazin-6-yl)-2-piperazin-1-yl-thiazolo[3,2-a]pyrimidin-5-one;

7-(2,8-dimethylimidazo[1,2-b]pyridazin-6-yl)-2-[(8aR)-3,4,6,7,8,8a-hexahydro-1H-pyrrolo[1,2-a]pyrazin-2-yl]thiazolo[3,2-a]pyrimidin-5-one;

7-(2,7-dimethyloxazolo[5,4-b]pyridin-5-yl)-2-piperazin-1-yl-thiazolo[3,2-a]pyrimidin-5-one;

7-(2,8-dimethylimidazo[1,2-b]pyridazin-6-yl)-2-(4-piperidyl)thiazolo[3,2-a]pyrimidin-5-one;

7-(2,8-dimethylimidazo[1,2-b]pyridazin-6-yl)-2-(4-fluoro-4-piperidyl)thiazolo[3,2-a]pyrimidin-5-one;

7-[8-(difluoromethoxy)-2-methyl-imidazo[1,2-b]pyridazin-6-yl]-2-piperazin-1-yl-thiazolo[3,2-a]pyrimidin-5-one;

7-(8-methoxy-2-methyl-imidazo[1,2-b]pyridazin-6-yl)-2-(4-piperidyl)thiazolo[3,2-a]pyrimidin-5-one;

7-(2,7-dimethyloxazolo[5,4-b]pyridin-5-yl)-2-(4-piperidyl)thiazolo[3,2-a]pyrimidin-5-one;

7-(2-chloro-8-methyl-imidazo[1,2-b]pyridazin-6-yl)-2-(4-piperidyl)thiazolo[3,2-a]pyrimidin-5-one;

7-(2,8-dimethylimidazo[1,2-b]pyridazin-6-yl)-2-[(3R,4R)-3-fluoro-4-piperidyl]thiazolo[3,2-a]pyrimidin-5-one;

7-(2,8-dimethylimidazo[1,2-b]pyridazin-6-yl)-2-[(3S,4S)-3-fluoro-4-piperidyl]thiazolo[3,2-a]pyrimidin-5-one;

7-(8-methoxy-2-methyl-imidazo[1,2-b]pyridazin-6-yl)-2-[(3R,4R)-3-fluoro-4-piperidyl]thiazolo[3,2-a]pyrimidin-5-one;

7-(8-methoxy-2-methyl-imidazo[1,2-b]pyridazin-6-yl)-2-[(3S,4S)-3-fluoro-4-piperidyl]thiazolo[3,2-a]pyrimidin-5-one;

7-(2,8-dimethylimidazo[1,2-b]pyridazin-6-yl)-2-[(7S)-4-azaspiro[2.5]octan-7-yl]thiazolo[3,2-a]pyrimidin-5-one;

7-(2,8-dimethylimidazo[1,2-b]pyridazin-6-yl)-2-[(7R)-4-azaspiro[2.5]octan-7-yl]thiazolo[3,2-a]pyrimidin-5-one;

7-(2,8-dimethylimidazo[1,2-b]pyridazin-6-yl)-2-[(3S,4R)-3-fluoro-4-piperidyl]thiazolo[3,2-a]pyrimidin-5-one;

7-(2,8-dimethylimidazo[1,2-b]pyridazin-6-yl)-2-[(3R,4S)-3-fluoro-4-piperidyl]thiazolo[3,2-a]pyrimidin-5-one;

7-(8-methoxy-2-methyl-imidazo[1,2-b]pyridazin-6-yl)-2-[(7S)-4-azaspiro[2.5]octan-7-yl]thiazolo[3,2-a]pyrimidin-5-one;

7-(8-methoxy-2-methyl-imidazo[1,2-b]pyridazin-6-yl)-2-[(7R)-4-azaspiro[2.5]octan-7-yl]thiazolo[3,2-a]pyrimidin-5-one;

2-(4-fluoro-4-piperidyl)-7-(8-methoxy-2-methyl-imidazo[1,2-b]pyridazin-6-yl)thiazolo[3,2-a]pyrimidin-5-one;

7-(8-methoxy-2-methyl-imidazo[1,2-b]pyridazin-6-yl)-2-[(3S,4R)-3-fluoro-4-piperidyl]thiazolo[3,2-a]pyrimidin-5-one; and 7-(8-methoxy-2-methyl-imidazo[1,2-b]pyridazin-6-yl)-2-[(3R,4S)-3-fluoro-4-piperidyl]thiazolo[3,2-a]pyrimidin-5-one;

or a pharmaceutically acceptable salt thereof.

The invention further relates to a compound selected from 7-(2,8-dimethylimidazo[1,2-b]pyridazin-6-yl)-2-(1,2,3,6-tetrahydropyridin-4-yl)thiazolo[3,2-a]pyrimidin-5-one; and 7-(2,8-dimethylimidazo[1,2-b]pyridazin-6-yl)-2-[(3R)-3-methylpiperazin-1-yl]thiazolo[3,2-a]pyrimidin-5-one;

or a pharmaceutically acceptable salt thereof.

The invention further relates to a compound selected from 7-(8-methoxy-2-methyl-imidazo[1,2-b]pyridazin-6-yl)-2-[(7R)-4-azaspiro[2.5]octan-7-yl]thiazolo[3,2-a]pyrimidin-5-one; and 7-(8-methoxy-2-methyl-imidazo[1,2-b]pyridazin-6-yl)-2-[(7S)-4-azaspiro[2.5]octan-7-yl]thiazolo[3,2-a]pyrimidin-5-one;

or a pharmaceutically acceptable salt thereof.

The invention further relates to a compound selected from 7-(2,8-dimethylimidazo[1,2-b]pyridazin-6-yl)-2-(4-fluoro-4-piperidyl)thiazolo[3,2-a]pyrimidin-5-one;

7-(2,8-dimethylimidazo[1,2-b]pyridazin-6-yl)-2-[(3R,4R)-3-fluoro-4-piperidyl]thiazolo[3,2-a]pyrimidin-5-one;

7-(2,8-dimethylimidazo[1,2-b]pyridazin-6-yl)-2-[(3S,4S)-3-fluoro-4-piperidyl]thiazolo[3,2-a]pyrimidin-5-one;

7-(8-methoxy-2-methyl-imidazo[1,2-b]pyridazin-6-yl)-2-[(3R,4R)-3-fluoro-4-piperidyl]thiazolo[3,2-a]pyrimidin-5-one;

7-(8-methoxy-2-methyl-imidazo[1,2-b]pyridazin-6-yl)-2-[(3S,4S)-3-fluoro-4-piperidyl]thiazolo[3,2-a]pyrimidin-5-one; and 2-(4-fluoro-4-piperidyl)-7-(8-methoxy-2-methyl-imidazo[1,2-b]pyridazin-6-yl)thiazolo[3,2-a]pyrimidin-5-one;

or a pharmaceutically acceptable salt thereof.

The synthesis of the compound of formula (I) can, for example, be accomplished according to the following schemes. $R^1$-$R^4$ and $A_1$-$A_3$ are as defined above, unless otherwise specified.

Scheme 1

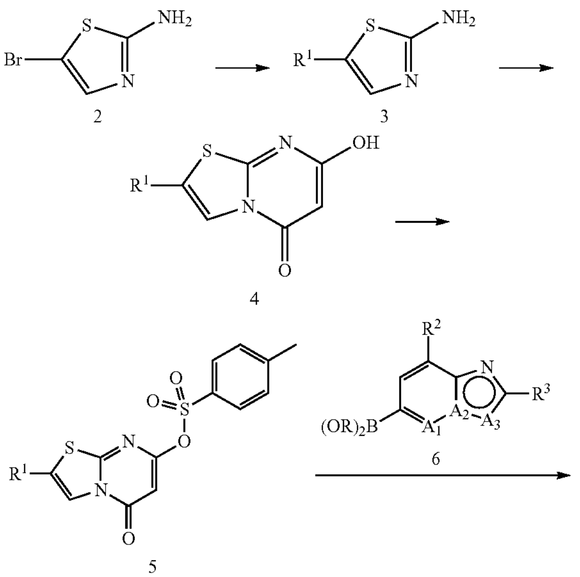

2 3 4 5 6

-continued

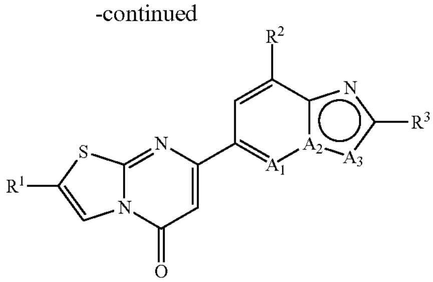

(I)

The compound of formula (I) wherein $R^1$ is a N-linked heterocycloalkyl or N-linked heteroaryl, can be made according to scheme 1. The preparation of such compounds is commenced by an aromatic nucleophilic substitution reaction of the commercially available 5-bromothiazol-2-amine (or a suitable derivate thereof) 2 with a $R^1$ heterocycle or heteroaryl (and wherein $R^1$ may further contain a protecting group) in presence of a base such as $K_2CO_3$ and a polar solvent as DMF, leading to 3. Following a condensation with commercially available bis(2,4,6-trichlorophenyl) propanedioate, the resulting intermediate 4 was obtained, which readily reacted with tosyl chlorid in presence of an organic base such as triethyl amine to yield 5. A Suzuki-cross coupling reaction between 5 and a suitable boronic acid 6, wherein in —$B(OR)_2$ each R is independently selected from hydrogen and alkyl or —$B(OR)_2$ is optionally substituted dioxaborolanyl. The Suzuki-cross coupling between 5 and 6 in 1,4-dioxane, acetonitrile, water or a mixture thereof, in presence of a base such as $K_2CO_3$ and a suitable palladium catalyst yields the compound of formula (I) (after an eventual removal of a protecting group on the $R^1$ moiety).

Scheme 2

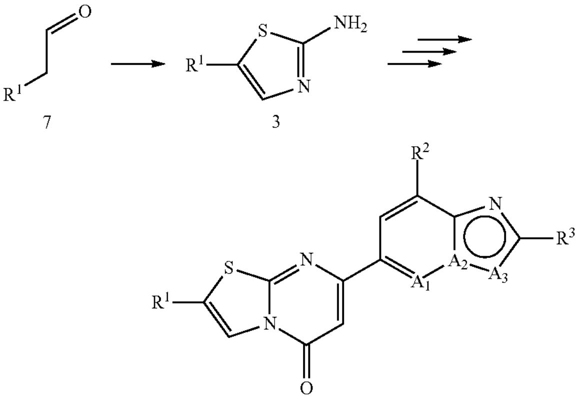

7 3

(I)

The compound of formula (I) wherein $R^1$ is a C-linked heterocycloalkyl, C-linked heteroaryl, cycloalkyl, aryl or alkyl can be made according to scheme 2. The synthesis of such compounds starts with a commercially available aldehyde (or as described herein below and wherein $R^1$ may further contain a protecting group) 7, which is converted readily into the aminothiazole derivatives of formula 3 following a sequential bromination and cyclisation with thiourea. The same synthetic sequence is then performed as in scheme 1 from intermediate 3 to form the compound of formula (I) (after an eventual removal of a protecting group on the $R^1$ moiety).

Scheme 3

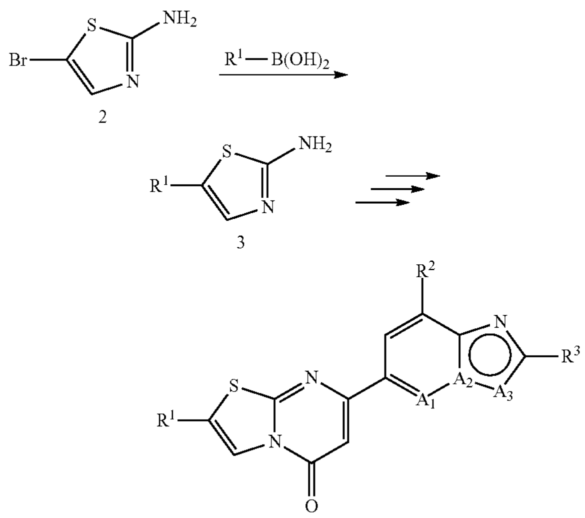

2

3

(I)

Alternatively, the compound of formula (I) wherein $R^1$ is a C-linked heterocycloalkyl, C-linked heteroaryl, cycloalkyl aryl or alkyl can be made according to scheme 3. This alternative synthesis starts from the 5-bromothiazol-2-amine compound (or a derivative thereof) 2 which undergoes a Suzuki-cross coupling with a boronic acid of formula RIB $(OH)_2$ to yield the intermediate of formula 3 (wherein $R^1$ may further contain a protecting group). The same synthetic sequence is then performed as in scheme 1 from intermediate 3 to form the compound of formula (I) (after an eventual removal of a protecting group on the $R^1$ moiety).

The invention thus also relates to a process for the preparation of a compound according to the invention, comprising at least one of the following steps:

(a) the reaction of a compound of formula (B1)

(B1)

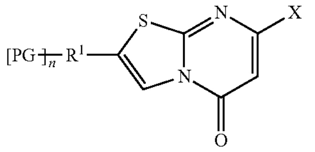

with a compound of formula (B2)

(B2)

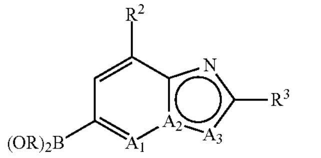

in a suitable solvent in the presence of a base and a suitable palladium catalyst, wherein n is 0 or 1, X is O-tosylate, O-triflate, O-mesylate or halogen, and wherein in —$B(OR)_2$ each R is independently selected from hydrogen and alkyl, or —$B(OR)_2$ is optionally substituted dioxaborolanyl, to arrive at a compound of formula (B3)

(B3)

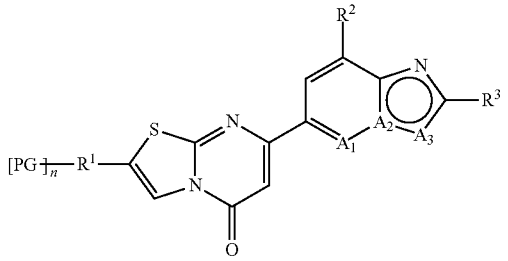

(b) the reaction of the compound of formula (B3), wherein n is 1, in a suitable solvent and in presence of an acid to yield the compound of formula (I)

(I)

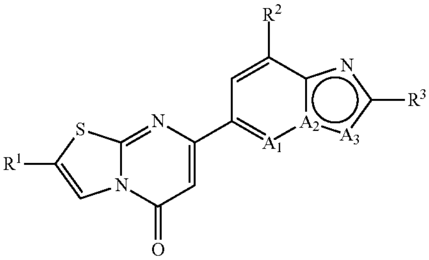

wherein in the process $R^1$, $R^2$, $R^3$, $R^4$, $A_1$, $A_2$ and $A_3$ are as defined above, and PG is a protecting group.

The reaction of step (a) can be conveniently carried out in a solvent. The solvent can be for example 1,4-dioxane, acetonitrile, water or a mixture thereof;

In the reaction of step (a), the base can be for example $K_2CO_3$, $Li_2CO_3$, $Na_2CO_3$, KOtBu, $Cs_2CO_3$, NaOtBu or LiOtBu, in particular $K_2CO_3$;

In the reaction of step (a), the palladium catalyst can be for example Pd(dppf)$Cl_2$ $CH_2Cl_2$ (CAS #95464-05-4) or XPhos PdG4 (CAS #1599466-81-5);

In the reaction of step (a), X is conveniently 0-tosylate or chloro, in particular O-tosylate;

In the reaction of step (a), $B(OR)_2$ can be for example dioxaborolanyl optionally substituted with one, two, three or four alkyl, in particular 4,4,5,5-tetramethyl-1,3,2-dioxaborolan-2-yl;

Convenient conditions for the reaction of step (a) are around 20° C.-150° C., particularly around 40° C.-130° C., more particularly around 60° C.-110° C., in particular around 90° C.;

Particular conditions for the reaction of step (a) are the use of $K_2CO_3$ in 1,4-dioxane, acetonitrile, water or a mixture thereof at around 90° C. for around 2 hrs-8 hrs;

The reaction of step (b) can be conveniently carried out in a solvent. The solvent can be for example $CH_2Cl_2$ or 1,4-dioxane;

In the reaction of step (b) the acid can be for example TFA or HCl;

Convenient conditions for the reaction of step (b) are around 0° C.-100° C., particularly around 5° C.-80° C., more particularly around 10° C.-60° C., in particular around 15° C.-40° C.;

Particular conditions for the reaction of step (b) are the use of TFA in $CH_2Cl_2$ at around 15-40° C. for around 1 hrs-24 hrs, in particular for around 1 h-3 hrs;

In the process, the protecting group can be for example Boc, Trt or Dmb, in particular Boc.

The invention also relates to a compound according to the invention when manufactured according to a process of the invention.

The invention thus also relates in particular to:

- A compound according to the invention for use as therapeutically active substance;
- A pharmaceutical composition comprising a compound according to the invention and a therapeutically inert carrier;
- A compound according to the invention for use in the treatment or prophylaxis of a neurodegenerative disease;
- A compound according to the invention for use in the treatment or prophylaxis of Huntington's disease;
- The use of a compound according to the invention for the treatment or prophylaxis of a neurodegenerative disease, in particular Huntington's disease;
- The use of a compound according to the invention for the preparation of a medicament for the treatment or prophylaxis of a neurodegenerative disease, in particular Huntington's disease; and
- A method for the treatment or prophylaxis of a neurodegenerative disease, in particular Huntington's disease, which method comprises administering an effective amount of a compound according to the invention to a patient in need thereof.

A certain embodiment of the invention relates to a pharmaceutical composition comprising the compound of formula (I) as described herein, or a pharmaceutically acceptable salt thereof, and a pharmaceutically acceptable auxiliary substance.

Furthermore, the invention includes all substituents in its corresponding deuterated form, wherever applicable, of the compound of formula (I).

Furthermore, the invention includes all optical isomers, i.e. diastereoisomers, diastereomeric mixtures, racemic mixtures, all their corresponding enantiomers and/or tautomers as well as their solvates, wherever applicable, of the compound of formula (I).

The compound of formula (I) may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

In a particular embodiment, the compounds of the present invention have favourable brain penetration properties.

Also an embodiment of the present invention is a compound of formula (I) as described herein, when manufactured according to any one of the described processes.

The compound of formula (I) or a pharmaceutically acceptable salt thereof can be used as a medicament (e.g. in the form of a pharmaceutical preparation). The pharmaceutical preparation can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compound of formula (I) or a pharmaceutically acceptable salt thereof can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparation can contain preservatives, solubilizers, viscosity-increasing substances, stabilizers, wetting agents, emulsifiers, sweeteners, colorants, flavorants, salts for varying the osmotic pressure, buffers, masking agents or antioxidants. The pharmaceutical preparation can also contain still other therapeutically valuable substances.

The dosage can vary in wide limits and will be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

Pharmaceutical Compositions

The compound of formula (I) or a pharmaceutically acceptable salt thereof can be used as a therapeutically active substance, e.g. in the form of a pharmaceutical preparation. The pharmaceutical preparation can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compound of formula (I) or a pharmaceutically acceptable salt thereof can be processed with pharmaceutically inert, inorganic or organic carriers for the production of a pharmaceutical preparation. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparation can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula (I) or a pharmaceutically acceptable salt thereof and a therapeutically inert carrier are also provided by the present invention, as is a process for their production, which comprises bringing a compound of formula (I) and/or pharmaceutically acceptable salts thereof and, if desired, one or more other therapeutically valuable substances into a galenical administration form together with one or more therapeutically inert carriers.

The dosage can vary within wide limits and will, have to be adjusted to the individual requirements in each particular case. In the case of oral administration the dosage for adults can vary from about 0.01 mg to about 1000 mg per day of a compound of general formula (I) or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparation conveniently contains about 1-500 mg, particularly 1-100 mg, of a compound of formula (I). Examples of compositions according to the invention are:

EXAMPLE A

Tablets of the following composition are manufactured in the usual manner:

TABLE 1 possible tablet composition

| ingredient | mg/tablet 5 | 25 | 100 | 500 |
|---|---|---|---|---|
| Compound of formula (I) | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 2 possible capsule ingredient composition

| ingredient | mg/capsule 5 | 25 | 100 | 500 |
|---|---|---|---|---|
| Compound of formula (I) | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula (I), lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 3

| possible soft gelatin capsule ingredient composition | |
|---|---|
| ingredient | mg/capsule |
| Compound of formula (I) | 5 |
| Yellow wax | 8 |
| Hydrogenated Soya bean oil | 8 |
| Partially hydrogenated plant oils | 34 |
| Soya bean oil | 110 |
| Total | 165 |

TABLE 4

| possible soft gelatin capsule composition | |
|---|---|
| ingredient | mg/capsule |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula (I) is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 5

| possible suppository composition | |
|---|---|
| ingredient | mg/supp. |
| Compound of formula (I) | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula (I) is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 6

| possible injection solution composition | |
|---|---|
| ingredient | mg/injection solution. |
| Compound of formula (I) | 3 |
| Polyethylene Glycol 400 | 150 |
| acetic acid | q.s. ad pH 5.0 |
| water for injection solutions | ad 1.0 ml |

Manufacturing Procedure

The compound of formula (I) is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 7

| possible sachet composition | |
|---|---|
| ingredient | mg/sachet |
| Compound of formula (I) | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula (I) is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

Abbreviations

AcCl: acetyl chloride; ACN: acetonitrile; AcOH: acetic acid; Boc: tert-butyloxycarbonyl; DAST: diethylaminosulfur trifluoride; DCM: dichloromethane; DIBAL-H: diisobutylaluminium hydride; DMAP: 4-dimethylaminopyridine; DMF: dimethylformamide; DMSO: dimethyl sulfoxide; dppf: bis (diphenylphosphino)ferrocene; dppp: 1,3-bis-(diphenylphosphino)-propan; ES+: positive electronspray ionization; EtOAc: ethyl acetate; EtOH: ethanol; HPLC: high performance liquid chromatography; HTRF: homogeneous time resolved fluorescence; iPrOH: isopropanol; LAH: lithium aluminium hydride; LCMS: liquid chromatography mass spectrometry; MeOH: methanol; MS: mass spectrometry; PPTS: pyridinium p-toluenesulfonate; RP-HPLC: reversed phase-high performance liquid chromatography; RT: room temperature; SFC: supercritical fluid chromatography; TBME: tert-butyl methyl ether; TEA: triethylamine; TFA: trifluoroacetic acid; THF: tetrahydrofuran.

The following examples are provided for illustration of the invention. They should not be considered as limiting the scope of the invention, but merely as being representative thereof.

Synthesis of Intermediates of Formula 3

Intermediate 3-1 tert-butyl 4-(2-aminothiazol-5-yl)piperazine-1-carboxylate

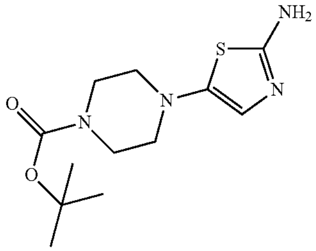 [SMILES: CC(C)(C)OC(=O)N1CCN(c2cnc(N)s2)CC1]

In a stirred solution of DMSO (28.0 mL) was added (5-bromothiazol-2-yl)amine (5.0 g, 27.9 mmol), $Et_3N$ (11.7 mL, 83.8 mmol) and commercially available 1-boc-piperazine (7.8 g, 41.9 mmol). The reaction mixture was heated at 100° C. for 6 hours before cooling down to RT. The crude reaction mixture was partitioned between EtOAc (100 mL) and $H_2O$ (100 mL) and the separated. The aqueous phase was extracted with EtOAc. The combined organic phases were dried over $Na_2SO_4$, filtered and concentrated under vacuo. The solid residue was triturated in EtOAC/n-heptane and the solid collected by filtration and dried under vacuo to yield tert-butyl 4-(2-aminothiazol-5-yl)piperazine-1-carboxylate as a light brown solid (3.30 g, 42% yield). MS (ES+) m/z: 285.2 [$(M+H)^+$].

Intermediate 3-2 tert-butyl 4-(2-aminothiazol-5-yl)-3,6-dihydro-2H-pyridine-1-carboxylate

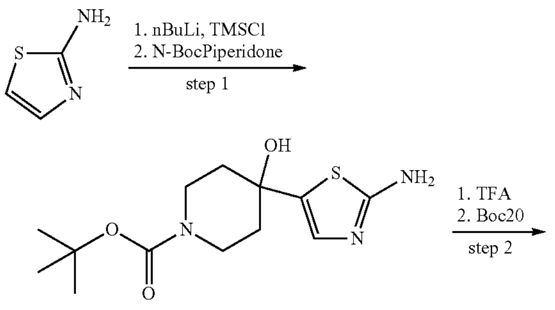

-continued

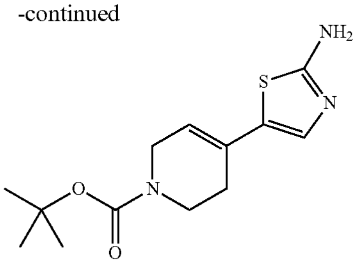

3-2

Step 1: Carbinols such as 4-(2-aminothiazol-5-yl)-4-hydroxy-piperidine-1l-carboxylic acid tert-butyl ester are obtained following the experimental procedures described in details by Katritzky et. al. CAN. J. CHEM. volume 66, 1988.

Step 2: A solution of 4-(2-aminothiazol-5-yl)-4-hydroxy-piperidine-1-carboxylic acid tert-butyl ester (300 mg, 0.962 mmol) in TFA (5 mL) was stirred at 65° C. until Boc deprotection and dehydration had reached completion, usually between 4 and 16 hours. Volatiles were evaporated and then azeotroped with toluene (15 mL×3), the residue is then resuspended in 9 mL of a 1:1 mixture of 1M $NaHCO_3$ and 1,4-dioxane, cooled to 0° C. and treated with Boc anhydride (231 mg, 1.06 mmol). Upon completion, the reaction is diluted with ethyl acetate and extracted, dried over $Na_2SO_4$, filtered and purified on silica gel, eluting with MeOH in DCM from 0 to 20% in 25 minutes.

4-(2-aminothiazol-5-yl)-3,6-dihydro-2H-pyridine-1-carboxylic acid tert-butyl ester derivative 3-2 (160 mg, 59% yield) was obtained as a white solid. MS (ES+) m/z: 282.2 $[M+H]^+$.

Intermediate 3-3 tert-butyl 4-(2-aminothiazol-5-yl)-2,2-dimethyl-piperazine-1-carboxylate

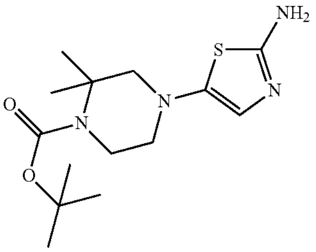 [SMILES: CC(C)(C)OC(=O)N1CCN(c2cnc(N)s2)CC1(C)C]

In a stirred solution of DMF (10.0 mL) was added (5-bromothiazol-2-yl)amine (1.0 g, 5.59 mmol), $K_2CO_3$ (3.09 g, 22.3 mmol) and commercially available 2,2-dimethylpiperazine-1-carboxylic acid tert-butyl ester (1.44 g, 6.7 mmol). The reaction mixture was heated at 70° C. for 1 hours before cooling down to RT and DMF mostly evaporated. The crude reaction mixture was partitioned between EtOAc (50 mL) and a 1M aqueous solution of $NaHCO_3$ (50 mL) and the separated. The aqueous phase was extracted with EtOAc. The combined organic phases were dried over $Na_2SO_4$, filtered and concentrated under vacuo and a purification by column chromatography ($CH_2Cl_2$/MeOH) under yielded tert-butyl 4-(2-aminothiazol-5-yl)-2,2-dimethyl-piperazine-1-carboxylate as an orange solid (1.06 g, 60% yield). MS (ES+) m/z: 313.3 [$(M+H)^+$].

Intermediate 3-4 tert-butyl 7-(2-aminothiazol-5-yl)-4,7-diazaspiro[2.5]octane-4-carboxylate

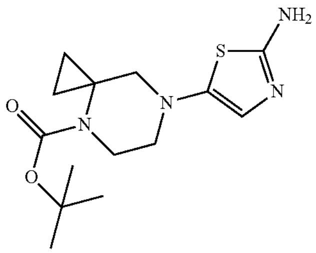 [SMILES: CC(C)(C)OC(=O)N1CCN(c2cnc(N)s2)CC12CC2]

In analogy to the preparation of the intermediate 3-3, from commercially available 4,7-diazaspiro[2.5]octane-4-carboxylic acid tert-butyl ester, the title compound was prepared as a red oil (360 mg, 55% yield). MS (ES+) m/z: 311.5 $[(M+H)^+]$.

Intermediate 3-5 tert-butyl (2S)-4-(2-aminothiazol-5-yl)-2-methyl-piperazine-1-carboxylate

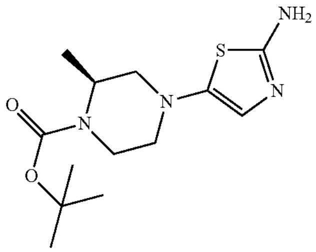 [SMILES: C[C@H]1CN(c2cnc(N)s2)CCN1C(=O)OC(C)(C)C]

In analogy to the preparation of the intermediate 3-3, from commercially available (2S)-2-methylpiperazine-1-carboxylic acid tert-butyl ester, the title compound was prepared as a red oil (408 mg, 64% yield). MS (ES+) m/z: 299.2 $[(M+H)^+]$.

Intermediate 3-6 tert-butyl (2R)-4-(2-aminothiazol-5-yl)-2-methyl-piperazine-1-carboxylate

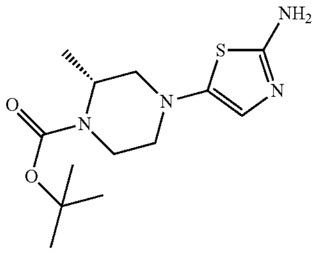 [SMILES: C[C@@H]1CN(c2cnc(N)s2)CCN1C(=O)OC(C)(C)C]

In analogy to the preparation of the intermediate 3-3, from commercially available (2R)-2-methylpiperazine-1-carboxylic acid tert-butyl ester, the title compound was prepared as a red solid (339 mg, 53% yield). MS (ES+) m/z: 299.2 $[(M+H)^+]$.

Intermediate 3-7 tert-butyl 4-(2-aminothiazol-5-yl)-2,6-dimethyl-piperazine-1-carboxylate

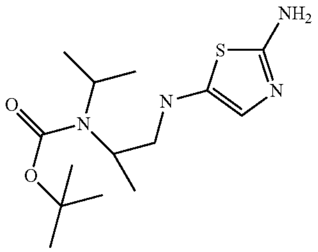 [SMILES: CC(C)N(C(=O)OC(C)(C)C)C(C)CNc1cnc(N)s1]

In analogy to the preparation of the intermediate 3-3, from commercially available 2,6-dimethylpiperazine-1-carboxylic acid tert-butyl ester, the title compound was prepared as a red oil (328 mg, 53% yield). MS (ES+) m/z: 313.3 $[(M+H)^+]$.

Intermediate 3-8

5-[(8aS)-3,4,6,7,8,8a-hexahydro-1H-pyrrolo[1,2-a]pyrazin-2-yl]thiazol-2-amine

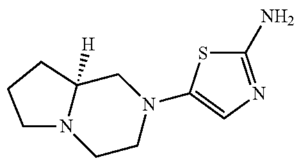 [SMILES: Nc1ncc(N2CCN3CCC[C@H]3C2)s1]

In analogy to the preparation of the intermediate 3-3, from commercially available (8aS)-1,2,3,4,6,7,8,8a-octahydropyrrolo[1,2-a]pyrazine, the title compound was prepared as a red oil (240 mg, 50% yield). MS (ES+) m/z: 225.1 $[(M+H)^+]$.

Intermediate 3-9 tert-butyl 8-(2-aminothiazol-5-yl)-3,8-diazabicyclo[3.2.1]octane-3-carboxylate

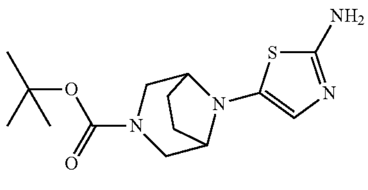 [SMILES: CC(C)(C)OC(=O)N1CC2CCC(C1)N2c1cnc(N)s1]

In analogy to the preparation of the intermediate 3-3, from commercially available 3,8-diazabicyclo[3.2.1]octane-3-carboxylic acid tert-butyl ester, the title compound was prepared as a light red solid (357 mg, 59% yield). MS (ES+) m/z: 311.3 [(M+H)$^+$].

Intermediate 3-10

5-[(8aR)-3,4,6,7,8,8a-hexahydro-1H-pyrrolo[1,2-a]pyrazin-2-yl]thiazol-2-amine

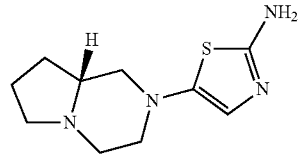 [SMILES: Nc1ncc(N2CCN3CCC[C@@H]3C2)s1]

In analogy to the preparation of the intermediate 3-3, from (8aR)-1,2,3,4,6,7,8,8a-octahydropyrrolo[1,2-a]pyrazine, the title compound was prepared as a red oil (200 mg, 55% yield). MS (ES+) m/z: 225.1 [(M+H)$^+$].

Intermediate 3-11 tert-butyl (1S,4S)-5-(2-aminothiazol-5-yl)-2,5-diazabicyclo[2.2.1]heptane-2-carboxylate

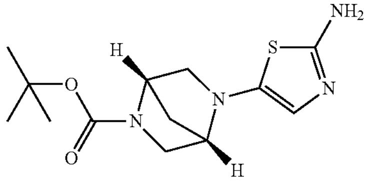 [SMILES: CC(C)(C)OC(=O)N1C[C@@H]2C[C@H]1CN2c1cnc(N)s1]

In analogy to the preparation of the intermediate 3-3, from commercial available (1S,4S)-2,5-diazabicyclo[2.2.1]heptane-2-carboxylic acid tert-butyl ester, the title compound was prepared as a red oil (295 mg, 51% yield). MS (ES+) m/z: 297.2 [(M+H)$^+$].

Intermediate 3-12 tert-butyl 2-(2-aminothiazol-5-yl)-1,3,3a,4,6,6a-hexahydropyrrolo[3,4-c]pyrrole-5-carboxylate

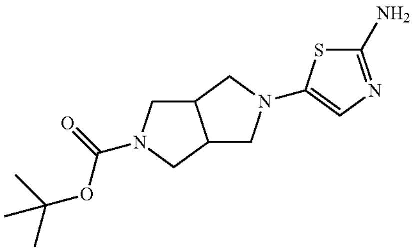 [SMILES: CC(C)(C)OC(=O)N1CC2CN(c3cnc(N)s3)CC2C1]

In analogy to the preparation of the intermediate 3-3, from 2,3,3a,4,6,6a-hexahydro-1H-pyrrolo[3,4-c]pyrrole-5-carboxylic acid tert-butyl ester, the title compound was prepared as a red solid (219 mg, 33% yield). MS (ES+) m/z: 311.2 [(M+H)$^+$].

Intermediate 3-13

5-[(3S)-3-pyrrolidin-1-ylpyrrolidin-1-yl]thiazol-2-amine

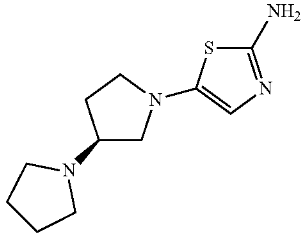 [SMILES: Nc1ncc(N2CC[C@H](N3CCCC3)C2)s1]

In analogy to the preparation of the intermediate 3-3, from 1-[(3S)-pyrrolidin-3-yl]pyrrolidine, the title compound was prepared as a red solid (517 mg, 90% yield). MS (ES+) m/z: 239.2 [(M+H)$^+$].

Intermediate 3-14 tert-butyl 2-(2-aminothiazol-5-yl)-2,8-diazaspiro[4.5]decane-8-carboxylate

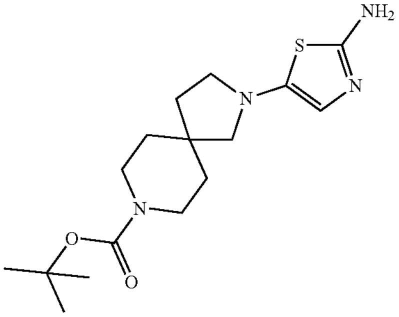 [SMILES: CC(C)(C)OC(=O)N1CCC2(CC1)CCN(c1cnc(N)s1)C2]

In analogy to the preparation of the intermediate 3-3, from 2,8-diazaspiro[4.5]decane-8-carboxylic acid tert-butyl ester, the title compound was prepared as a red solid (161 mg, 15% yield). MS (ES+) m/z: 339.2 [(M+H)$^+$].

Intermediate 3-15 tert-butyl 4-(2-aminothiazol-5-yl)piperidine-1-carboxylate

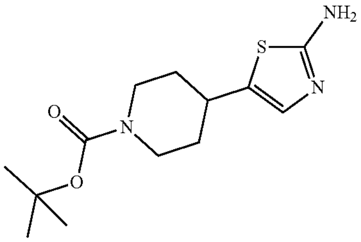 [SMILES: CC(C)(C)OC(=O)N1CCC(c2cnc(N)s2)CC1]

Step 1: In a two-necked round bottom flask oxalyl chloride (1.4 mL, 16.05 mmol), diluted in anhydrous $CH_2Cl_2$ (20 mL), was cooled to −78° C. and treated over the course of 20 minutes with a solution of DMSO (2.28 mL, 32.09 mmol) diluted in anhydrous $CH_2Cl_2$ (20 mL). The resulting solution was stirred at the same temperature for 20 minutes before adding 4-(2-hydroxyethyl)piperidine-1-carboxylic acid tert-butyl ester (3.2 g, 13.95 mmol) dissolved in anhydrous $CH_2Cl_2$ (20 mL), over the course of 15 minutes. The resulting milky solution was left stirring for 45 minutes before dropwise addition of TEA (9.72 mL, 69.77 mmol). The resulting milky suspension was warmed to room temperature to obtain a foamy suspension. The mixture was diluted with DCM and water, layers were separated and the organic layer was treated with $Na_2SO_4$, filtered and reduced to small volume. The residue was loaded onto a Silica cartridge and purified with a gradient of EtOAc in heptane from 0 to 100% in 25 minutes, flow 30 mL/min, ISCO system to give 4-(2-ketoethyl)piperidine-1-carboxylic acid tert-butyl ester (2.8 g, 88.3% yield) as white crystalline powder. MS (ES+) m/z: 172.1 $[M+H-Buten]^+$.

Step 2: To a solution of 4-(2-ketoethyl)piperidine-1-carboxylic acid tert-butyl ester (2.8. g, 12.32 mmol) in THE (72 mL) and cooled to 0° C. Trimethylphenylammonium tribromide (4.72 g, 12.56 mmol) was added portionwise over the course of 20 minutes to give a white suspension. Upon completion, the reaction was quenched with 1M solution of sodium thiosulfate, diluted with diethylether and 1 M $NaHCO_3$. Extract and dry with $Na_2SO_4$, filter and purified via silica gel to provide 4-(1-bromo-2-keto-ethyl)piperidine-1-carboxylic acid tert-butyl ester (2.6 g, 69% yield) as a colorless solid.

Step 3: To a solution of 4-(1-bromo-2-keto-ethyl)piperidine-1-carboxylic acid tert-butyl ester (2.6 g, 8.49 mmol) in EtOH (57 mL) was added thiourea (711 mg, 9.34 mmol) and the mixture was then brought to reflux. Upon completion, the mixture was evaporated to dryness and the residue purified via silica gel yielding 4-(2-aminothiazol-5-yl)piperidine-1-carboxylic acid tert-butyl ester (1.3 g, 54.2% yield) as a white solid. MS (ES+) m/z: 284.4 $[M+H]^+$.

Intermediates 3-16 tert-butyl (3R,4R)-4-(2-aminothiazol-5-yl)-3-fluoro-piperidine-1-carboxylate and tert-butyl (3S,4S)-4-(2-aminothiazol-5-yl)-3-fluoro-piperidine-1-carboxylate

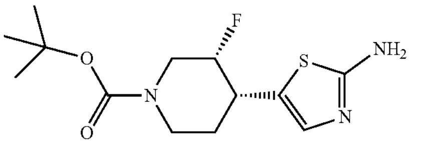

and

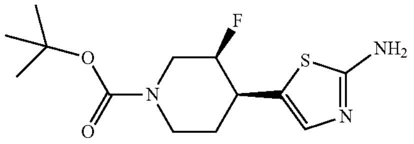

Step 1: Preparation of 4-(2-ethoxy-2-keto-ethylidene)-3-fluoro-piperidine-1-carboxylic acid tert-butyl ester

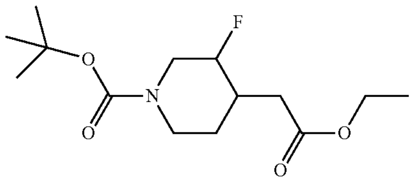 [SMILES: CCOC(=O)CC1CCN(C(=O)OC(C)(C)C)CC1F]

In a flame dried 500 mL 4-necked flask, equipped with a magnetic stirrer bar, dropping funnel and a thermometer, sodium hydride 60% dispersion in mineral oil (2.0 g, 46.0 mmol, 1 eq.) were added portion wise to a solution of triethyl phosphonoacetate (9.8 g, 8.8 mL, 43.7 mmol, 0.950 eq.) in tetrahydrofuran, extra dry (200 mL) over 25 minutes at 0-5° C. The ice-bath was removed and the mixture was stirred for 60 min. 3-fluoro-4-keto-piperidine-1-carboxylic acid tert-butyl ester (10 g, 46.0 mmol, 1 eq.) dissolved in tetrahydrofuran, extra dry (100 mL) was added dropwise over 30 minutes. The reaction was quenched with saturated $NH_4Cl$ solution (160 mL) and then partitioned between water (250 mL) and ethyl acetate (200 mL). The organic layer was separated. The aqueous layer was extracted with one 100-ml portion of ethyl acetate. The combined organic layers were washed with one 200-ml portion of brine, dried over anhydrous sodium sulfate, filtered and concentrated in vacuo. Purification by flash chromatography with heptane/ethyl acetate as eluent gave 4-(2-ethoxy-2-keto-ethylidene)-3-fluoro-piperidine-1-carboxylic acid tert-butyl ester (8.51 g, 64%) as colourless oil. MS (ES+) m/z: 188.0 ($[M+H—C_5H_8O_2]^+$).

Step 2: Preparation of tert-butyl (3SR,4RS)-4-(2-ethoxy-2-oxo-ethyl)-3-fluoro-piperidine-1-carboxylate and tert-butyl (3SR,4SR)-4-(2-ethoxy-2-oxo-ethyl)-3-fluoro-piperidine-1-carboxylate

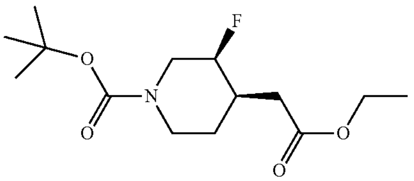

and

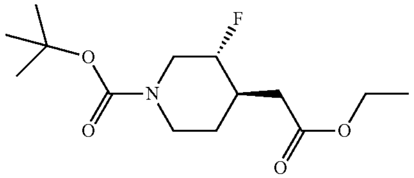

In a 2 L round-bottomed flask, a solution of 4-(2-ethoxy-2-keto-ethylidene)-3-fluoro-piperidine-1-carboxylic acid tert-butyl ester (8.51 g, 29.6 mmol, 1 eq.) in ethyl acetate (567 mL) was degassed by three vacuum/argon cycles. Addition of palladium on charcoal 10% (3.15 g, 2.96 mmol, 0.100 eq.). The reaction mixture was back-filled with hydrogen stirred under a hydrogen atmosphere (1 bar, RT) for 1 h. The catalyst was removed by filtration over a pad of Decalite. The filtrate was evaporated in vacuo. Purification by flash chromatography with methyl tert-butylether/heptane gave tert-butyl (3SR,4SR)-4-(2-ethoxy-2-oxo-ethyl)-3-fluoro-piperidine-1-carboxylate (2.18 g, 25%) as a colourless viscous oil and tert-butyl (3SR,4RS)-4-(2-ethoxy-2-oxo-ethyl)-3-fluoro-piperidine-1-carboxylate (5.87 g, 69%) as a colourless viscous oil.

Step 3: Preparation of (3SR,4SR)-3-Fluoro-4-(2-hydroxyethyl)piperidine-1-carboxylic acid tert-butyl ester

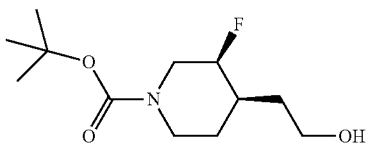 [SMILES: CC(C)(C)OC(=O)N1CC[C@H](CCO)[C@H](F)C1]

In a flame-dried 500 mL four necked flask, equipped with a thermometer and a dropping funnel, (3SR,4RS)-4-(2-ethoxy-2-oxo-ethyl)-3-fluoro-piperidine-1-carboxylate (5.87 g, 20.3 mmol, 1 eq) was dissolved in tetrahydrofuran, extra dry (298 mL). 1 M lithium aluminum hydride in THE (20.3 mL, 20.3 mmol, 1 eq.) was added over 30 minutes at 0-5° C. Stirring was continued for 2 h. The reaction mixture was quenched by subsequent addition of water (0.770 mL), 2M aqueous NaOH (0.770 mL) and water (2.31 mL). The ice-bath was removed and the resulting slurry was stirred overnight. A white precipitate was formed, which was removed by filtration. The filter cake was washed with THF. The filtrate was evaporated to give the crude title compound (4.72 g, 94%) as colorless oil.

Step 4: Preparation of (3SR,4RS)-3-Fluoro-4-(2-ketoethyl)piperidine-1-carboxylic acid tert-butyl ester

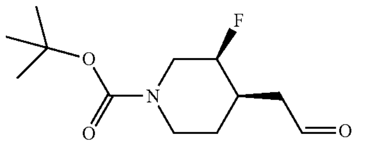 [SMILES: CC(C)(C)OC(=O)N1CC[C@H](CC=O)[C@H](F)C1]

To a solution of (3SR,4RS)-3-Fluoro-4-(2-hydroxyethyl) piperidine-1-carboxylic acid tert-butyl ester (1.83 g, 7.4 mmol, 1 eq.) in dichloromethane (140 mL) was added 1,1,1-tris(acetyloxy)-1,1-dihydro-1,2-benzodioxol-3-(1H)-one (3.14 g, 7.4 mmol, 1 eq.). The reaction mixture was stirred for 5 h at RT. TBME was added. The solids were removed by filtration. The filtrate was concentrated in vacuo. The residue was partitioned between ethyl acetate and water. The layers were separated. The aqueous layer was extracted with two portions of ethyl acetate. The combined organic layers were washed with one portion of brine, dried over anhydrous sodium sulfate and concentrated in vacuo to give the crude title compound (2 g) as white semisolid which was used in the next step without further purification.

Step 5: Preparation of tert-butyl (3SR,4SR)-4-(2-aminothiazol-5-yl)-3-fluoro-piperidine-1-carboxylate

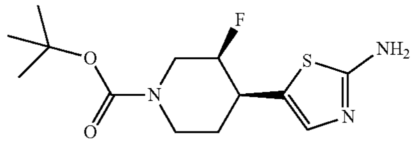 [SMILES: CC(C)(C)OC(=O)N1CC[C@H](c2cnc(N)s2)[C@H](F)C1]

In analogy to intermediate 3-15, steps 2 and 3, from tert-butyl (3SR,4RS)-3-fluoro-4-(2-oxoethyl)piperidine-1-carboxylate, was produced (3SR,4SR)-4-(2-aminothiazol-5-yl)-3-fluoro-piperidine-1-carboxylate (1.22 g, 28% yield) as a white solid. MS (ES+) m/z: 302.1 $[M+H]^+$.

Step 6: Preparation of tert-butyl (3R,4R)-4-(2-aminothiazol-5-yl)-3-fluoro-piperidine-1-carboxylate and tert-butyl (3S,4S)-4-(2-aminothiazol-5-yl)-3-fluoro-piperidine-1-carboxylate

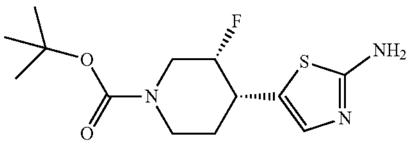

and

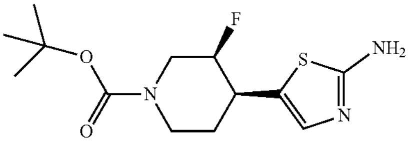

From 1.2 g of (3SR,4SR)-4-(2-aminothiazol-5-yl)-3-fluoro-piperidine-1-carboxylate, using a chiral SFC separation (column: 5 μm, 250*20 mm, chiral amylose-2, and 20% MeOH+0.2% $Et_2NH$) were obtained tert-butyl (3R,4R)-4-(2-aminothiazol-5-yl)-3-fluoro-piperidine-1-carboxylate (MS (ES+) m/z: 302.1 $[M+H]^+$) and tert-butyl (3S,4S)-4-(2-aminothiazol-5-yl)-3-fluoro-piperidine-1-carboxylate (MS (ES+) m/z: 302.1 $[M+H]^+$) separately as off-white solids.

Intermediate 3-17 tert-butyl (3SR,4RS)-4-(2-aminothiazol-5-yl)-3-fluoro-piperidine-1-carboxylate

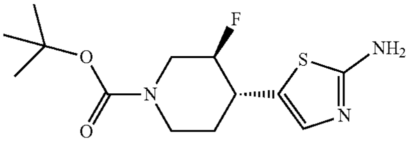 [SMILES: CC(C)(C)OC(=O)N1CC[C@@H](c2cnc(N)s2)[C@H](F)C1]

In analogy to the preparation of the intermediates 3-16, starting from tert-butyl (3SR,4RS)-4-(2-ethoxy-2-oxo-ethyl)-3-fluoro-piperidine-1-carboxylate (obtained in step 2 as intermediate 3-16), the title compound tert-butyl (3SR, 4RS)-4-(2-aminothiazol-5-yl)-3-fluoro-piperidine-1-carboxylate (800 mg) was obtained as an off-white solid. MS (ES+) m/z: 302.2 $[M+H]^+$.

Intermediate 3-18 tert-butyl (7RS)-7-(2-aminothiazol-5-yl)-4-azaspiro [2.5]octane-4-carboxylate

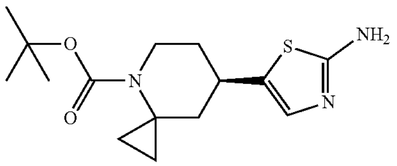 [SMILES: CC(C)(C)OC(=O)N1CC[C@@H](c2cnc(N)s2)CC12CC2]

In analogy to the preparation of the intermediate 3-16, starting from tert-butyl 7-oxo-4-azaspiro[2.5]octane-4-carboxylate, the title compound was prepared tert-butyl (7RS)-7-(2-aminothiazol-5-yl)-4-azaspiro[2.5]octane-4-carboxylate as a white solid. MS (ES+) m/z: 310.2 $[M+H]^+$.

Intermediates 3-19 tert-butyl rac-(1R,5S)-7-(2-aminothiazol-5-yl)-9-oxa-3-azabicyclo[3.3.1]nonane-3-carboxylate and tert-butyl rac-(1S,5R)-7-(2-aminothiazol-5-yl)-9-oxa-3-azabicyclo[3.3.1]nonane-3-carboxylate

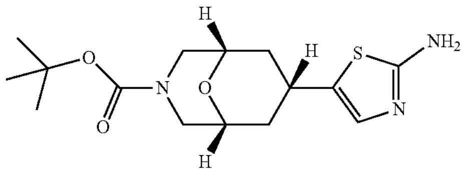

and

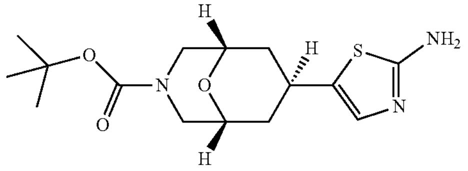

In analogy to the preparation of the intermediate 3-16, starting from tert-butyl 7-oxo-9-oxa-3-azabicyclo[3.3.1] nonane-3-carboxylate, the title compounds were prepared, tert-butyl rac-(1R,5S)-7-(2-aminothiazol-5-yl)-9-oxa-3-azabicyclo[3.3.1]nonane-3-carboxylate and tert-butyl rac-(1S,5R)-7-(2-aminothiazol-5-yl)-9-oxa-3-azabicyclo[3.3.1] nonane-3-carboxylate as a white solid. MS (ES+) m/z: 326.1 $[M+H]^+$.

Intermediate 3-20 benzyl(1S,5R)-6-(2-aminothiazol-5-yl)-3-azabicyclo [3.1.0]hexane-3-carboxylate

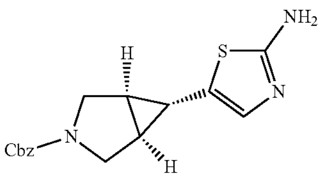 [SMILES: Nc1ncc([C@H]2[C@@H]3CN(C(=O)OCc4ccccc4)C[C@@H]32)s1]

Step 1 (cyclopropanation): In a two-necked round bottom flask 3-pyrroline-1-carboxylic acid benzyl ester (2 g, 9.84 mmol), dissolved in anhydrous $Et_2O$ (20 mL) was treated with Rhodium acetate dimer (22 mg, 0.049 mmol) while stirring at RT. The mixture was then treated over the course of 3 hours with a solution of ethyl diazoacetate (1.53 mL, 14.76 mmol) diluted in anhydrous $Et_2O$ (10 mL), upon addition the mixture was left stirring overnight at RT.

The mixture was diluted with 30 mL $Et_2O$, filtered over Celite and the flow through evaporated first under house vacuum and then under high vacuum. The brown-green residue was taken up in 5 mL $CH_2Cl_2$ loaded onto a 80 g silica cartridge and purified with a gradient of EA in heptane: 5 minutes 100% heptane then linear gradient to 60% EA in 35 minutes, flow 40 mL/min, ISCO system to give (1R,5S)-3-azabicyclo[3.1.0]hexane-3,6-dicarboxylic acid O3-benzyl ester O6-ethyl ester (890 mg, 32% yield) as a yellow oil. The compound is described in: Synlett, 1996 Katherine E. Brighty and Michael J. Castaldi. The second diastereomere (520 mg, 19%) formed was separated during the column chromatography Step 2 (Ester reduction): To a solution of (1R,5S)-3-azabicyclo[3.1.0]hexane-3,6-dicarboxylic acid O3-benzyl ester O6-ethyl ester (890 mg, 3.08 mmol) in anhydrous THF (12 mL) cooled to 0° C., lithium Borohydride 2M in THF (6.18 mL, 12.30 mmol) was added in three portions upon stirring briefly to RT and then to 65° C. for 16 hours. Upon completion, the reaction was cooled to RT and treated with 7 mL of methanol in a dropwise manner. Gas evolution started upon stirring for 15 minutes. The mixture was cooled to 0° C. and treated carefully with 25 mL of a 1M solution of HCl, diluted with diethylether and extracted. Organic layers were pooled and treated with $Na_2SO_4$, filtered and purified via silica gel to provide 4(1S,5R)-6-methylol-3-azabicyclo[3.1.0]hexane-3-carboxylic acid benzyl ester (580 mg, 77% yield) as a yellow oil. MS (ES+) m/z: non detectable.

Step 3 (alcohol oxidation): To a solution of 4(1S,5R)-6-methylol-3-azabicyclo[3.1.0]hexane-3-carboxylic acid benzyl ester (580 mg, 2.35 mmol) in anhydrous DCM (13 mL) cooled to 0° C., Dess-Martin periodinane was added in three portions (1.19 g, 2.81 mmol) and the mixture was left stirring at the same temperature for 1 hour. Upon completion, the reaction was cooled to RT, diluted with 30 mL of DCM and 25 mL of 1 M $NaHCO_3$, the biphasic mixture was stirred at RT for 10 minutes before adding another 25 mL of 1 M $NaHCO_3$ and extracted. The water layer was further extracted with 50 mL DCM, the combined organic layer was washed with 30 mL water and then brine 2×25 mL, treated with $Na_2SO_4$, filtered and dried under vacuum. The residue was taken up in 1% MeOH in $CH_2Cl_2$, loaded onto a 40 g silica cartridge, and purified with a gradient of EA in heptane (3 minutes 100% heptane, then linear gradient to 100% EA in 7 minutes, continued 100% EA for another 10 minutes; flow 40 mL/min, ISCO system), to give (1R,5S)-6-formyl-3-azabicyclo[3.1.0]hexane-3-carboxylic acid benzyl ester (550 mg, 91% yield) as a colorless oil. MS (ES+) m/z: non detectable.

Step 4 (Wittig homologation): (Methoxymethyl)triphenylphosphonium chloride (3.4 g, 9.86 mmol) was suspended in 5 mL of anhydrous THF under Argon atmosphere and the suspension cooled to −78° C. Upon stirring for 10 minutes, a 2 M solution of NaHMDS in THF (5.30 mL, 10.65 mmol) was added to the Wittig salt in a dropwise manner. The resulting orange paste was stirred at −78° C. for 1.5 hours and then treated with a solution of (1R,5S)-6-formyl-3-azabicyclo[3.1.0]hexane-3-carboxylic acid benzyl ester (550 mg, 2.13 mmol) in 5 mL anhydrous THF. The resulting thick suspension was brought to RT and stirred for 1.5 hours. Upon completion, the reaction was diluted with 30 mL of EA, cooled to 0° C. treated with 25 mL water and stirred for 15 minutes. Upon warming to RT, the mixture is separated and the aqueous layer is extracted with 2×30 mL EA, the combined organic was washed with 20 mL water and then 20 mL brine, treated with $Na_2SO_4$, filtered and dried under vacuum. The residue is taken up in $CH_2Cl_2$, loaded onto a 40 g silica cartridge and purified with a gradient of EA in heptane: 3 minutes 100% heptane then linear gradient to 80% EA in 17 minutes, flow 30 mL/min, ISCO system to give (1S,5R)-6-[(E)-2-methoxyvinyl]-3-azabicyclo[3.1.0]hexane-3-carboxylic acid benzyl ester (370 mg, 64% yield) as a colorless oil. 1H NMR shows a 3:1 mixture of geometric isomers.

Step 5 (Enol ether hydrolysis): To a solution of (1S,5R)-6-[(E)-2-methoxyvinyl]-3-azabicyclo[3.1.0]hexane-3-carboxylic acid benzyl ester (650 mg, 2.38 mmol) in reagent grade Acetone (15 mL) cooled to 0° C., 4 mL of 25% w/vol aqueous HCl were added dropwise and the mixture left stirring at the same temperature for 30 minutes. Upon completion, the mixture was poured into 50 mL of $NaHCO_{3(sat)}$, diluted with 75 mL EA, stirred for 15 minutes and extracted. The organic layer was washed with 30 mL of $NaHCO_{3(sat)}$ and then 30 mL brine, treated with $Na_2SO_4$, filtered and dried under vacuum. The residue was taken up in 8 mL $CH_2Cl_2$, loaded onto a 40 g silica cartridge and purified with a gradient of EA in heptane (3 minutes 100% heptane, then linear gradient to 80% EA in 17 minutes, continued with 80% EA for another 5 minutes; flow 35 mL/min, ISCO system) to give (1R,5S)-6-(2-ketoethyl)-3-azabicyclo[3.1.0]hexane-3-carboxylic acid benzyl ester (570 mg, 93% yield) as a colorless oil.

Step 6 (α-chlorination/thiazole formation): To a solution of (1R,5S)-6-(2-ketoethyl)-3-azabicyclo[3.1.0]hexane-3-carboxylic acid benzyl ester (570 mg, 2.20 mmol) in anhydrous DCM (6 mL) cooled to 0° C., N-Chlorosuccinimide was added in one portion (308 mg, 2.31 mmol). The mixture is stirred at the same temperature for 10 minutes before being treated with L-Proline (50.6 mg, 0.44 mmol), the resulting suspension is stirred at 0° C. for 15 minutes then brought to RT and stirred for 3 hours. Upon completion, the reaction was quenched with 25 mL of 0.1 M $NaHCO_3$, the mixture separated and the DCM layer treated with $Na_2SO_4$, filtered and dried under vacuum.

The crude chloro-aldehyde residue was taken up in anhydrous Me-THF (10 mL), treated with water (800 μL, 44 mmol), N-methylmorpholine (360 μL, 3.3 mmol), thiourea (670 mg, 8.8 mmol), and the mixture heated to 84° C. with vigorous stirring. Upon overnight stirring, the mixture was cooled to RT, diluted with 50 mL of Me-THF and 30 mL water, extracted and the organic layer back washed with a second portion of water (30 mL). The organic layer was dried in vacuo and the yellow residue taken up in 6 mL DCM (precipitation occurs), treated with 1 mL 7N ammonia in MeOH and loaded onto a 40 g silica cartridge and purified with a gradient of MeOH in DCM: 5 minutes 100% DCM then linear gradient to 20% MeOH in 25 minutes, flow 40 mL/min, ISCO system to give (1R,5S)-6-(2-aminothiazol-5-yl)-3-azabicyclo[3.1.0]hexane-3-carboxylic acid benzyl ester (320 mg, 46% yield) as a yellow powder. MS (ES+) m/z: 316.2 [$(M+H)^+$].

Synthesis of Intermediates 5

Intermediate 5-1 tert-butyl 4-[5-oxo-7-(p-tolylsulfonyloxy)thiazolo[3,2-a]pyrimidin-2-yl]piperazine-1-carboxylate

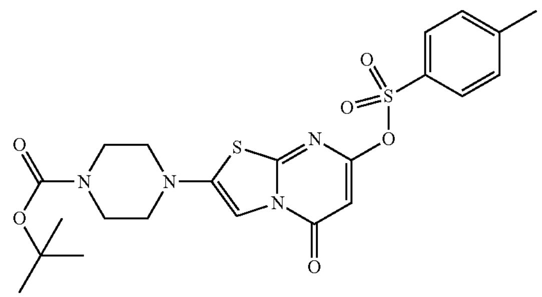 [SMILES: Cc1ccc(S(=O)(=O)Oc2cc(=O)n3cc(N4CCN(C(=O)OC(C)(C)C)CC4)sc3n2)cc1]

Step 1: Preparation of tert-butyl 4-(7-hydroxy-5-oxo-thiazolo[3,2-a]pyrimidin-2-yl)piperazine-1-carboxylate A suspension of 4-(2-aminothiazol-5-yl)piperazine-1-carboxylic acid tert-butyl ester (intermediate 3-1, 3.30 g, 11.6 mmol) and commercially available malonic acid bis(2,4,6-trichlorophenyl) ester (5.37 g, 11.6 mmol) in toluene was heated at reflux for 2 h. The reaction mixture was allowed to return to RT and stirred for 1 h. The resulting suspension was collected by filtration, washed with three 10-mL portions of toluene and dried in vacuo to give the title compound (3.38 g, 83%) as light brown solid. MS (ES+) m/z: 353.2 [$(M+H)^+$].

Step 2: Preparation of tert-butyl 4-[5-oxo-7-(p-tolylsulfonyloxy)thiazolo[3,2-a]pyrimidin-2-yl]piperazine-1-carboxylate To a solution of tert-butyl 4-(7-hydroxy-5-oxo-thiazolo[3,2-a]pyrimidin-2-yl)piperazine-1-carboxylate (3.38 g, 9.59 mmol) and $Et_3N$ (1.94 g, 2.67 mL, 19.18 mmol) in $CH_2Cl_2$ (96 mL) was added p-toluenesulfonyl chloride (2.19 g, 11.51 mmol) at RT and stirred for 16 h. The mixture was washed successively with a 200-mL solution of 2% aqueous HCl, a 200-ml solution of 2% aqueous sodium hydroxide followed by 200 mL of water. The organic layer was directly concentrated in vacuo. The residue was triturated in warm ethyl acetate/n-heptane (2:1, 75 ml). The precipitate was collected by filtration, washed with three 25 ml-portions of ethyl acetate/n-heptane (2:1) and dried in vacuo to give the title compound (3.87 g, 80%) as light brown solid. MS (ES+) m/z: 507.3 [$(M+H)^+$].

Intermediate 5-2 tert-butyl 4-[5-oxo-7-(p-tolylsulfonyloxy)thiazolo[3,2-a]pyrimidin-2-yl]-3,6-dihydro-2H-pyridine-1-carboxylate

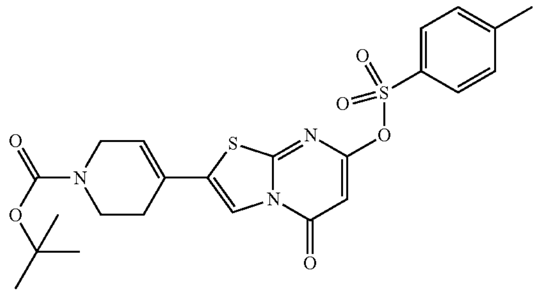 [SMILES: Cc1ccc(S(=O)(=O)Oc2cc(=O)n3cc(C4=CCN(C(=O)OC(C)(C)C)CC4)sc3n2)cc1]

In analogy to the preparation of the intermediate 5-1, from tert-butyl 4-(2-aminothiazol-5-yl)-3,6-dihydro-2H-pyridine-1-carboxylate (intermediate 3-2) was prepared the title compound (120 mg) as a white solid. MS (ES+) m/z: 504.2 [(M+H)+].

Intermediate 5-3 tert-butyl 2,2-dimethyl-4-[5-oxo-7-(p-tolylsulfonyloxy)thiazolo[3,2-a]pyrimidin-2-yl]piperazine-1-carboxylate

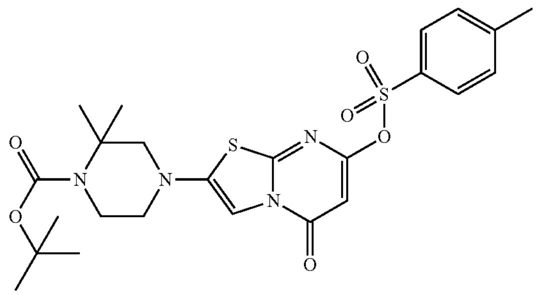 [SMILES: Cc1ccc(S(=O)(=O)Oc2cc(=O)n3cc(N4CCN(C(=O)OC(C)(C)C)C(C)(C)C4)sc3n2)cc1]

In analogy to the preparation of the intermediate 5-1, from tert-butyl 4-(2-aminothiazol-5-yl)-2,2-dimethyl-piperazine-1-carboxylate (intermediate 3-3) was prepared the title compound (600 mg) as an orange solid. MS (ES+) m/z: 535.3 [(M+H)+].

Intermediate 5-4 tert-butyl 7-[5-oxo-7-(p-tolylsulfonyloxy)thiazolo[3,2-a]pyrimidin-2-yl]-4,7-diazaspiro[2.5]octane-4-carboxylate

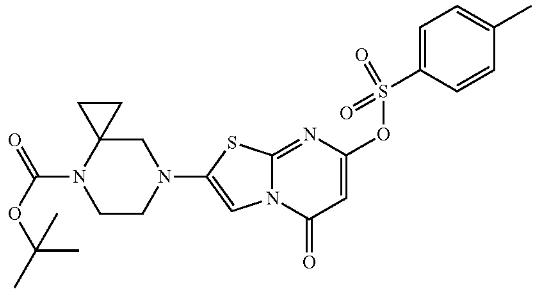 [SMILES: Cc1ccc(S(=O)(=O)Oc2cc(=O)n3cc(N4CCN(C(=O)OC(C)(C)C)C5(CC5)C4)sc3n2)cc1]

In analogy to the preparation of the intermediate 5-1, from tert-butyl 7-(2-aminothiazol-5-yl)-4,7-diazaspiro[2.5]octane-4-carboxylate (intermediate 3-4) was prepared the title compound (300 mg) as an orange solid. MS (ES+) m/z: 533.3 [(M+H)+].

Intermediate 5-5 tert-butyl (2S)-2-methyl-4-[5-oxo-7-(p-tolylsulfonyloxy)thiazolo[3,2-a]pyrimidin-2-yl]piperazine-1-carboxylate

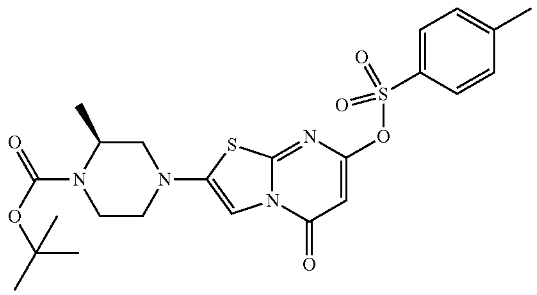 [SMILES: Cc1ccc(S(=O)(=O)Oc2cc(=O)n3cc(N4CCN(C(=O)OC(C)(C)C)[C@@H](C)C4)sc3n2)cc1]

In analogy to the preparation of the intermediate 5-1, from tert-butyl (2S)-4-(2-aminothiazol-5-yl)-2-methyl-piperazine-1-carboxylate (intermediate 3-5) was prepared the title compound (469 mg) as a brown solid. MS (ES+) m/z: 521.3 [(M+H)+].

Intermediate 5-6 tert-butyl (2R)-2-methyl-4-[5-oxo-7-(p-tolylsulfonyloxy)thiazolo[3,2-a]pyrimidin-2-yl]piperazine-1-carboxylate

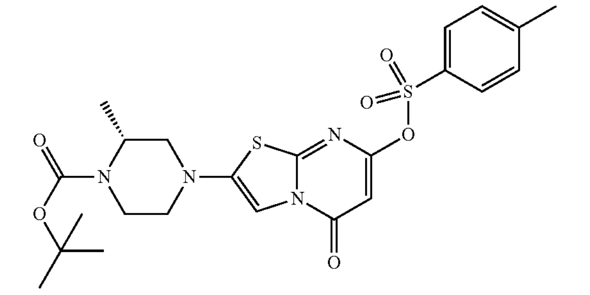 [SMILES: Cc1ccc(S(=O)(=O)Oc2cc(=O)n3cc(N4CCN(C(=O)OC(C)(C)C)[C@H](C)C4)sc3n2)cc1]

In analogy to the preparation of the intermediate 5-1, from tert-butyl (2R)-4-(2-aminothiazol-5-yl)-2-methyl-piperazine-1-carboxylate (intermediate 3-6) was prepared the title compound (410 mg) as an orange solid. MS (ES+) m/z: 521.3 [(M+H)$^+$].

Intermediate 5-7 tert-butyl 2,6-dimethyl-4-[5-oxo-7-(p-tolylsulfonyloxy)thiazolo[3,2-a]pyrimidin-2-yl]piperazine-1-carboxylate

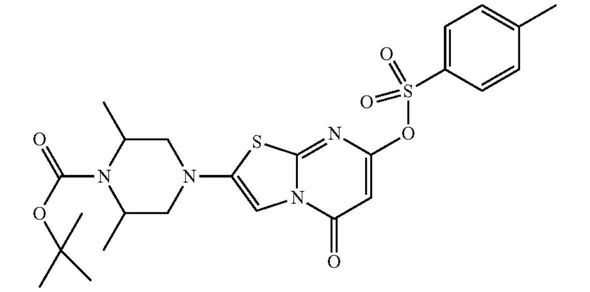 [SMILES: Cc1ccc(S(=O)(=O)Oc2cc(=O)n3cc(N4CC(C)N(C(=O)OC(C)(C)C)C(C)C4)sc3n2)cc1]

In analogy to the preparation of the intermediate 5-1, from tert-butyl 4-(2-aminothiazol-5-yl)-2,6-dimethyl-piperazine-1-carboxylate (intermediate 3-7) was prepared the title compound (160 mg) as an orange solid. MS (ES+) m/z: 535.4 [(M+H)$^+$].

Intermediate 5-8

[5-oxo-2-[(8aS)-3,4,6,7,8,8a-hexahydro-1H-pyrrolo[1,2-a]pyrazin-2-yl]thiazolo[3,2-a]pyrimidin-7-yl] 4-methylbenzenesulfonate

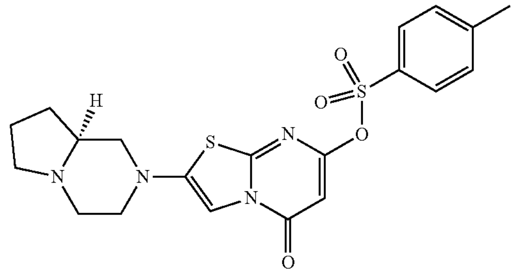 [SMILES: Cc1ccc(S(=O)(=O)Oc2cc(=O)n3cc(N4CCN5CCC[C@H]5C4)sc3n2)cc1]

In analogy to the preparation of the intermediate 5-1, from 5-[(8aS)-3,4,6,7,8,8a-hexahydro-1H-pyrrolo[1,2-a]pyrazin-2-yl]thiazol-2-amine (intermediate 3-8) was prepared the title compound (200 mg) as an orange solid. MS (ES+) m/z: 447.6 [(M+H)$^+$].

Intermediate 5-9 tert-butyl 8-[5-oxo-7-(p-tolylsulfonyloxy)thiazolo[3,2-a]pyrimidin-2-yl]-3,8-diazabicyclo[3.2.1]octane-3-carboxylate

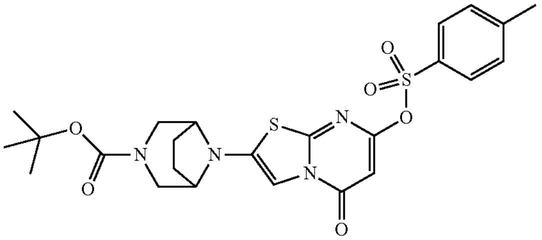 [SMILES: Cc1ccc(S(=O)(=O)Oc2cc(=O)n3cc(N4C5CCC4CN(C(=O)OC(C)(C)C)C5)sc3n2)cc1]

In analogy to the preparation of the intermediate 5-1, from tert-butyl 8-(2-aminothiazol-5-yl)-3,8-diazabicyclo[3.2.1]octane-3-carboxylate (intermediate 3-9) was prepared the title compound (150 mg) as an orange solid. MS (ES+) m/z: 533.4 [(M+H)$^+$].

Intermediate 5-10

[5-oxo-2-[(8aR)-3,4,6,7,8,8a-hexahydro-1H-pyrrolo[1,2-a]pyrazin-2-yl]thiazolo[3,2-a]pyrimidin-7-yl] 4-methylbenzenesulfonate

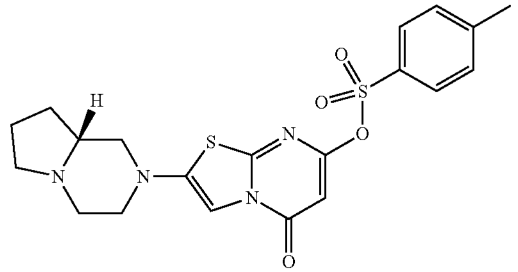 [SMILES: Cc1ccc(S(=O)(=O)Oc2cc(=O)n3cc(N4CCN5CCC[C@@H]5C4)sc3n2)cc1]

In analogy to the preparation of the intermediate 5-1, from 5-[(8aR)-3,4,6,7,8,8a-hexahydro-1H-pyrrolo[1,2-a]pyrazin-2-yl]thiazol-2-amine (intermediate 3-10) was prepared the title compound (150 mg) as an orange solid. MS (ES+) m/z: 447.6 [(M+H)$^+$].

Intermediate 5-11 tert-butyl (1S,4S)-5-[5-oxo-7-(p-tolylsulfonyloxy)thiazolo[3,2-a]pyrimidin-2-yl]-2,5-diazabicyclo[2.2.1]heptane-2-carboxylate

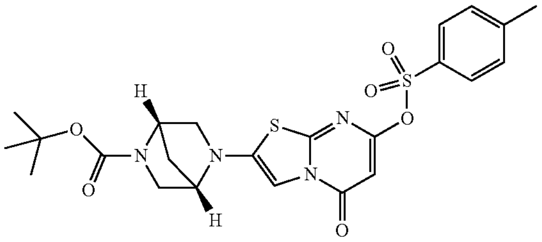 [SMILES: Cc1ccc(S(=O)(=O)Oc2cc(=O)n3cc(N4C[C@@H]5C[C@H]4CN5C(=O)OC(C)(C)C)sc3n2)cc1]

In analogy to the preparation of the intermediate 5-1, from tert-butyl (1S,4S)-5-(2-aminothiazol-5-yl)-2,5-diazabicyclo[2.2.1]heptane-2-carboxylate (intermediate 3-11) was prepared the title compound (316 mg) as a brown solid. MS (ES+) m/z: 519.3 [(M+H)$^+$].

Intermediate 5-12 tert-butyl 2-[5-oxo-7-(p-tolylsulfonyloxy)thiazolo[3,2-a]pyrimidin-2-yl]-1,3,3a,4,6,6a-hexahydropyrrolo[3,4-c]pyrrole-5-carboxylate

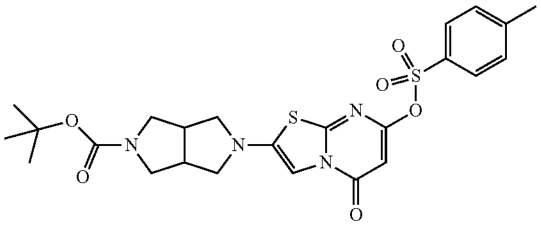 [SMILES: Cc1ccc(S(=O)(=O)Oc2cc(=O)n3cc(N4CC5CN(C(=O)OC(C)(C)C)CC5C4)sc3n2)cc1]

In analogy to the preparation of the intermediate 5-1, from tert-butyl 2-(2-aminothiazol-5-yl)-1,3,3a,4,6,6a-hexahydropyrrolo[3,4-c]pyrrole-5-carboxylate (intermediate 3-12) was prepared the title compound (200 mg) as a brown solid.

Intermediate 5-13

[5-oxo-2-[(3S)-3-pyrrolidin-1-ylpyrrolidin-1-yl]thiazolo[3,2-a]pyrimidin-7-yl] 4-methylbenzenesulfonate

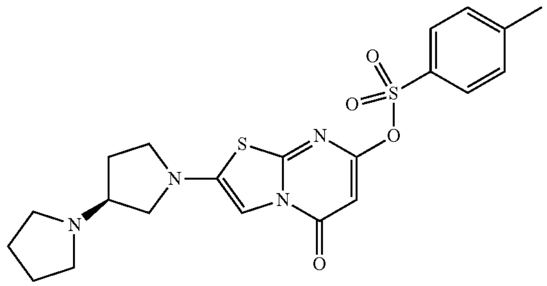 [SMILES: Cc1ccc(S(=O)(=O)Oc2cc(=O)n3cc(N4CC[C@H](N5CCCC5)C4)sc3n2)cc1]

In analogy to the preparation of the intermediate 5-1, from 5-[(3S)-3-pyrrolidin-1-ylpyrrolidin-1-yl]thiazol-2-amine (intermediate 3-13) was prepared the title compound (394 mg) as a brown solid. MS (ES+) m/z: 461.2 [(M+H)$^+$].

Intermediate 5-14 tert-butyl 2-[5-oxo-7-(p-tolylsulfonyloxy)thiazolo[3,2-a]pyrimidin-2-yl]-2,8-diazaspiro-[4.5]decane-8-carboxylate

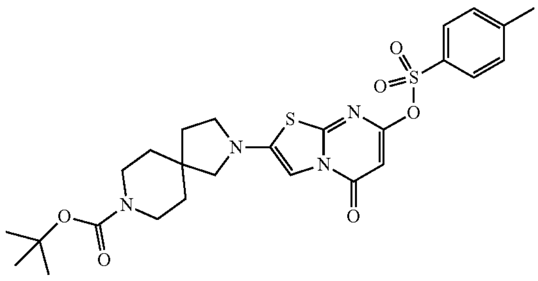 [SMILES: Cc1ccc(S(=O)(=O)Oc2cc(=O)n3cc(N4CCC5(CCN(C(=O)OC(C)(C)C)CC5)C4)sc3n2)cc1]

In analogy to the preparation of the intermediate 5-1, from tert-butyl 2-(2-aminothiazol-5-yl)-2,8-diazaspiro[4.5]decane-8-carboxylate (intermediate 3-14) was prepared the title compound (118 mg) as a brown solid. MS (ES+) m/z: 561.3 [(M+H)$^+$].

Intermediate 5-15 tert-butyl 4-[5-oxo-7-(p-tolylsulfonyloxy)thiazolo[3,2-a]pyrimidin-2-yl]piperidine-1-carboxylate

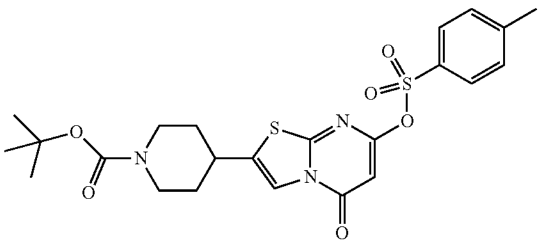 [SMILES: Cc1ccc(S(=O)(=O)Oc2cc(=O)n3cc(C4CCN(C(=O)OC(C)(C)C)CC4)sc3n2)cc1]

In analogy to the preparation of the intermediate 5-1, from tert-butyl 4-(2-aminothiazol-5-yl)piperidine-1-carboxylate (intermediate 3-15) was prepared the title compound (100 mg) as a brown solid. MS (ES+) m/z: 506.4 [(M+H)$^+$].

Intermediate 5-16 tert-butyl 4-hydroxy-4-[5-oxo-7-(p-tolylsulfonyloxy)thiazolo[3,2-a]pyrimidin-2-yl]piperidine-1-carboxylate

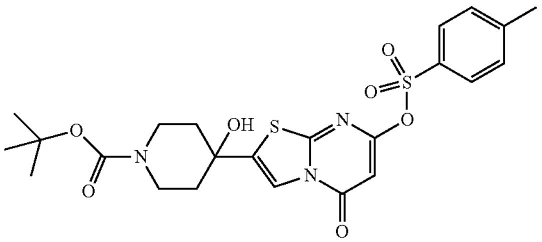 [SMILES: Cc1ccc(S(=O)(=O)Oc2cc(=O)n3cc(C4(O)CCN(C(=O)OC(C)(C)C)CC4)sc3n2)cc1]

In analogy to the preparation of the intermediate 5-1, from tert-butyl 4-(2-aminothiazol-5-yl)-4-hydroxy-piperidine-1-carboxylate (which can be prepared in analogy to intermediate 3-2) was prepared the title compound (310 mg) as a white solid. MS (ES+) m/z: 522.2 [(M+H)$^+$].

Intermediates 5-17 tert-butyl (3R,4R)-3-fluoro-4-[5-oxo-7-(p-tolylsulfonyloxy)thiazolo[3,2-a]pyrimidin-2-yl]piperidine-1-carboxylate and tert-butyl (3S,4S)-3-fluoro-4-[5-oxo-7-(p-tolylsulfonyloxy)thiazolo[3,2-a]pyrimidin-2-yl]piperidine-1-carboxylate

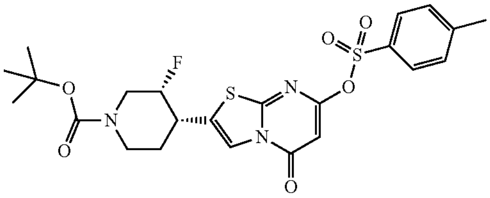

and

-continued

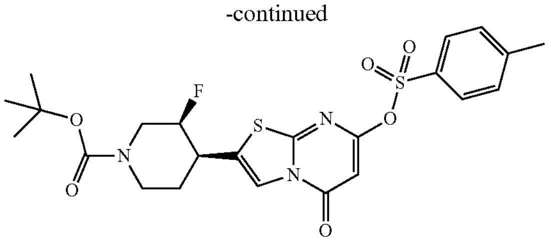

In analogy to the preparation of the intermediate 5-1, the title compounds were separately prepared as an off-white solid from tert-butyl (3R,4R)-4-(2-aminothiazol-5-yl)-3-fluoro-piperidine-1-carboxylate and tert-butyl (3S,4S)-4-(2-aminothiazol-5-yl)-3-fluoro-piperidine-1-carboxylate respectively (intermediates 3-16). MS (ES+) m/z: 524.2 [(M+H)$^+$] for each enantiomer.

Intermediates 5-18 tert-butyl (3S,4R)-3-fluoro-4-[5-oxo-7-(p-tolylsulfonyloxy)thiazolo[3,2-a]pyrimidin-2-yl]piperidine-1-carboxylate and tert-butyl (3R,4S)-3-fluoro-4-[5-oxo-7-(p-tolylsulfonyloxy)thiazolo[3,2-a]pyrimidin-2-yl]piperidine-1-carboxylate

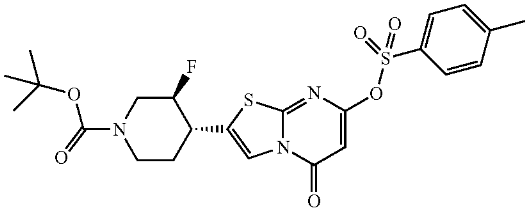

and

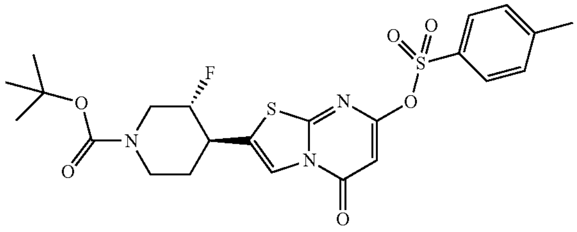

Step 1: In analogy to the preparation of the intermediate 5-1, from tert-butyl (3SR,4RS)-4-(2-aminothiazol-5-yl)-3-fluoro-piperidine-1-carboxylate (intermediates 3-17) was produced tert-butyl (3SR,4RS)-3-fluoro-4-[5-oxo-7-(p-tolylsulfonyloxy)thiazolo[3,2-a]pyrimidin-2-yl]piperidine-1-carboxylate (155 mg) as an off-white solid.

Step 2: This racemic mixture was subjected to a chiral SFC separation (column: 5 μm, 250*20 mm, chiral IB column, 25% MeOH) yielding tert-butyl (3S,4R)-3-fluoro-4-[5-oxo-7-(p-tolylsulfonyloxy)thiazolo[3,2-a]pyrimidin-2-yl]piperidine-1-carboxylate and tert-butyl (3R,4S)-3-fluoro-4-[5-oxo-7-(p-tolylsulfonyloxy)thiazolo[3,2-a]pyrimidin-2-yl]piperidine-1-carboxylate (68 and 66 mg). MS (ES+) m/z: 524.2 [(M+H)$^+$] for each enantiomer.

Intermediates 5-19 tert-butyl (7S)-7-[5-oxo-7-(p-tolylsulfonyloxy)thiazolo[3,2-a]pyrimidin-2-yl]-4-azaspiro[2.5]octane-4-carboxylatecarboxylate and tert-butyl (7R)-7-[5-oxo-7-(p-tolylsulfonyloxy)thiazolo[3,2-a]pyrimidin-2-yl]-4-azaspiro[2.5]octane-4-carboxylatecarboxylate

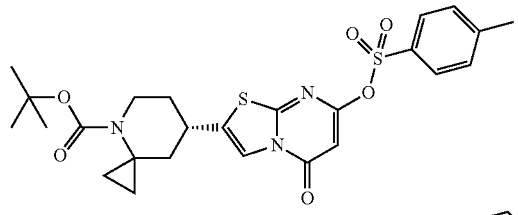

and

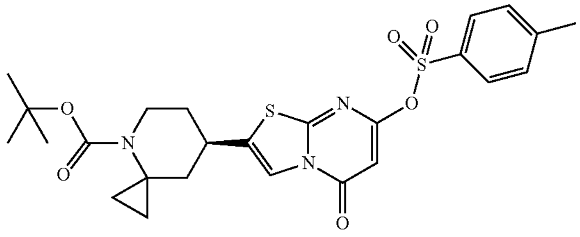

Step 1: In analogy to the preparation of the intermediate 5-1, from racemic tert-butyl 7-(2-aminothiazol-5-yl)-4-azaspiro[2.5]octane-4-carboxylate (intermediate 3-18) was prepared the racemic tert-butyl (7)-7-[5-oxo-7-(p-tolylsulfonyloxy)thiazolo[3,2-a]pyrimidin-2-yl]-4-azaspiro[2.5]octane-4-carboxylatecarboxylate (133 mg) as a white solid. MS (ES+) m/z: 532.2 [(M+H)$^+$]

Step 2: The two enantiomeric title compounds have further been separated by chiral SFC (chiral AD-H column, 5 μm, 250*20 mm, 45% MeOH+0.2% $Et_2NH$) yielding tert-butyl (7S)-7-[5-oxo-7-(p-tolylsulfonyloxy)thiazolo[3,2-a]pyrimidin-2-yl]-4-azaspiro[2.5]octane-4-carboxylatecarboxylate and tert-butyl (7R)-7-[5-oxo-7-(p-tolylsulfonyloxy)thiazolo[3,2-a]pyrimidin-2-yl]-4-azaspiro[2.5]octane-4 carboxylatecarboxylate as white solids. MS (ES+) m/z: 532.2 [(M+H)$^+$] for each enantiomer.

Intermediates 5-20 tert-butyl rac-(1R,5S)-7-[5-oxo-7-(p-tolylsulfonyloxy)thiazolo[3,2-a]pyrimidin-2-yl]-9-oxa-3-azabicyclo[3.3.1]nonane-3-carboxylate and tert-butyl rac-(1S,5R)-7-[5-oxo-7-(p-tolylsulfonyloxy)thiazolo[3,2-a]pyrimidin-2-yl]-9-oxa-3-azabicyclo[3.3.1]nonane-3-carboxylate

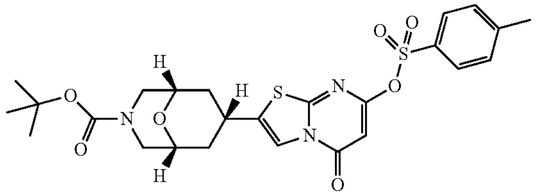

and

-continued

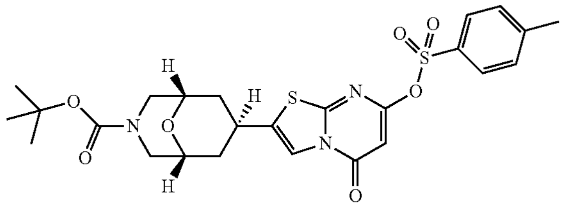

In analogy to the preparation of intermediates 5-1, from intermediates 3-19 the title compounds were prepared (2.14 g) as a white foam. MS (ES+) m/z: 548.2 [(M+H)$^+$].

Intermediates 5-21

(1R,5S)-6-(5-keto-7-tosyloxy-thiazolo[3,2-a]pyrimidin-2-yl)-3-azabicyclo[3.1.0]hexane-3-carboxylic acid benzyl ester

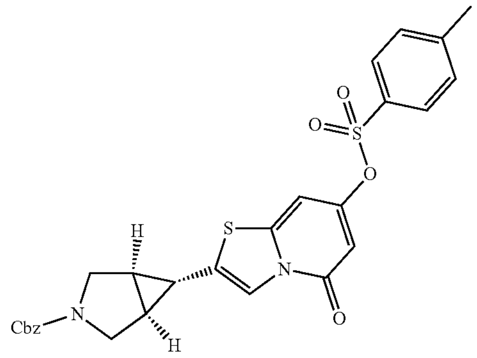 [SMILES: Cc1ccc(S(=O)(=O)Oc2cc(=O)n3cc([C@H]4[C@@H]5CN(C(=O)OCc6ccccc6)C[C@@H]54)sc3c2)cc1]

In analogy to the preparation of the intermediate 5-1, from benzyl(1S,5R)-6-(2-aminothiazol-5-yl)-3-azabicyclo[3.1.1]hexane-3-carboxylate (intermediate 3-20) was prepared the title compound (280 mg) as a white solid. MS (ES+) m/z: 538.2 [(M+H)$^+$].

Preparation of boronic esters 6

Boronic ester 6-1

2,8-dimethyl-6-(4,4,5,5-tetramethyl-1,3,2-dioxaborolan-2-yl)imidazo[1,2-b]pyridazine

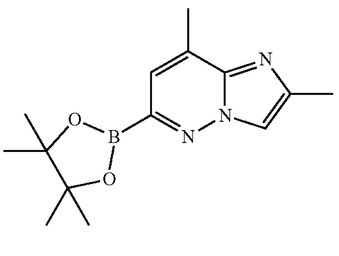

Boronic ester 6-1 can be prepared according to WO2019/057740

Boronic ester 6-2

4-fluoro-2-methyl-6-(4,4,5,5-tetramethyl-1,3,2-dioxaborolan-2-yl)-1,3-benzoxazole

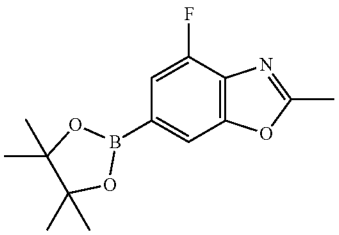

Boronic ester 6-2 can be prepared according to WO2013/119916

Boronic ester 6-3

2-methyl-6-(4,4,5,5-tetramethyl-1,3,2-dioxaborolan-2-yl)imidazo[1,2-b]pyridazine

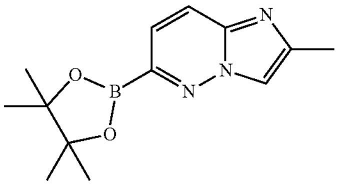

Boronic ester 6-3 can be prepared according to WO2015/173181

Boronic ester 6-4

2-methyl-6-(4,4,5,5-tetramethyl-1,3,2-dioxaborolan-2-yl)-8-(trifluoromethyl)imidazo[1,2-b]pyridazine

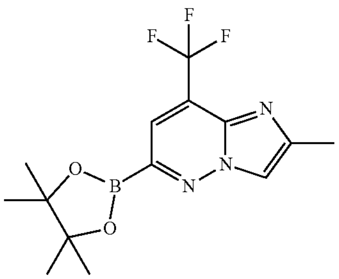

Step 1: Preparation of 6-chloro-2-methyl-8-(trifluoromethyl)imidazo[1,2-b]pyridazine In a 10 mL round bottom flask, equipped with a magnetic stirrer bar, reflux condenser and N2-inlet bubbler, [6-chloro-4-(trifluoromethyl)pyridazin-3-yl]amine (94 mg, 0.476 mmol) and pyridinium p-toluene sulfonate (11.9 mg, 0.048 mmol) were combined with isopropanol (2 mL). 1-bromo-2,2-dimethoxy-propane (104.51 mg, 77.13 uL, 0.571 mmol, 1.2 eq.) was added and the colorless solution was stirred 24 hours at 75° C. The resulting dark-brown reaction mixture was cooled to RT, diluted with EtOAc (10 mL) and washed with a saturated aqueous $NaHCO_3$-solution (10 mL). Organic layer was separated and dried over sodium sulfate, filtered off and concentrated in vacuo. The crude (120 mg brownish viscous oil) was purified by column chromatography yielding 6-chloro-2-methyl-8-(trifluoromethyl)imidazo[1,2-b]pyridazine (46 mg, 34% yield) as light yellow solid. MS (ES+) m/z: 236.1 [(M+H)$^+$].

Step 2: Preparation of 2-methyl-6-(4,4,5,5-tetramethyl-1,3,2-dioxaborolan-2-yl)-8-(trifluoromethyl)imidazo[1,2-b]pyridazine In a dry/Argon flushed 20 mL microwave tube with a magnetic stirrer bar and a cap-septum, 6-chloro-2-methyl-8-(trifluoromethyl)imidazo[1,2-b]pyridazine (300 mg, 1.2 mmol), bis(pinacolato)diboron (364.7 mg, 1.44 mmol) and potassium acetate (352.42 mg, 3.59 mmol) were combined with 1,4-dioxane (12 mL). The yellowish fine suspension was stirred and degassed with Argon for 10-15 min. before tetrakis(triphenylphosphine)palladium (69.1 mg, 0.060 mmol) was added. The vial was sealed and stirred in a heating block (Temp: 100° C.) for 22 hours. Further addition of tetrakis(triphenylphosphine)palladium (69 mg, 0.060 mmol), after 90 minutes, 3.5 hrs and 6 hrs. The reaction was cooled to room temperature, filtered off and concentrated in vacuo. The amber viscous oil was purified by column chromatography to give 2-methyl-6-(4,4,5,5-tetramethyl-1,3,2-dioxaborolan-2-yl)-8-(trifluoromethyl)imidazo[1,2-b]pyridazine (428 mg, 48%) as yellow viscous oil.

Boronic ester 6-5

8-ethyl-2-methyl-6-(4,4,5,5-tetramethyl-1,3,2-dioxaborolan-2-yl)imidazo[1,2-b]pyridazine

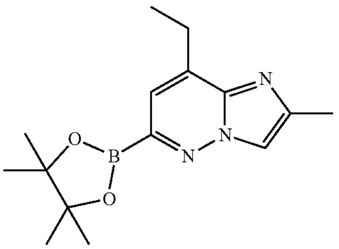

Step 1: Preparation of 8-bromo-6-chloro-2-methylimidazo[1,2-b]pyridazine

To a solution of (4-bromo-6-chloro-pyridazin-3-yl)amine (2000 mg, 9.6 mmol) and PPTS (241 mg, 0.96 mmol) in isopropanol (19 mL) was added 1-bromo-2,2-dimethoxy-propane (2.11 g, 1.56 mL, 11.5 mmol) at RT. The reaction mixture was heated at reflux for 30 h. After cooling down to RT, the mixture was partitioned between ethyl acetate (50 ml) and 1M $Na_2CO_3$ sol (30 ml). The layers were separated, and the organic layer was washed with one 30-ml portion of brine and dried over sodium sulfate, filtered and concentrated in vacuo to give the crude title compound (2.37 g, 92% yield) as light brown solid with a purity of 92%, which was used without further purification. MS (ES+) m/z: 246.0-248.0 [$(M+H)^+$].

Step 2: Preparation of 6-chloro-8-ethyl-2-methyl-imidazo[1,2-b]pyridazine

To a solution of 8-bromo-6-chloro-2-methyl-imidazo[1,2-b]pyridazine (300 mg, 1.22 mmol) and 1.5 M diethylzine (811 uL, 1.2 mmol) in tetrahydrofuran (4.9 mL) was added palladiumtetrakis (70 mg, 0.061 mmol) at RT and stirred for 20 min. The mixture was partitioned between ethyl acetate (30 mL) and 1M $Na_2CO_3$ sol (30 mL). The combined organic layer was washed with one 30-ml portion of brine dried over sodium sulfate, filtered concentrated in vacuo. Purification by flash chromatography gave 6-chloro-8-ethyl-2-methyl-imidazo[1,2-b]pyridazine (97 mg; 34% yield) as a white solid. MS (ES+) m/z: 196.0 [$(M+H)^+$].

Step 3: Preparation of 8-ethyl-2-methyl-6-(4,4,5,5-tetramethyl-1,3,2-dioxaborolan-2-yl)imidazo[1,2-b]pyridazine To a mixture of 6-chloro-2-methyl-imidazo[1,2-b]pyridazine (100 mg, 0.597 mmol), bis(pinacolato)diboron (151.5 mg, 0.597 mmol, 1 eq.) and potassium acetate (150.48 mg, 1.53 mmol) in 1,4-dioxane (1.2 mL) was added of XPhos PdG4 (22 mg, 0.026 mmol). The reaction mixture was heated at 100° C. for 1 h. The reaction mixture was cooled to RT and diluted with ethyl acetate (5-10 mL). The solids were removed by filtration. The filtrate was concentrated in vacuo to give the crude title compound which was used directly in the next step without further purification.

Boronic ester 6-6

8-methoxy-2-methyl-6-(4,4,5,5-tetramethyl-1,3,2-dioxaborolan-2-yl)imidazo[1,2-b]pyridazine

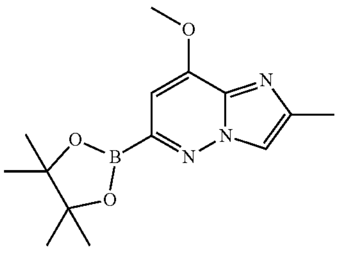

Step 1: Preparation of 6-chloro-8-methoxy-2-methyl-imidazo[1,2-b]pyridazine

To a solution of 8-bromo-6-chloro-2-methyl-imidazo[1,2-b]pyridazine (described herein above, 500 mg, 2.03 mmol) and cesium carbonate (1.4 g, 4.3 mmol) in acetonitrile (10 mL) was added MeOH (400 uL, 9.89 mmol) at RT and stirring was continued for 4 h. The mixture was partitioned between ethyl acetate (30 mL) and water (30 mL). The combined organic layer was washed with one 30-mL portion of brine, dried over sodium sulfate, filtered and concentrated in vacuo. A purification by flash chromatography gave 6-chloro-8-methoxy-2-methyl-imidazo[1,2-b]pyridazine (337 mg; 84% yield) as a white solid. MS (ES+) m/z: 198.0 [$(M+H)^+$].

Step 2: Preparation of 8-methoxy-2-methyl-6-(4,4,5,5-tetramethyl-1,3,2-dioxaborolan-2-yl)imidazo[1,2-b]pyridazine The title compound was prepared from 6-chloro-8-methoxy-2-methyl-imidazo[1,2-b]pyridazine in analogy to the synthesis of the boronic ester 6-5, step 2.

Boronic ester 6-7

8-cyclopropyl-2-methyl-6-(4,4,5,5-tetramethyl-1,3,2-dioxaborolan-2-yl)imidazo[1,2-b]pyridazine

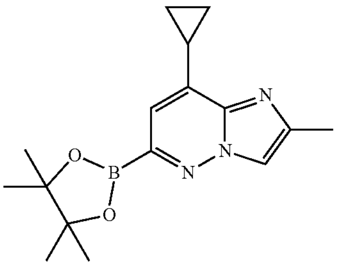

Step 1: Preparation of 6-chloro-8-cyclopropyl-2-methyl-imidazo[1,2-b]pyridazine

A mixture of 8-bromo-6-chloro-2-methyl-imidazo[1,2-b]pyridazine (prepared herein above, 300 mg, 1.2 mmol), cyclopropylboronic acid (209 mg, 2.43 mmol) and $Na_2CO_3$ (387 mg, 3.65 mmol) in 1,4-dioxane (4.9 mL) and water (1.2 mL) was degassed by three vacuum/argon cycles followed by the addition of 1,1'-bis(diphenylphosphino)ferrocenedichloro palladium(II) dichloromethane complex (90.2 mg, 0.122 mmol). The reaction mixture was heated at 90° C. and stirred over the weekend under an atmosphere of argon. Another portion of cyclopropylboronic acid (209 mg, 2.43 mmol) was added. The mixture was partitioned between ethyl acetate (50 mL) and an aqueous 1M solution of $NaHCO_3$ sol (50 ml). The organic layer was washed with one 50-mL portion of brine, dried over sodium sulfate, filtered and concentrated in vacuo. A purification by flash chromatography gave 6-chloro-8-cyclopropyl-2-methyl-imidazo[1,2-b]pyridazine (64 mg, 15% yield) as light brown solid with a purity of 61%. MS (ES+) m/z: 208.0 [$(M+H)^+$].

Step 2: Preparation of 8-cyclopropyl-2-methyl-6-(4,4,5,5-tetramethyl-1,3,2-dioxaborolan-2-yl)imidazo[1,2-b]pyridazine The title compound was prepared from 6-chloro-8-cyclopropyl-2-methyl-imidazo[1,2-b]pyridazine in analogy to the synthesis of the boronic ester 6-5, step 2.

Boronic ester 6-8

8-isopropenyl-2-methyl-6-(4,4,5,5-tetramethyl-1,3,2-dioxaborolan-2-yl)imidazo[1,2-b]pyridazine

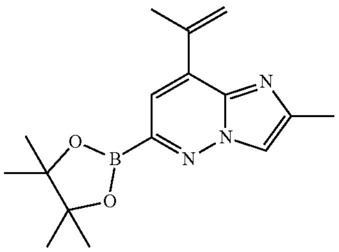

Step 1: Preparation of 6-chloro-8-isopropenyl-2-methyl-imidazo[1,2-b]pyridazine

A mixture of 8-bromo-6-chloro-2-methyl-imidazo[1,2-b]pyridazine (prepared herein above, 300 mg, 1.2 mmol), 2-isopropenyl-4,4,5,5-tetramethyl-1,3,2-dioxaborolane (245 mg, 274 uL, 1.46 mmol) and $K_2CO_3$ (504 mg, 3.65 mmol) in 1,4-dioxane (5.0 mL) and water (1.0 mL) was degassed by three vacuum/argon cycles followed by the addition of 1,1'-bis(diphenylphosphino)ferrocenedichloro palladium(II) dichloromethane complex (90 mg, 0.122 mmol). The reaction mixture was heated at 90° C. and stirred over night under an atmosphere of argon. The mixture was partitioned between ethyl acetate (50 mL) and water (50 mL). The organic layer was washed with one 50-mL portion of brine, dried over sodium sulfate, filtered and concentrated in vacuo. A purification by flash chromatography gave 6-chloro-8-isopropenyl-2-methyl-imidazo[1,2-b]pyridazine (0.180 g, 60% yield) as light brown solid. MS (ES+) m/z: 208.1 $[(M+H)^+]$.

Step 2: 8-isopropenyl-2-methyl-6-(4,4,5,5-tetramethyl-1,3,2-dioxaborolan-2-yl)imidazo[1,2-b]pyridazine The title compound was prepared from 6-chloro-8-isopropenyl-2-methyl-imidazo[1,2-b]pyridazine in analogy to the synthesis of the boronic ester 6-5, step 2.

Boronic ester 6-9

2,7-dimethyl-5-(4,4,5,5-tetramethyl-1,3,2-dioxaborolan-2-yl)oxazolo[5,4-b]pyridine

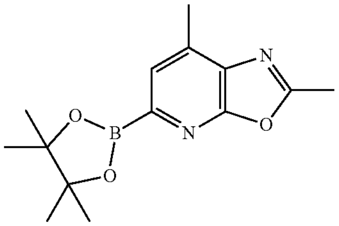

Step 1: Preparation of N-(2,6-dichloro-4-methyl-3-pyridyl)acetamide

To a solution of (2,6-dichloro-4-methyl-3-pyridyl)amine (2000 mg, 11.3 mmol) and $Ac_2O$ (11.53 g, 10.66 mL, 112.98 mmol) was added a catalytical amount of DMAP. The reaction mixture was stirred for 1 h at RT then over night at 60° C. The reaction mixture was cooled to RT, and ethanol (10 mL, 169.46 mmol) was slowly added and stirring continued for 30 min. The solvent were evaporated and residual AcOH was removed by azeotropic distillation with one 30-mL portion of toluene. The residue was triturated in warm ethyl acetate (15 mL). Heptane (15 mL) was added and the suspension was stirred for 1 h. The precipitate was collected by filtration, washed with two 10 mL-portions of ethyl acetate/n-heptane (1:1) and dried in vacuo to give N-(2,6-dichloro-4-methyl-3-pyridyl)acetamide (1750 mg, 71% yield) as brown solid. MS (ES+) m/z: 219.1 $[(M+H)^+]$.

Step 2: Preparation of 5-chloro-2,7-dimethyl-oxazolo[5,4-b]pyridine

To a solution of N-(2,6-dichloro-4-methyl-3-pyridyl)acetamide (1750 mg, 7.99 mmol) in N-methyl-2-pyrrolidinone (16 mL) was added NaH, 55% in oil (348.58 mg, 7.99 mmol) at RT. The reaction mixture was heated at 120° C. and stirred for 20 h. After cooled down to RT, acetic acid (959 mg, 914 uL, 15.98 mmol) was slowly added and stirred for an additional 30 min. The mixture was partitioned between ethyl acetate (50 mL) and 1M $NaHCO_3$ sol (20 mL). The organic layer was washed with one 50-mL portion of water and one 30-mL portion of brine, dried over sodium sulfate, filtered and concentrated in vacuo. A purification by flash chromatography gave 5-chloro-2,7-dimethyl-oxazolo[5,4-b]pyridine (85 mg, 6% yield) as a white solid. MS (ES+) m/z: 183.1 $[(M+H)^+]$.

Step 3: 2,7-dimethyl-5-(4,4,5,5-tetramethyl-1,3,2-dioxaborolan-2-yl)oxazolo[5,4-b]pyridine The title compound was prepared from 5-chloro-2,7-dimethyl-oxazolo[5,4-b]pyridine in analogy to the synthesis of the boronic ester 6-5, step 2.

Boronic ester 6-10

8-isopropyl-2-methyl-6-(4,4,5,5-tetramethyl-1,3,2-dioxaborolan-2-yl)imidazo[1,2-b]pyridazine

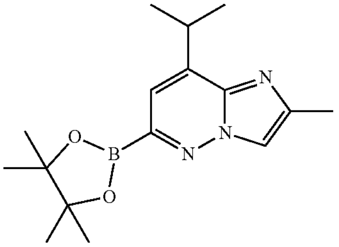

Step 1: Preparation of 6-chloro-8-isopropyl-2-methyl-imidazo[1,2-b]pyridazine

A solution of 6-chloro-8-isopropenyl-2-methyl-imidazo[1,2-b]pyridazine (described as intermediate in the synthesis of the boronic ester 6-8, 150 mg, 0.722 mmol) in ethyl acetate (6 mL) was degassed by three vacuum/argon cycles. Addition of platinum (IV) oxide (16 mg, 0.072 mmol). The reaction mixture was degassed and purged with hydrogen. Stirring was continued for 3 h at RT under an atmosphere of a hydrogen balloon. The reaction mixture was diluted with dichloromethane and filtered over a bed of decalite, then concentrated in vacuo and give 6-chloro-8-isopropyl-2-methyl-imidazo[1,2-b]pyridazine (110 mg, 73% yield) as light yellow oil. MS (ES+) m/z: 210.0 [(M+H)$^+$].

Step 2: 8-isopropyl-2-methyl-6-(4,4,5,5-tetramethyl-1,3,2-dioxaborolan-2-yl)imidazo[1,2-b]pyridazine The title compound was prepared from 6-chloro-8-isopropyl-2-methyl-imidazo[1,2-b]pyridazine in analogy to the synthesis of the boronic ester 6-5, step 2.

Boronic ester 6-11

8-(difluoromethoxy)-2-methyl-6-(4,4,5,5-tetramethyl-1,3,2-dioxaborolan-2-yl)imidazo[1,2-b]pyridazine

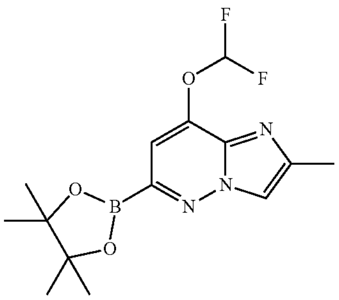

Step 1: Preparation of 6-chloro-2-methyl-imidazo[1,2-b]pyridazin-8-ol

A suspension of (6-chloro-4-methoxy-pyridazin-3-yl)amine (1765 mg, 11.06 mmol), 1-bromo-2,2-dimethoxy-propane (2.23 g, 1.64 mL, 12.17 mmol) and PPTS (278 mg, 1.11 mmol) in isopropanol (22 mL) was heated at reflux for 3 days. After cooling down to RT, the resulting brown suspension was collected by filtration, washed with three 10-mL portions of i-PrOH and dried in vacuo to give 6-chloro-2-methyl-imidazo[1,2-b]pyridazin-8-ol (1.25 g, 54% yield) as brown solid. MS (ES+) m/z: 184.1 [(M+H)$^+$].

Step 2: 6-chloro-8-(difluoromethoxy)-2-methyl-imidazo[1,2-b]pyridazine

To a solution of 6-chloro-2-methyl-imidazo[1,2-b]pyridazin-8-ol (50 mg, 0.272 mmol) and sodium chlorodifluoroacetate (83 mg, 0.545 mmol) in N,N-dimethylformamide (0.91 mL) was added $K_2CO_3$ (113 mg, 0.817 mmol) at RT. The reaction mixture was then heated at 80° C. for 1 h. The reaction mixture was cooled to RT and water added. The organic layer was separated and washed with one 25-ml portion of water and one 25-ml portion of brine, then dried over sodium sulfate, filtered and concentrated in vacuo to give 6-chloro-8-(difluoromethoxy)-2-methyl-imidazo[1,2-b]pyridazine (34 mg, 45% yield) a light brown solid. MS (ES+) m/z: 234.1 [(M+H)$^+$].

Step 3: 8-(difluoromethoxy)-2-methyl-6-(4,4,5,5-tetramethyl-1,3,2-dioxaborolan-2-yl)imidazo [1,2-b] pyridazine The title compound was prepared from 6-chloro-8-(difluoromethoxy)-2-methyl-imidazo[1,2-b]pyridazine in analogy to the synthesis of the boronic ester 6-5, step 2.

Boronic ester 6-12

N-[2-chloro-6-(4,4,5,5-tetramethyl-1,3,2-dioxaborolan-2-yl)-4-(trifluoromethyl)-3-pyridyl]acetamide

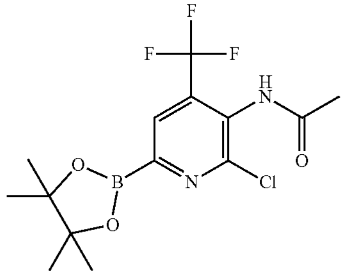 [SMILES: CC(=O)Nc1c(C(F)(F)F)cc(B2OC(C)(C)C(C)(C)O2)nc1Cl]

Step 1: Preparation of N-[2,6-dichloro-4-(trifluoromethyl)-3-pyridyl]acetamide

To a solution of [2,6-dichloro-4-(trifluoromethyl)-3-pyridyl]amine (2.0 g, 8.66 mmol) and AcCl (5.06 g, 4.59 mL, 64.5 mmol) was added $H_2SO_4$ (461 uL, 8.66 mmol) at 0° C. The cooling bath was removed and the reaction stirred for 1 hour. The mixture was poured in crushed ice and stirred. The resulting precipitate was collected by filtration, washed with water and dried in vacuo to give N-[2,6-dichloro-4-(trifluoromethyl)-3-pyridyl]acetamide (2.03 g, 86% yield) as white solid. MS (ES+) m/z: 273.1 [(M+H)$^+$].

Step 2: N-[2-chloro-6-(4,4,5,5-tetramethyl-1,3,2-dioxaborolan-2-yl)-4-(trifluoromethyl)-3-pyridyl] acetamide The title compound was prepared from N-[2,6-dichloro-4-(trifluoromethyl)-3-pyridyl]acetamide in analogy to the synthesis of the boronic ester 6-5, step 2.

Boronic ester 6-13

2-chloro-8-methyl-6-(4,4,5,5-tetramethyl-1,3,2-dioxaborolan-2-yl)imidazo[1,2-b]pyridazine

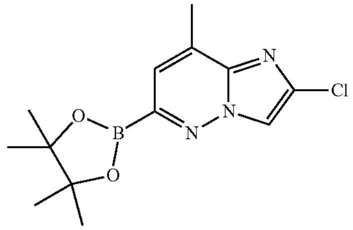 [SMILES: Cc1cc(B2OC(C)(C)C(C)(C)O2)nn2cc(Cl)nc12]

Step 1: Preparation of 6-chloro-8-methyl-imidazo[1,2-b]pyridazin-2-ol

A mixture of 6-chloro-4-methyl-pyridazin-3-amine (1.15 g, 8.0 mmol), methyl bromoacetate (1.35 g, 8.8 mmol) and PPTS (0.200 g, 0.80 mmol) in 1-butanol (26 mL) was heated at reflux for 6 hours. After cooling down to RT, the resulting suspension was collected by filtration, washed with iPrOH and dried under vacuo, yielding the title product (730 mg, 47% yield) as a light green solid. MS (ES+) m/z: 184.1 $[(M+H)^+]$.

Step 2: Preparation of 2,6-dichloro-8-methyl-imidazo[1,2-b]pyridazine 6-chloro-8-methyl-imidazo[1,2-b]pyridazin-2-ol (663 mg, 3.6 mmol) in $POCl_3$ (6.7 mL, 72.2 mmol) was heated at reflux for 24 hours. After cooling down to RT, the volatiles were removed under vacuo, and the residue partioned between EtOAc and an aqueous saturated solution of $NaHCO_3$. The organic phase was collected, washed with brine, dried over $Na_2SO_4$ and concentrated under vacuo. A column chromatography afford the title compound (129 mg, 18% yield) as a light brown solid. MS (ES+) m/z: 201.9 $[(M+H)^+]$.

Step 3: Preparation of 2-chloro-8-methyl-6-(4,4,5,5-tetramethyl-1,3,2-dioxaborolan-2-yl)imidazo[1,2-b]pyridazine The title compound was prepared from 2,6-dichloro-8-methyl-imidazo[1,2-b]pyridazine in analogy to the synthesis of the boronic ester 6-5, step 2.

General Procedures

1) Suzuki Cross Coupling Reaction Between a Tosylate Intermediate of General Formula 5 and a Boronic Ester/Acid 6 (as Prepared Herein Above):

To a solution of an intermediate 5 in 1,4-dioxane, was added 1.5 equivalent of a boronic ester intermediate 6 as a 0.33 M solution in $CH_3CN$ and 4.0 equivalent of $K_2CO_3$ delivered as a 2 M aqueous solution. As a solvent either 1,4-dioxane, $CH_3CN$, water or a mixture thereof were used. The reaction mixture was degassed with Argon for 5 minutes and a palladium catalyst [either $Pd(dppf)Cl_2 \cdot CH_2Cl_2$ (0.2 eq. CAS #95464-05-4) or XPhos PdG4 (CAS #1599466-81-5)] was added. The reaction mixture was heated at 90° C. until completion (usually between 2 and 8 hours), cooled to room temperature, filtered over a pad of Celite preconditioned with $CH_3CN$, washed with $CH_3CN$ and concentrated in vacuo. A purification was performed either by column chromatography or reverse phase preparative HPLC to afford the desired product.

2) General Procedure for the Boc Protecting Group Removal:

To a solution of a boc-protected derivative of the compound of formula (I) in $CH_2Cl_2$ (2 mL) was added TFA (2 mL) and the reaction mixture was stirred at room temperature until completion, usually between 1 and 3 hours. The mixture was then evaporated in vacuo and purified via reverse phase preparative HPLC, using a ACN/Water+0.1% $Et_3N$ gradient on a Gemini NX, 12 nm, 5 μm, 100×30 mm column to afford the compound of formula (I).

Example 1

7-(2,8-dimethylimidazo[1,2-b]pyridazin-6-yl)-2-piperazin-1-yl-thiazolo[3,2-a]pyrimidin-5-one

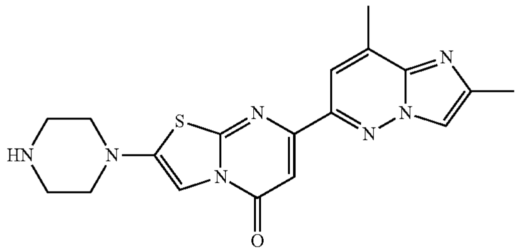

Step 1: Using the general procedure 1, a cross coupling reaction between tert-butyl 4-[5-oxo-7-(p-tolylsulfonyloxy)thiazolo[3,2-a]pyrimidin-2-yl]piperazine-1-carboxylate (intermediate 5-1) and 2,8-dimethyl-6-(4,4,5,5-tetramethyl-1,3,2-dioxaborolan-2-yl)imidazo[1,2-b]pyridazine (boronic ester 6-1) gave tert-butyl 4-[7-(2,8-dimethylimidazo[1,2-b]pyridazin-6-yl)-5-oxo-thiazolo[3,2-a]pyrimidin-2-yl]piperazine-1-carboxylate. MS (ES+) m/z: 482.4 $[(M+H)^+]$.

Step 2: A deprotection using the general procedure 2, gave 7-(2,8-dimethylimidazo[1,2-b]pyridazin-6-yl)-2-piperazin-1-yl-thiazolo[3,2-a]pyrimidin-5-one (20 mg) as a light yellow solid. MS (ES+) m/z: 382.1 $[(M+H)^+]$.

Example 2

7-(2,8-dimethylimidazo[1,2-b]pyridazin-6-yl)-2-(1,2,3,6-tetrahydropyridin-4-yl)thiazolo[3,2-a]pyrimidin-5-one

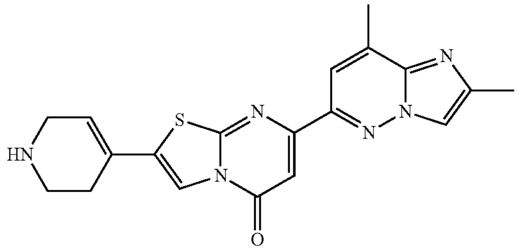 [SMILES: Cc1cn2nc(-c3cc(=O)n4cc(C5=CCNCC5)sc4n3)cc(C)c2n1]

Step 1: Using the general procedure 1, a cross coupling reaction between tert-butyl 4-[5-oxo-7-(p-tolylsulfonyloxy)thiazolo[3,2-a]pyrimidin-2-yl]-3,6-dihydro-2H-pyridine-1-carboxylate (intermediate 5-2) and 2,8-dimethyl-6-(4,4,5,5-tetramethyl-1,3,2-dioxaborolan-2-yl)imidazo[1,2-b]pyridazine (boronic ester 6-1) gave tert-butyl 4-[7-(2,8-dimethylimidazo[1,2-b]pyridazin-6-yl)-5-oxo-thiazolo[3,2-a]pyrimidin-2-yl]-3,6-dihydro-2H-pyridine-1-carboxylate. MS (ES+) m/z: 479.3 $[(M+H)^+]$.

Step 2: A deprotection using the general procedure 2, gave 7-(2,8-dimethylimidazo[1,2-b]pyridazin-6-yl)-2-(1,2,3,6-tetrahydropyridin-4-yl)thiazolo[3,2-a]pyrimidin-5-one (20 mg) as a light yellow solid. MS (ES+) m/z: 379 $[(M+H)^+]$.

Example 3

7-(2,8-dimethylimidazo[1,2-b]pyridazin-6-yl)-2-(3,3-dimethylpiperazin-1-yl)thiazolo[3,2-a]pyrimidin-5-one

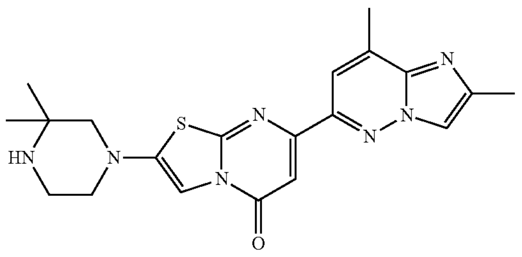

Step 1: Using the general procedure 1, a cross coupling reaction between tert-butyl 2,2-dimethyl-4-[5-oxo-7-(p-tolylsulfonyloxy)thiazolo[3,2-a]pyrimidin-2-yl] piperazine-1-carboxylate (intermediate 5-3) and 2,8-dimethyl-6-(4,4,5,5-tetramethyl-1,3,2-dioxaborolan-2-yl)imidazo[1,2-b] pyridazine (boronic ester 6-1) gave tert-butyl 4-[7-(2,8-dimethylimidazo[1,2-b]pyridazin-6-yl)-5-oxo-thiazolo[3,2-a]pyrimidin-2-yl]-2,2-dimethyl-piperazine-1-carboxylate (478 mg, 55% yield) as a yellow solid. MS (ES+) m/z: 510.3 $[(M+H)^+]$.

Step 2: A deprotection using the general procedure 2, gave 7-(2,8-dimethylimidazo[1,2-b]pyridazin-6-yl)-2-(3,3-dimethylpiperazin-1-yl)thiazolo[3,2-a]pyrimidin-5-one (71 mg. 42% yield) as a light yellow solid. MS (ES+) m/z: 410.3 $[(M+H)^+]$.

Example 4

2-(4,7-diazaspiro[2.5]octan-7-yl)-7-(2,8-dimethylimidazo[1,2-b]pyridazin-6-yl)thiazolo[3,2-a]pyrimidin-5-one

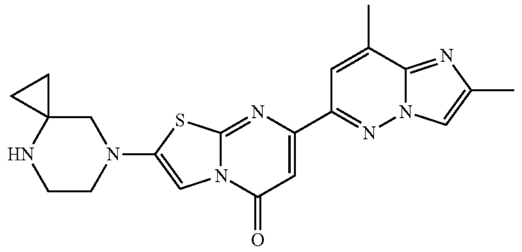 [SMILES: Cc1cn2nc(-c3cc(=O)n4cc(N5CCNC6(CC6)C5)sc4n3)cc(C)c2n1]

Step 1: Using the general procedure 1, a cross coupling reaction between tert-butyl 7-[5-oxo-7-(p-tolylsulfonyloxy) thiazolo[3,2-a]pyrimidin-2-yl]-4,7-diazaspiro[2.5]octane-4-carboxylate (intermediate 5-4) and 2,8-dimethyl-6-(4,4,5,5-tetramethyl-1,3,2-dioxaborolan-2-yl)imidazo[1,2-b] pyridazine (boronic ester 6-1) gave tert-butyl 7-[7-(2,8-dimethylimidazo[1,2-b]pyridazin-6-yl)-5-oxo-thiazolo[3,2-a]pyrimidin-2-yl]-4,7-diazaspiro[2.5]octane-4-carboxylate (50 mg) as a yellow solid. MS (ES+) m/z: 508.5 $[(M+H)^+]$.

Step 2: A deprotection using the general procedure 2, gave 2-(4,7-diazaspiro[2.5]octan-7-yl)-7-(2,8-dimethylimidazo [1,2-b]pyridazin-6-yl)thiazolo[3,2-a]pyrimidin-5-one (40 mg) as a light yellow solid. MS (ES+) m/z: 408.2 $[(M+H)^+]$.

Example 5

7-(4-fluoro-2-methyl-1,3-benzoxazol-6-yl)-2-piperazin-1-yl-thiazolo[3,2-a]pyrimidin-5-one

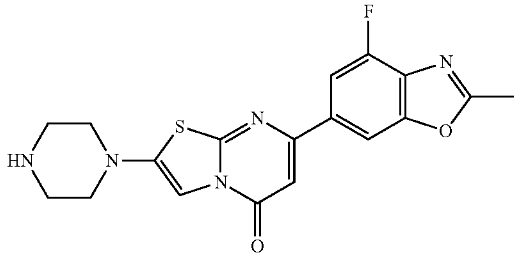 [SMILES: Cc1nc2c(F)cc(-c3cc(=O)n4cc(N5CCNCC5)sc4n3)cc2o1]

Step 1: Using the general procedure 1, a cross coupling reaction between tert-butyl 4-[5-oxo-7-(p-tolylsulfonyloxy) thiazolo[3,2-a]pyrimidin-2-yl]piperazine-1-carboxylate (intermediate 5-1) and 4-fluoro-2-methyl-6-(4,4,5,5-tetramethyl-1,3,2-dioxaborolan-2-yl)-1,3-benzoxazole (boronic ester 6-2) gave tert-butyl 4-[7-(4-fluoro-2-methyl-1,3-benzoxazol-6-yl)-5-oxo-thiazolo[3,2-a]pyrimidin-2-yl]piperazine-1-carboxylate (26 mg, 12% yield) as a yellow solid. MS (ES+) m/z: 486.2 $[(M+H)^+]$.

Step 2: A deprotection using the general procedure 2, gave 7-(4-fluoro-2-methyl-1,3-benzoxazol-6-yl)-2-piperazin-1-yl-thiazolo[3,2-a]pyrimidin-5-one (143 mg, 82% yield) as a light yellow solid. MS (ES+) m/z: 386.2 $[(M+H)^+]$.

Example 6

7-(2,8-dimethylimidazo[1,2-b]pyridazin-6-yl)-2-[(3S)-3-methylpiperazin-1-yl]thiazolo[3,2-a]pyrimidin-5-one

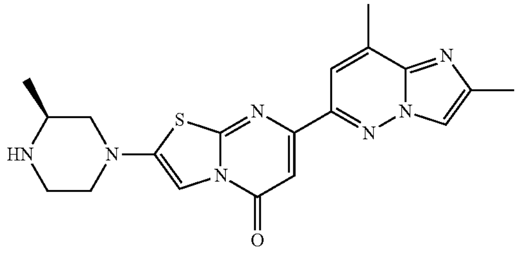 [SMILES: Cc1cn2nc(-c3cc(=O)n4cc(N5CCN[C@@H](C)C5)sc4n3)cc(C)c2n1]

Step 1: Using the general procedure 1, a cross coupling reaction between tert-butyl (2S)-2-methyl-4-[5-oxo-7-(p-tolylsulfonyloxy)thiazolo[3,2-a]pyrimidin-2-yl]piperazine-1-carboxylate (intermediate 5-5) and 2,8-dimethyl-6-(4,4,5,5-tetramethyl-1,3,2-dioxaborolan-2-yl)imidazo[1,2-b] pyridazine (boronic ester 6-1) gave tert-butyl (2S)-4-[7-(2,8-dimethylimidazo[1,2-b]pyridazin-6-yl)-5-oxo-thiazolo[3,2-a]pyrimidin-2-yl]-2-methyl-piperazine-1-carboxylate (578 mg) as a yellow solid. MS (ES+) m/z: 496.3 $[(M+H)^+]$.

Step 2: A deprotection using the general procedure 2, gave 7-(2,8-dimethylimidazo[1,2-b]pyridazin-6-yl)-2-[(3S)-3-methylpiperazin-1-yl]thiazolo[3,2-a]pyrimidin-5-one (128 mg, 28% yield) as a light yellow solid. MS (ES+) m/z: 396.3 $[(M+H)^+]$.

Example 7

7-(2,8-dimethylimidazo[1,2-b]pyridazin-6-yl)-2-[(3R)-3-methylpiperazin-1-yl]thiazolo[3,2-a]pyrimidin-5-one

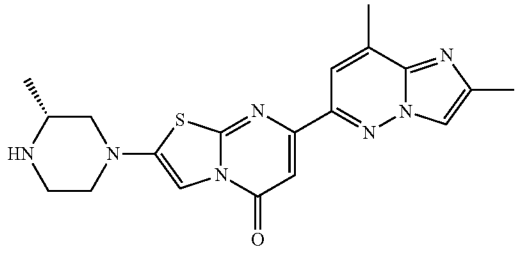 [SMILES: Cc1cn2nc(-c3cc(=O)n4cc(N5CCN[C@H](C)C5)sc4n3)cc(C)c2n1]

Step 1: Using the general procedure 1, a cross coupling reaction between tert-butyl (2R)-2-methyl-4-[5-oxo-7-(p-tolylsulfonyloxy)thiazolo[3,2-a]pyrimidin-2-yl]piperazine-1-carboxylate (intermediate 5-6) and 2,8-dimethyl-6-(4,4,5,5-tetramethyl-1,3,2-dioxaborolan-2-yl)imidazo[1,2-b]pyridazine (boronic ester 6-1) gave tert-butyl (2R)-4-[7-(2,8-dimethylimidazo[1,2-b]pyridazin-6-yl)-5-oxo-thiazolo[3,2-a]pyrimidin-2-yl]-2-methyl-piperazine-1-carboxylate (378 mg) as a yellow solid. MS (ES+) m/z: 496.3 $[(M+H)^+]$.

Step 2: A deprotection using the general procedure 2, gave 7-(2,8-dimethylimidazo[1,2-b]pyridazin-6-yl)-2-[(3R)-3-methylpiperazin-1-yl]thiazolo[3,2-a]pyrimidin-5-one (129 mg, 41% yield) as a light yellow solid. MS (ES+) m/z: 396.3 $[(M+H)^+]$.

Example 8

7-(2,8-dimethylimidazo[1,2-b]pyridazin-6-yl)-2-(3,5-dimethylpiperazin-1-yl)thiazolo[3,2-a]pyrimidin-5-one

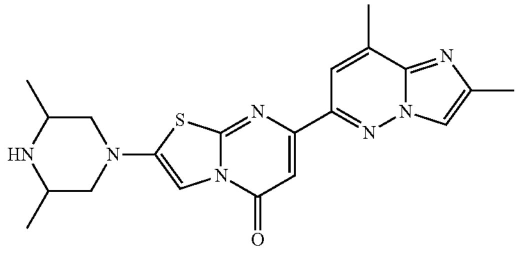 [SMILES: Cc1cn2nc(-c3cc(=O)n4cc(N5CC(C)NC(C)C5)sc4n3)cc(C)c2n1]

Step 1: Using the general procedure 1, a cross coupling reaction between tert-butyl 2,6-dimethyl-4-[5-oxo-7-(p-tolylsulfonyloxy)thiazolo[3,2-a]pyrimidin-2-yl]piperazine-1-carboxylate (intermediate 5-7) and 2,8-dimethyl-6-(4,4,5,5-tetramethyl-1,3,2-dioxaborolan-2-yl)imidazo[1,2-b]pyridazine (boronic ester 6-1) gave tert-butyl 4-[7-(2,8-dimethylimidazo[1,2-b]pyridazin-6-yl)-5-oxo-thiazolo[3,2-a]pyrimidin-2-yl]-2,6-dimethyl-piperazine-1-carboxylate (270 mg) as a yellow solid. MS (ES+) m/z: 510.4 $[(M+H)^+]$.

Step 2: A deprotection using the general procedure 2, gave 7-(2,8-dimethylimidazo[1,2-b]pyridazin-6-yl)-2-(3,5-dimethylpiperazin-1-yl)thiazolo[3,2-a]pyrimidin-5-one (65 mg, 30% yield) as a light yellow solid. MS (ES+) m/z: 410.3 $[(M+H)^+]$.

Example 9

7-(2,8-dimethylimidazo[1,2-b]pyridazin-6-yl)-2-[(8aS)-3,4,6,7,8,8a-hexahydro-1H-pyrrolo[1,2-a]pyrazin-2-yl]thiazolo[3,2-a]pyrimidin-5-one

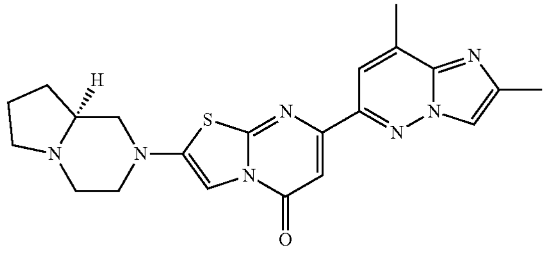 [SMILES: Cc1cn2nc(-c3cc(=O)n4cc(N5CCN6CCC[C@H]6C5)sc4n3)cc(C)c2n1]

Using the general procedure 1, a cross coupling reaction between [5-oxo-2-[(8aS)-3,4,6,7,8,8a-hexahydro-1H-pyrrolo[1,2-a]pyrazin-2-yl]thiazolo[3,2-a]pyrimidin-7-yl] 4-methylbenzene-sulfonate (intermediate 5-8) and 2,8-dimethyl-6-(4,4,5,5-tetramethyl-1,3,2-dioxaborolan-2-yl)imidazo[1,2-b]pyridazine (boronic ester 6-1) gave 7-(2,8-dimethylimidazo[1,2-b]pyridazin-6-yl)-2-[(8aS)-3,4,6,7,8,8a-hexahydro-1H-pyrrolo[1,2-a]pyrazin-2-yl]thiazolo[3,2-a]pyrimidin-5-one (10 mg, 7% yield) as a yellow solid. MS (ES+) m/z: 422.3 $[(M+H)^+]$.

Example 10

7-(2-methylimidazo[1,2-b]pyridazin-6-yl)-2-piperazin-1-yl-thiazolo[3,2-a]pyrimidin-5-one

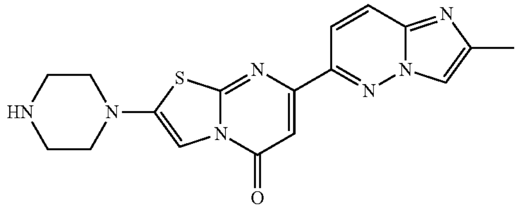 [SMILES: Cc1cn2nc(-c3cc(=O)n4cc(N5CCNCC5)sc4n3)ccc2n1]

Step 1: Using the general procedure 1, a cross coupling reaction between tert-butyl 4-[5-oxo-7-(p-tolylsulfonyloxy)thiazolo[3,2-a]pyrimidin-2-yl]piperazine-1-carboxylate (intermediate 5-1) and 2-methyl-6-(4,4,5,5-tetramethyl-1,3,2-dioxaborolan-2-yl)imidazo[1,2-b]pyridazine (boronic ester 6-3) gave tert-butyl 4-[7-(2-methylimidazo[1,2-b]pyridazin-6-yl)-5-oxo-thiazolo[3,2-a]pyrimidin-2-yl]piperazine-1-carboxylate (98 mg, 70% yield) as a yellow solid. MS (ES+) m/z: 468.3 $[(M+H)^+]$.

Step 2: A deprotection using the general procedure 2, gave 7-(2-methylimidazo[1,2-b]pyridazin-6-yl)-2-piperazin-1-yl-thiazolo[3,2-a]pyrimidin-5-one (82 mg) as a light yellow solid. MS (ES+) m/z: 368.3 $[(M+H)^+]$.

Example 11

7-[2-methyl-8-(trifluoromethyl)imidazo[1,2-b]pyridazin-6-yl]-2-piperazin-1-yl-thiazolo[3,2-a]pyrimidin-5-one

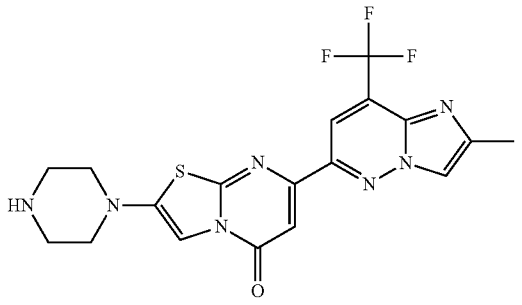 [SMILES: Cc1cn2nc(-c3cc(=O)n4cc(N5CCNCC5)sc4n3)cc(C(F)(F)F)c2n1]

Step 1: Using the general procedure 1, a cross coupling reaction between tert-butyl 4-[5-oxo-7-(p-tolylsulfonyloxy)thiazolo[3,2-a]pyrimidin-2-yl]piperazine-1-carboxylate (intermediate 5-1) and 2-methyl-6-(4,4,5,5-tetramethyl-1,3,2-dioxaborolan-2-yl)-8-(trifluoromethyl)imidazo[1,2-b]pyridazine (boronic ester 6-4) gave tert-butyl 4-[7-[2-methyl-8-(trifluoromethyl)imidazo[1,2-b]pyridazin-6-yl]-5-oxo-thiazolo[3,2-a]pyrimidin-2-yl]piperazine-1-carboxylate (42 mg, 57% yield) as a yellow solid. MS (ES+) m/z: 536.3 $[(M+H)^+]$.

Step 2: A deprotection using the general procedure 2, gave 7-[2-methyl-8-(trifluoromethyl)imidazo[1,2-b]pyridazin-6-yl]-2-piperazin-1-yl-thiazolo[3,2-a]pyrimidin-5-one (13 mg, 53% yield) as a light orange solid. MS (ES+) m/z: 436.3 $[(M+H)^+]$.

Example 12

7-(8-ethyl-2-methyl-imidazo[1,2-b]pyridazin-6-yl)-2-piperazin-1-yl-thiazolo[3,2-a]pyrimidin-5-one

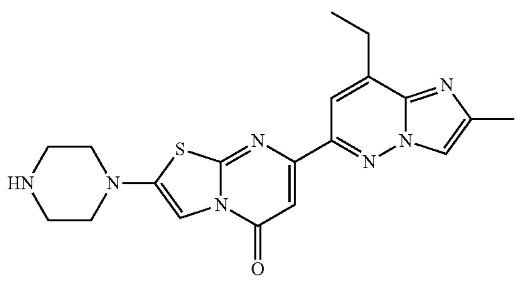 [SMILES: CCc1cc(-c2cc(=O)n3cc(N4CCNCC4)sc3n2)nn2cc(C)nc12]

Step 1: Using the general procedure 1, a cross coupling reaction between tert-butyl 4-[5-oxo-7-(p-tolylsulfonyloxy)thiazolo[3,2-a]pyrimidin-2-yl]piperazine-1-carboxylate (intermediate 5-1) and 8-ethyl-2-methyl-6-(4,4,5,5-tetramethyl-1,3,2-dioxaborolan-2-yl)imidazo[1,2-b]pyridazine (boronic ester 6-5) gave tert-butyl 4-[7-(8-ethyl-2-methyl-imidazo[1,2-b]pyridazin-6-yl)-5-oxo-thiazolo[3,2-a]pyrimidin-2-yl]piperazine-1-carboxylate (66 mg, 73% yield) as a yellow solid. MS (ES+) m/z: 496.4 $[(M+H)^+]$.

Step 2: A deprotection using the general procedure 2, gave 7-(8-ethyl-2-methyl-imidazo[1,2-b]pyridazin-6-yl)-2-piperazin-1-yl-thiazolo[3,2-a]pyrimidin-5-one (58 mg, 98% yield) as a light yellow solid. MS (ES+) m/z: 396.3 $[(M+H)^+]$.

Example 13

7-(8-methoxy-2-methyl-imidazo[1,2-b]pyridazin-6-yl)-2-piperazin-1-yl-thiazolo[3,2-a]pyrimidin-5-one

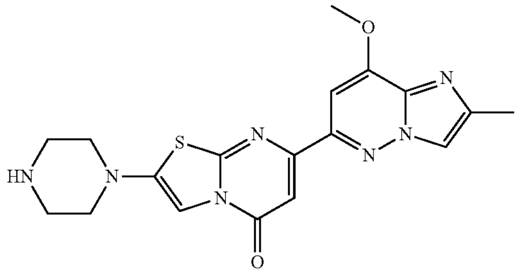 [SMILES: COc1cc(-c2cc(=O)n3cc(N4CCNCC4)sc3n2)nn2cc(C)nc12]

Step 1: Using the general procedure 1, a cross coupling reaction between tert-butyl 4-[5-oxo-7-(p-tolylsulfonyloxy)thiazolo[3,2-a]pyrimidin-2-yl]piperazine-1-carboxylate (intermediate 5-1) and 8-methoxy-2-methyl-6-(4,4,5,5-tetramethyl-1,3,2-dioxaborolan-2-yl)imidazo[1,2-b]pyridazine (boronic ester 6-6) gave tert-butyl 4-[7-(8-methoxy-2-methyl-imidazo[1,2-b]pyridazin-6-yl)-5-oxo-thiazolo[3,2-a]pyrimidin-2-yl]piperazine-1-carboxylate (16 mg, 18% yield) as a yellow solid. MS (ES+) m/z: 498.3 $[(M+H)^+]$.

Step 2: A deprotection using the general procedure 2, gave 7-(8-methoxy-2-methyl-imidazo[1,2-b]pyridazin-6-yl)-2-piperazin-1-yl-thiazolo[3,2-a]pyrimidin-5-one (9 mg, 71% yield) as a light yellow solid. MS (ES+) m/z: 398.2 $[(M+H)^+]$.

Example 14

2-(3,8-diazabicyclo[3.2.1]octan-8-yl)-7-(2,8-dimethylimidazo[1,2-b]pyridazin-6-yl)thiazolo[3,2-a]pyrimidin-5-one

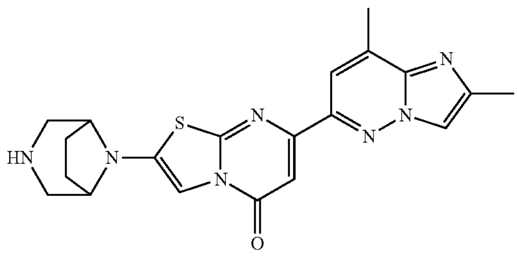 [SMILES: Cc1cn2nc(-c3cc(=O)n4cc(N5C6CCC5CNC6)sc4n3)cc(C)c2n1]

Step 1: Using the general procedure 1, a cross coupling reaction between tert-butyl 8-[5-oxo-7-(p-tolylsulfonyloxy)thiazolo[3,2-a]pyrimidin-2-yl]-3,8-diazabicyclo[3.2.1]octane-3-carboxylate (intermediate 5-9) and 2,8-dimethyl-6-(4,4,5,5-tetramethyl-1,3,2-dioxaborolan-2-yl)imidazo[1,2-b]pyridazine (boronic ester 6-1) gave tert-butyl 8-[7-(2,8-dimethylimidazo[1,2-b]pyridazin-6-yl)-5-oxo-thiazolo[3,2-a]pyrimidin-2-yl]-3,8-diazabicyclo[3.2.1]octane-3-carboxylate (189 mg, 43% yield) as a yellow solid. MS (ES+) m/z: 508.4 $[(M+H)^+]$.

Step 2: A deprotection using the general procedure 2, gave 2-(3,8-diazabicyclo[3.2.1]octan-8-yl)-7-(2,8-dimethylimidazo[1,2-b]pyridazin-6-yl)thiazolo[3,2-a]pyrimidin-5-one (33 mg, 21% yield) as a light yellow solid. MS (ES+) m/z: 408.3 [(M+H)$^+$].

Example 15

7-(2,8-dimethylimidazo[1,2-b]pyridazin-6-yl)-2-[(8aR)-3,4,6,7,8,8a-hexahydro-1H-pyrrolo[1,2-a]pyrazin-2-yl]thiazolo[3,2-a]pyrimidin-5-one

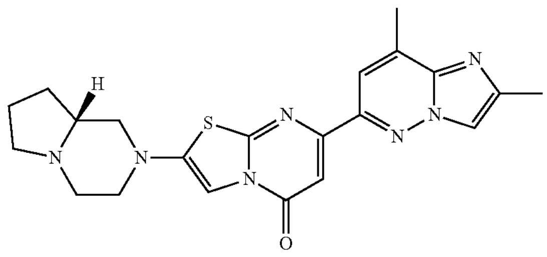 [SMILES: Cc1cn2nc(-c3cc(=O)n4cc(N5CCN6CCC[C@@H]6C5)sc4n3)cc(C)c2n1]

Using the general procedure 1, a cross coupling reaction between [5-oxo-2-[(8aR)-3,4,6,7,8,8a-hexahydro-1H-pyrrolo[1,2-a]pyrazin-2-yl]thiazolo[3,2-a]pyrimidin-7-yl] 4-methylbenzene-sulfonate (intermediate 5-10) and 2,8-dimethyl-6-(4,4,5,5-tetramethyl-1,3,2-dioxaborolan-2-yl)imidazo[1,2-b]pyridazine (boronic ester 6-1) gave 7-(2,8-dimethylimidazo[1,2-b]pyridazin-6-yl)-2-[(8aR)-3,4,6,7,8,8a-hexahydro-1H-pyrrolo[1,2-a]pyrazin-2-yl]thiazolo[3,2-a]pyrimidin-5-one (12 mg, 8% yield) as a yellow solid. MS (ES+) m/z: 422.3 [(M+H)$^+$].

Example 16

7-(2,8-dimethylimidazo[1,2-b]pyridazin-6-yl)-2-[(1S,4S)-2,5-diazabicyclo[2.2.1]heptan-2-yl]thiazolo[3,2-a]pyrimidin-5-one

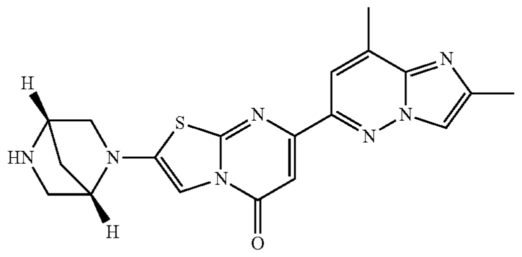 [SMILES: Cc1cn2nc(-c3cc(=O)n4cc(N5C[C@@H]6C[C@H]5CN6)sc4n3)cc(C)c2n1]

Step 1: Using the general procedure 1, a cross coupling reaction between tert-butyl (1S,4S)-5-[5-oxo-7-(p-tolylsulfonyloxy)thiazolo[3,2-a]pyrimidin-2-yl]-2,5-diazabicyclo[2.2.1]heptane-2-carboxylate (intermediate 5-11) and 2,8-dimethyl-6-(4,4,5,5-tetramethyl-1,3,2-dioxaborolan-2-yl)imidazo[1,2-b]pyridazine (boronic ester 6-1) gave tert-butyl (1S,4S)-5-[7-(2,8-dimethylimidazo[1,2-b]pyridazin-6-yl)-5-oxo-thiazolo[3,2-a]pyrimidin-2-yl]-2,5-diazabicyclo[2.2.1]heptane-2-carboxylate (211 mg, 45% yield) as a yellow solid. MS (ES+) m/z: 494.3 [(M+H)$^+$].

Step 2: A deprotection using the general procedure 2, gave 7-(2,8-dimethylimidazo[1,2-b]pyridazin-6-yl)-2-[(1S,4S)-2,5-diazabicyclo[2.2.1]heptan-2-yl]thiazolo[3,2-a]pyrimidin-5-one (150 mg) as a light yellow solid. MS (ES+) m/z: 394.3 [(M+H)$^+$].

Example 17

2-(2,3,3a,4,6,6a-hexahydro-1H-pyrrolo[3,4-c]pyrrol-5-yl)-7-(2,8-dimethylimidazo[1,2-b]pyridazin-6-yl)thiazolo[3,2-a]pyrimidin-5-one

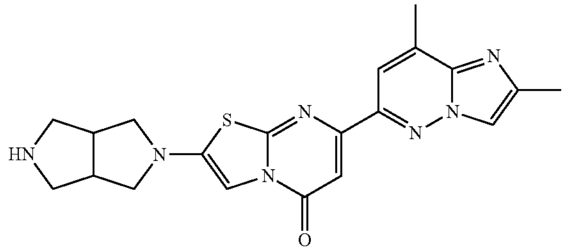 [SMILES: Cc1cn2nc(-c3cc(=O)n4cc(N5CC6CNCC6C5)sc4n3)cc(C)c2n1]

Step 1: Using the general procedure 1, a cross coupling reaction between tert-butyl 2-[5-oxo-7-(p-tolylsulfonyloxy)thiazolo[3,2-a]pyrimidin-2-yl]-1,3,3a,4,6,6a-hexahydropyrrolo[3,4-c]pyrrole-5-carboxylate (intermediate 5-12) and 2,8-dimethyl-6-(4,4,5,5-tetramethyl-1,3,2-dioxaborolan-2-yl)imidazo[1,2-b]pyridazine (boronic ester 6-1) gave tert-butyl 2-[7-(2,8-dimethylimidazo[1,2-b]pyridazin-6-yl)-5-oxo-thiazolo[3,2-a]pyrimidin-2-yl]-1,3,3a,4,6,6a-hexahydropyrrolo[3,4-c]pyrrole-5-carboxylate (105 mg, 33% yield) as a yellow solid. MS (ES+) m/z: 508.2 [(M+H)$^+$].

Step 2: A deprotection using the general procedure 2, gave 2-(2,3,3a,4,6,6a-hexahydro-1H-pyrrolo[3,4-c]pyrrol-5-yl)-7-(2,8-dimethylimidazo[1,2-b]pyridazin-6-yl)thiazolo[3,2-a]pyrimidin-5-one (110 mg 98% yield) as a light yellow solid. MS (ES+) m/z: 408.2 [(M+H)$^+$].

Example 18

7-(8-cyclopropyl-2-methyl-imidazo[1,2-b]pyridazin-6-yl)-2-piperazin-1-yl-thiazolo[3,2-a]pyrimidin-5-one

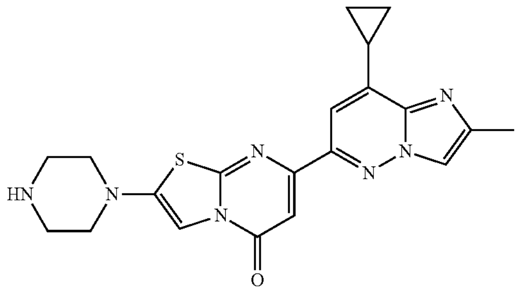 [SMILES: Cc1cn2nc(-c3cc(=O)n4cc(N5CCNCC5)sc4n3)cc(C3CC3)c2n1]

Step 1: Using the general procedure 1, a cross coupling reaction between tert-butyl 4-[5-oxo-7-(p-tolylsulfonyloxy)thiazolo[3,2-a]pyrimidin-2-yl]piperazine-1-carboxylate (intermediate 5-1) and 8-cyclopropyl-2-methyl-6-(4,4,5,5-tetramethyl-1,3,2-dioxaborolan-2-yl)imidazo[1,2-b]pyridazine (boronic ester 6-7) gave tert-butyl 4-[7-(8-cyclopropyl-2-methyl-imidazo[1,2-b]pyridazin-6-yl)-5-oxo-thiazolo[3,2-a]pyrimidin-2-yl]piperazine-1-carboxylate (62 mg, 70% yield) as a yellow solid. MS (ES+) m/z: 508.4 [(M+H)$^+$].

Step 2: A deprotection using the general procedure 2, gave 7-(8-cyclopropyl-2-methyl-imidazo[1,2-b]pyridazin-6-yl)-2-piperazin-1-yl-thiazolo[3,2-a]pyrimidin-5-one (5 mg, 10% yield) as a light yellow solid. MS (ES+) m/z: 408.4 [(M+H)$^+$].

Example 19

7-(8-isopropenyl-2-methyl-imidazo[1,2-b]pyridazin-6-yl)-2-piperazin-1-yl-thiazolo[3,2-a]pyrimidin-5-one

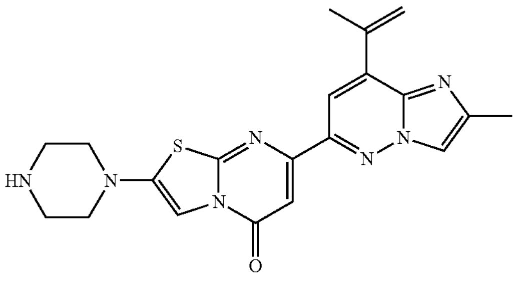 [SMILES: C=C(C)c1cc(-c2cc(=O)n3cc(N4CCNCC4)sc3n2)nn2cc(C)nc12]

Step 1: Using the general procedure 1, a cross coupling reaction between tert-butyl 4-[5-oxo-7-(p-tolylsulfonyloxy)thiazolo[3,2-a]pyrimidin-2-yl]piperazine-1-carboxylate (intermediate 5-1) and 8-isopropenyl-2-methyl-6-(4,4,5,5-tetramethyl-1,3,2-dioxaborolan-2-yl)imidazo[1,2-b]pyridazine (boronic ester 6-8) gave tert-butyl 4-[7-(8-isopropenyl-2-methyl-imidazo[1,2-b]pyridazin-6-yl)-5-oxo-thiazolo[3,2-a]pyrimidin-2-yl]piperazine-1-carboxylate (119 mg, 74% yield) as a yellow solid. MS (ES+) m/z: 508.4 [(M+H)$^+$].

Step 2: A deprotection using the general procedure 2, gave 7-(8-isopropenyl-2-methyl-imidazo[1,2-b]pyridazin-6-yl)-2-piperazin-1-yl-thiazolo[3,2-a]pyrimidin-5-one (66 mg, 69% yield) as a light yellow solid. MS (ES+) m/z: 408.2 [(M+H)$^+$].

Example 20

7-(2,7-dimethyloxazolo[5,4-b]pyridin-5-yl)-2-piperazin-1-yl-thiazolo[3,2-a]pyrimidin-5-one

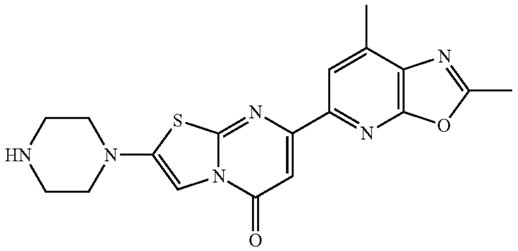 [SMILES: Cc1nc2c(C)cc(-c3cc(=O)n4cc(N5CCNCC5)sc4n3)nc2o1]

Step 1: Using the general procedure 1, a cross coupling reaction between tert-butyl 4-[5-oxo-7-(p-tolylsulfonyloxy)thiazolo[3,2-a]pyrimidin-2-yl]piperazine-1-carboxylate (intermediate 5-1) and 2,7-dimethyl-5-(4,4,5,5-tetramethyl-1,3,2-dioxaborolan-2-yl)oxazolo[5,4-b]pyridine (boronic ester 6-9) gave tert-butyl 4-[7-(2,7-dimethyloxazolo[5,4-b]pyridin-5-yl)-5-oxo-thiazolo[3,2-a]pyrimidin-2-yl]piperazine-1-carboxylate (36 mg, 44% yield) as a yellow solid. MS (ES+) m/z: 483.3 [(M+H)$^+$].

Step 2: A deprotection using the general procedure 2, gave 7-(2,7-dimethyloxazolo[5,4-b]pyridin-5-yl)-2-piperazin-1-yl-thiazolo[3,2-a]pyrimidin-5-one (7 mg, 23% yield) as a light yellow solid. MS (ES+) m/z: 383.2 [(M+H)$^+$].

Example 21

7-(2,8-dimethylimidazo[1,2-b]pyridazin-6-yl)-2-[(3S)-3-pyrrolidin-1-ylpyrrolidin-1-yl]thiazolo[3,2-a]pyrimidin-5-one

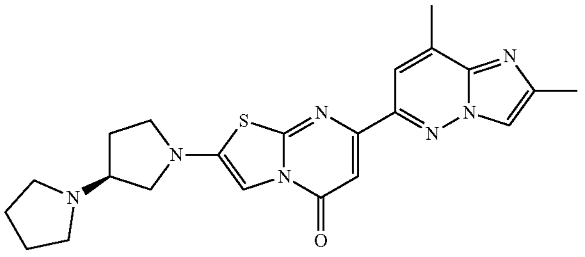 [SMILES: Cc1cn2nc(-c3cc(=O)n4cc(N5CC[C@H](N6CCCC6)C5)sc4n3)cc(C)c2n1]

Using the general procedure 1, a cross coupling reaction between [5-oxo-2-[(3S)-3-pyrrolidin-1-ylpyrrolidin-1-yl]thiazolo[3,2-a]pyrimidin-7-yl] 4-methylbenzenesulfonate (intermediate 5-13) and 2,8-dimethyl-6-(4,4,5,5-tetramethyl-1,3,2-dioxaborolan-2-yl)imidazo[1,2-b]pyridazine (boronic ester 6-1) gave 7-(2,8-dimethylimidazo[1,2-b]pyridazin-6-yl)-2-[(3S)-3-pyrrolidin-1-ylpyrrolidin-1-yl]thiazolo[3,2-a]pyrimidin-5-one (7 mg, 3% yield) as a yellow oil. MS (ES+) m/z: 436.2 [(M+H)$^+$].

Step 2: A deprotection using the general procedure 2, gave 2-(2,3,3a,4,6,6a-hexahydro-1H-pyrrolo[3,4-c]pyrrol-5-yl)-7-(2,8-dimethylimidazo[1,2-b]pyridazin-6-yl)thiazolo[3,2-a]pyrimidin-5-one (110 mg·98% yield) as a light yellow solid. MS (ES+) m/z: 408.2 [(M+H)$^+$].

Example 22

2-(2,8-diazaspiro[4.5]decan-2-yl)-7-(2,8-dimethylimidazo[1,2-b]pyridazin-6-yl)thiazolo[3,2-a]pyrimidin-5-one

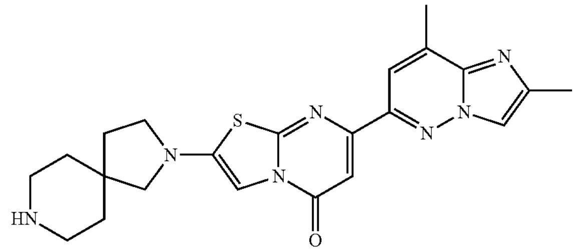 [SMILES: Cc1cn2nc(-c3cc(=O)n4cc(N5CCC6(CCNCC6)C5)sc4n3)cc(C)c2n1]

Step 1: Using the general procedure 1, a cross coupling reaction between tert-butyl 2-[5-oxo-7-(p-tolylsulfonyloxy)thiazolo[3,2-a]pyrimidin-2-yl]-2,8-diazaspiro-[4.5]decane-8-carboxylate (intermediate 5-14) and 2,8-dimethyl-6-(4,4, 5,5-tetramethyl-1,3,2-dioxaborolan-2-yl)imidazo[1,2-b]pyridazine (boronic ester 6-1) gave tert-butyl 2-[7-(2,8-dimethylimidazo[1,2-b]pyridazin-6-yl)-5-oxo-thiazolo[3,2-a]pyrimidin-2-yl]-2,8-diazaspiro[4.5]decane-8-carboxylate (44 mg, 37% yield) as a yellow solid. MS (ES+) m/z: 536.4 $[(M+H)^+]$.

Step 2: A deprotection using the general procedure 2, gave 2-(2,8-diazaspiro[4.5]decan-2-yl)-7-(2,8-dimethylimidazo[1,2-b]pyridazin-6-yl)thiazolo[3,2-a]pyrimidin-5-one (61 mg, 98% yield) as a light red oil. MS (ES+) m/z: 436.2 $[(M+H)^+]$.

Example 23

7-(8-isopropyl-2-methyl-imidazo[1,2-b]pyridazin-6-yl)-2-piperazin-1-yl-thiazolo[3,2-a]pyrimidin-5-one

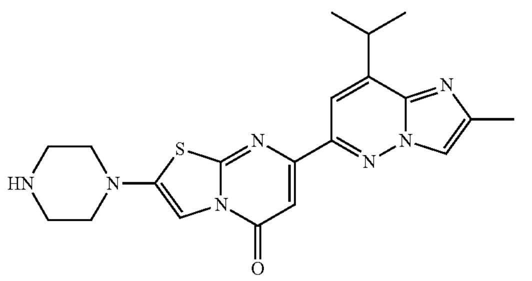 [SMILES: Cc1cn2nc(-c3cc(=O)n4cc(N5CCNCC5)sc4n3)cc(C(C)C)c2n1]

Step 1: Using the general procedure 1, a cross coupling reaction between tert-butyl 4-[5-oxo-7-(p-tolylsulfonyloxy)thiazolo[3,2-a]pyrimidin-2-yl]piperazine-1-carboxylate (intermediate 5-1) and 8-isopropyl-2-methyl-6-(4,4,5,5-tetramethyl-1,3,2-dioxaborolan-2-yl)imidazo[1,2-b]pyridazine (boronic ester 6-10) gave tert-butyl 4-[7-(8-isopropyl-2-methyl-imidazo[1,2-b]pyridazin-6-yl)-5-oxo-thiazolo[3,2-a]pyrimidin-2-yl]piperazine-1-carboxylate (86 mg, 64% yield) as a yellow solid. MS (ES+) m/z: 510.3 $[(M+H)^+]$.

Step 2: A deprotection using the general procedure 2, gave 7-(8-isopropyl-2-methyl-imidazo[1,2-b]pyridazin-6-yl)-2-piperazin-1-yl-thiazolo[3,2-a]pyrimidin-5-one (65 mg, 94% yield) as a light yellow solid. MS (ES+) m/z: 410.3 $[(M+H)^+]$.

Example 24

7-(2,8-dimethylimidazo[1,2-b]pyridazin-6-yl)-2-(4-piperidyl)thiazolo[3,2-a]pyrimidin-5-one

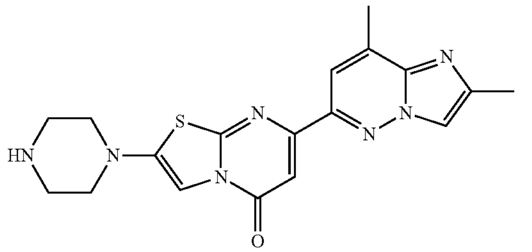

Step 1: Using the general procedure 1, a cross coupling reaction between tert-butyl 4-[5-oxo-7-(p-tolylsulfonyloxy)thiazolo[3,2-a]pyrimidin-2-yl]piperidine-1-carboxylate (intermediate 5-15) and 2,8-dimethyl-6-(4,4,5,5-tetramethyl-1,3,2-dioxaborolan-2-yl)imidazo[1,2-b]pyridazine (boronic ester 6-1) gave tert-butyl 4-[7-(2,8-dimethylimidazo[1,2-b]pyridazin-6-yl)-5-oxo-thiazolo[3,2-a]pyrimidin-2-yl]piperidine-1-carboxylate (35 mg, 53% yield) as a yellow solid. MS (ES+) m/z: 481.2 $[(M+H)^+]$.

Step 2: A deprotection using the general procedure 2, gave 7-(2,8-dimethylimidazo[1,2-b]pyridazin-6-yl)-2-(4-piperidyl)thiazolo[3,2-a]pyrimidin-5-one (3 mg, 6% yield) as a light red oil. MS (ES+) m/z: 381 $[(M+H)^+]$.

Example 25

7-[2-methyl-8-(trifluoromethyl)imidazo[1,2-b]pyridazin-6-yl]-2-[(8aR)-3,4,6,7,8,8a-hexahydro-1H-pyrrolo[1,2-a]pyrazin-2-yl]thiazolo[3,2-a]pyrimidin-5-one

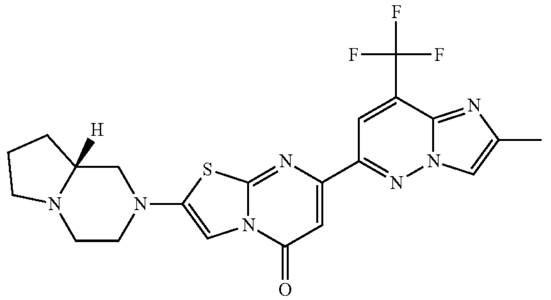 [SMILES: Cc1cn2nc(-c3cc(=O)n4cc(N5CCN6CCC[C@@H]6C5)sc4n3)cc(C(F)(F)F)c2n1]

Using the general procedure 1, a cross coupling reaction between [5-oxo-2-[(8aR)-3,4,6,7,8,8a-hexahydro-1H-pyrrolo[1,2-a]pyrazin-2-yl]thiazolo[3,2-a]pyrimidin-7-yl] 4-methylbenzene-sulfonate (intermediate 5-10) and 2-methyl-6-(4,4,5,5-tetramethyl-1,3,2-dioxaborolan-2-yl)-8-(trifluoromethyl)imidazo[1,2-b]pyridazine (boronic ester 6-4) gave 7-[2-methyl-8-(trifluoromethyl)imidazo[1,2-b]pyridazin-6-yl]-2-[(8aR)-3,4,6,7,8,8a-hexahydro-1H-pyrrolo[1,2-a]pyrazin-2-yl]thiazolo[3,2-a]pyrimidin-5-one (6 mg, 20% yield) as a yellow solid. MS (ES+) m/z: 476.2 $[(M+H)^+]$.

Example 26

7-(2,8-dimethylimidazo[1,2-b]pyridazin-6-yl)-2-(4-fluoro-4-piperidyl)thiazolo[3,2-a]pyrimidin-5-one

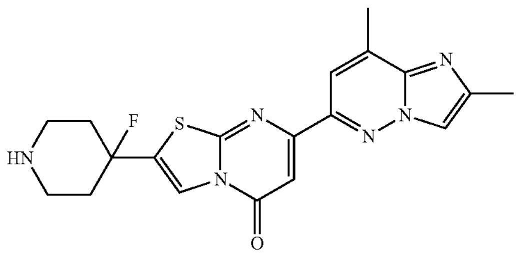 [SMILES: Cc1cn2nc(-c3cc(=O)n4cc(C5(F)CCNCC5)sc4n3)cc(C)c2n1]

Step 1: Using the general procedure 1, a cross coupling reaction between tert-butyl 4-hydroxy-4-[5-oxo-7-(p-tolylsulfonyloxy)thiazolo[3,2-a]pyrimidin-2-yl]piperidine-1-carboxylate (intermediate 5-16) and 2,8-dimethyl-6-(4,4, 5,5-tetramethyl-1,3,2-dioxaborolan-2-yl)imidazo[1,2-b]pyridazine (boronic ester 6-1) gave tert-butyl 4-[7-(2,8-dimethylimidazo[1,2-b]pyridazin-6-yl)-5-oxo-thiazolo[3,2-a]pyrimidin-2-yl]-4-hydroxy-piperidine-1-carboxylate (220 mg, 77% yield) as a light brown oil. MS (ES+) m/z: 497.3 $[(M+H)^+]$.

Step 2: To a stirred solution of tert-butyl 4-[7-(2,8-dimethylimidazo[1,2-b]pyridazin-6-yl)-5-oxo-thiazolo[3,2-a]pyrimidin-2-yl]-4-hydroxy-piperidine-1-carboxylate (220 mg, 0.44 mmol) in $CH_2Cl_2$ at −78° C. was added DAST (176 uL, 1.33 mmol in 3 mL of $CH_2Cl_2$) and the reaction was gently warmed up to 0° C. The reaction mixture was partitioned between $CH_2Cl_2$ and an aqueous saturated solution of $NaHCO_3$. The organic phase was dried and concentrated under vacuo. The residue was purified by column chromatography to give tert-butyl 4-[7-(2,8-dimethylimidazo[1,2-b]pyridazin-6-yl)-5-oxo-thiazolo[3,2-a]pyrimidin-2-yl]-4-fluoro-piperidine-1-carboxylate (80 mg, 33% yield) as a light yellow powder. MS (ES+) m/z: 499.6 $[(M+H)^+]$.

Step 3: A deprotection using the general procedure 2, gave 7-(2,8-dimethylimidazo[1,2-b]pyridazin-6-yl)-2-(4-fluoro-4-piperidyl)thiazolo[3,2-a]pyrimidin-5-one (23 mg, 71% yield) as a light red oil. MS (ES+) m/z: 399.2 $[(M+H)^+]$.

Example 27

7-[8-(difluoromethoxy)-2-methyl-imidazo[1,2-b]pyridazin-6-yl]-2-piperazin-1-yl-thiazolo[3,2-a]pyrimidin-5-one

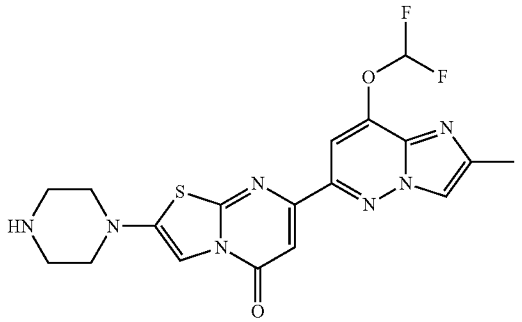 [SMILES: Cc1cn2nc(-c3cc(=O)n4cc(N5CCNCC5)sc4n3)cc(OC(F)F)c2n1]

Step 1: Using the general procedure 1, a cross coupling reaction between tert-butyl 4-[5-oxo-7-(p-tolylsulfonyloxy)thiazolo[3,2-a]pyrimidin-2-yl]piperazine-1-carboxylate (intermediate 5-1) and 8-(difluoromethoxy)-2-methyl-6-(4,4,5,5-tetramethyl-1,3,2-dioxaborolan-2-yl)imidazo[1,2-b]pyridazine (boronic ester 6-11) gave tert-butyl 4-[7-[8-(difluoromethoxy)-2-methyl-imidazo[1,2-b]pyridazin-6-yl]-5-oxo-thiazolo[3,2-a]pyrimidin-2-yl]piperazine-1-carboxylate (143 mg, 71% yield) as a yellow solid. MS (ES+) m/z: 534.2 $[(M+H)^+]$.

Step 2: A deprotection using the general procedure 2, gave 7-[8-(difluoromethoxy)-2-methyl-imidazo[1,2-b]pyridazin-6-yl]-2-piperazin-1-yl-thiazolo[3,2-a]pyrimidin-5-one (70 mg, 60% yield) as a light yellow solid. MS (ES+) m/z: 434.2 $[(M+H)^+]$.

Example 28

7-[2-methyl-7-(trifluoromethyl)oxazolo[5,4-b]pyridin-5-yl]-2-piperazin-1-yl-thiazolo[3,2-a]pyrimidin-5-one

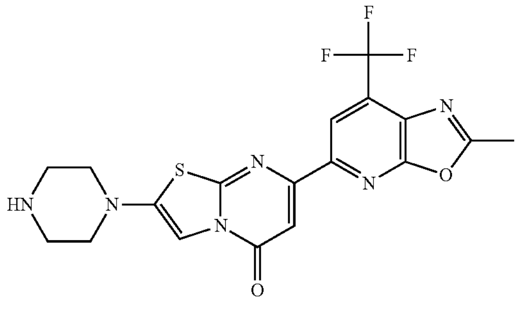 [SMILES: Cc1nc2c(C(F)(F)F)cc(-c3cc(=O)n4cc(N5CCNCC5)sc4n3)nc2o1]

Step 1: Using the general procedure 1, a cross coupling reaction between tert-butyl 4-[5-oxo-7-(p-tolylsulfonyloxy)thiazolo[3,2-a]pyrimidin-2-yl]piperazine-1-carboxylate (intermediate 5-1) and N-[2-chloro-6-(4,4,5,5-tetramethyl-1,3,2-dioxaborolan-2-yl)-4-(trifluoromethyl)-3-pyridyl]acetamide (boronic ester 6-12) gave tert-butyl 4-[7-[2-methyl-7-(trifluoromethyl)oxazolo[5,4-b]pyridin-5-yl]-5-oxo-thiazolo[3,2-a]pyrimidin-2-yl]piperazine-1-carboxylate (102 mg, 35% yield) as a yellow solid. MS (ES+) m/z: 537.2 $[(M+H)^+]$.

Step 2: A deprotection using the general procedure 2, gave 7-[2-methyl-7-(trifluoromethyl)oxazolo[5,4-b]pyridin-5-yl]-2-piperazin-1-yl-thiazolo[3,2-a]pyrimidin-5-one (56 mg, 35% yield) as a light yellow solid. MS (ES+) m/z: 437.2 $[(M+H)^+]$.

Example 29

7-(8-methoxy-2-methyl-imidazo[1,2-b]pyridazin-6-yl)-2-(4-piperidyl)thiazolo[3,2-a]pyrimidin-5-one

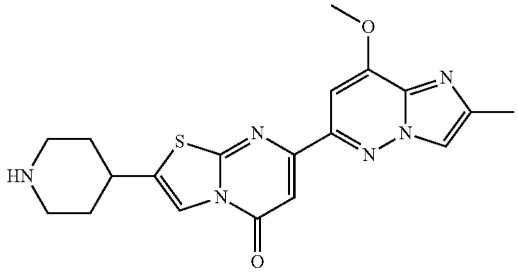

Step 1: Using the general procedure 1, a cross coupling reaction between tert-butyl 4-[5-oxo-7-(p-tolylsulfonyloxy)thiazolo[3,2-a]pyrimidin-2-yl]piperidine-1-carboxylate (intermediate 5-15) and 8-methoxy-2-methyl-6-(4,4,5,5-tetramethyl-1,3,2-dioxaborolan-2-yl)imidazo[1,2-b]pyridazine (boronic ester 6-6) gave tert-butyl 4-[7-(8-methoxy-2-methyl-imidazo[1,2-b]pyridazin-6-yl)-5-oxo-thiazolo[3,2-a]pyrimidin-2-yl]piperidine-1-carboxylate.

Step 2: A deprotection using the general procedure 2, gave the title compound 7-(8-methoxy-2-methyl-imidazo[1,2-b]pyridazin-6-yl)-2-(4-piperidyl)thiazolo[3,2-a]pyrimidin-5-one. MS (ES+) m/z: 397.1 $[(M+H)^+]$.

Example 30

7-(2,7-dimethyloxazolo[5,4-b]pyridin-5-yl)-2-(4-piperidyl)thiazolo[3,2-a]pyrimidin-5-one

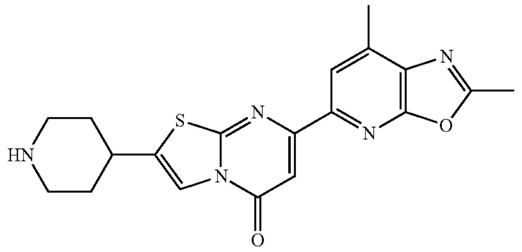 [SMILES: Cc1nc2c(C)cc(-c3cc(=O)n4cc(C5CCNCC5)sc4n3)nc2o1]

Step 1: Using the general procedure 1, a cross coupling reaction between tert-butyl 4-[5-oxo-7-(p-tolylsulfonyloxy)thiazolo[3,2-a]pyrimidin-2-yl]piperidine-1-carboxylate (intermediate 5-15) and 2,7-dimethyl-5-(4,4,5,5-tetramethyl-1,3,2-dioxaborolan-2-yl)oxazolo[5,4-b]pyridine (boronic ester 6-9) gave tert-butyl 4-[7-(2,7-dimethyloxazolo[5,4-b]pyridin-5-yl)-5-oxo-thiazolo[3,2-a]pyrimidin-2-yl]piperidine-1-carboxylate.

Step 2: A deprotection using the general procedure 2, gave the title compound 7-(2,7-dimethyloxazolo[5,4-b]pyridin-5-yl)-2-(4-piperidyl)thiazolo[3,2-a]pyrimidin-5-one. MS (ES+) m/z: MS (ES+) m/z: 382.1 [(M+H)$^+$].

Example 31

7-(2-chloro-8-methyl-imidazo[1,2-b]pyridazin-6-yl)-2-(4-piperidyl)thiazolo[3,2-a]pyrimidin-5-one

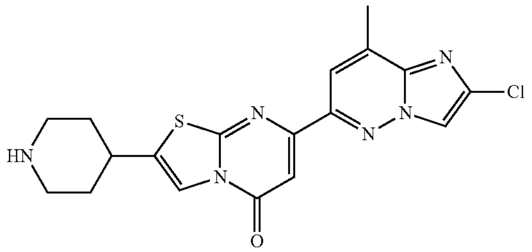 [SMILES: Cc1cc(-c2cc(=O)n3cc(C4CCNCC4)sc3n2)nn2cc(Cl)nc12]

Step 1: Using the general procedure 1, a cross coupling reaction between tert-butyl 4-[5-oxo-7-(p-tolylsulfonyloxy)thiazolo[3,2-a]pyrimidin-2-yl]piperidine-1-carboxylate (intermediate 5-15) and 2-chloro-8-methyl-6-(4,4,5,5-tetramethyl-1,3,2-dioxaborolan-2-yl)imidazo[1,2-b]pyridazine (boronic ester 6-13) gave tert-butyl 4-[7-(2-chloro-8-methyl-imidazo[1,2-b]pyridazin-6-yl)-5-oxo-thiazolo[3,2-a]pyrimidin-2-yl]piperidine-1-carboxylate.

Step 2: A deprotection using the general procedure 2, gave the title compound 7-(2-chloro-8-methyl-imidazo[1,2-b]pyridazin-6-yl)-2-(4-piperidyl)thiazolo[3,2-a]pyrimidin-5-one. MS (ES+) m/z: 401.1 [(M+H)$^+$].

Examples 32 & 33

7-(2,8-dimethylimidazo[1,2-b]pyridazin-6-yl)-2-[(3R,4R)-3-fluoro-4-piperidyl]thiazolo[3,2-a]pyrimidin-5-one and 7-(2,8-dimethylimidazo[1,2-b]pyridazin-6-yl)-2-[(3S,4S)-3-fluoro-4-piperidyl]thiazolo[3,2-a]pyrimidin-5-one

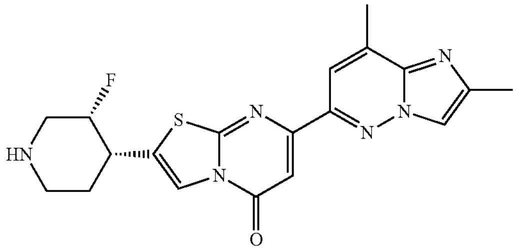

and

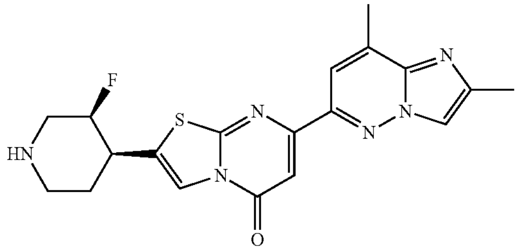

Step 1: Using the general procedure 1, separately, a cross coupling reaction between tert-butyl (3R,4R)-3-fluoro-4-[5-oxo-7-(p-tolylsulfonyloxy)thiazolo[3,2-a]pyrimidin-2-yl]piperidine-1-carboxylate or tert-butyl (3S,4S)-3-fluoro-4-[5-oxo-7-(p-tolylsulfonyloxy)thiazolo[3,2-a]pyrimidin-2-yl]piperidine-1-carboxylate (intermediates 5-17) and 2,8-dimethyl-6-(4,4,5,5-tetramethyl-1,3,2-dioxaborolan-2-yl)imidazo[1,2-b]pyridazine (boronic ester 6-1) gave separately tert-butyl (3R,4R)-4-[7-(2,8-dimethylimidazo[1,2-b]pyridazin-6-yl)-5-oxo-thiazolo[3,2-a]pyrimidin-2-yl]-3-fluoro-piperidine-1-carboxylate and tert-butyl (3S,4S)-4-[7-(2,8-dimethylimidazo[1,2-b]pyridazin-6-yl)-5-oxo-thiazolo[3,2-a]pyrimidin-2-yl]-3-fluoro-piperidine-1-carboxylate respectively.

Step 2: A deprotection using the general procedure 2, gave the title compounds 7-(2,8-dimethylimidazo[1,2-b]pyridazin-6-yl)-2-[(3R,4R)-3-fluoro-4-piperidyl]thiazolo[3,2-a]pyrimidin-5-one and 7-(2,8-dimethylimidazo[1,2-b]pyridazin-6-yl)-2-[(3S,4S)-3-fluoro-4-piperidyl]thiazolo[3,2-a]pyrimidin-5-one respectively. MS (ES+) m/z: 399.2 [(M+H)$^+$] for each enantiomer. Optical rotation for the two enantiomers was measured in MeOH (20° C., 589 nm): Example 32 is (−)-enantiomer, optical rotation: −47°; Example 33 is (+)-enantiomer, optical rotation: +37°.

Examples 34 & 35

7-(8-methoxy-2-methyl-imidazo[1,2-b]pyridazin-6-yl)-2-[(3R,4R)-3-fluoro-4-piperidyl]thiazolo[3,2-a]pyrimidin-5-one and 7-(8-methoxy-2-methyl-imidazo[1,2-b]pyridazin-6-yl)-2-[(3S,4S)-3-fluoro-4-piperidyl]thiazolo[3,2-a]pyrimidin-5-one

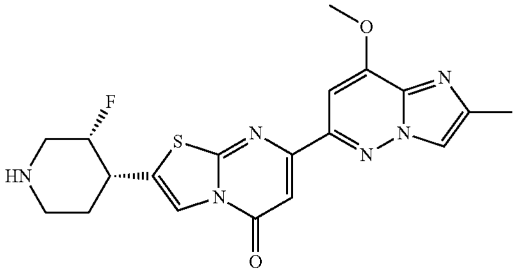

and

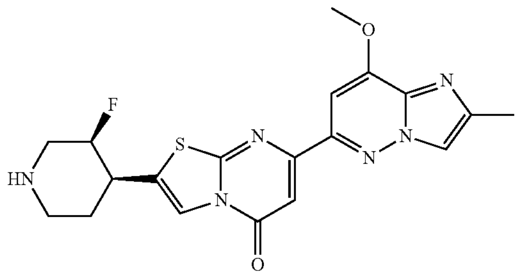

Step 1: Using the general procedure 1, separately, a cross coupling reaction between tert-butyl (3R,4R)-3-fluoro-4-[5-oxo-7-(p-tolylsulfonyloxy)thiazolo[3,2-a]pyrimidin-2-yl]piperidine-1-carboxylate or tert-butyl (3S,4S)-3-fluoro-4-[5-oxo-7-(p-tolylsulfonyloxy)thiazolo[3,2-a]pyrimidin-2-yl]piperidine-1-carboxylate (intermediates 5-17) and 8-methoxy-2-methyl-6-(4,4,5,5-tetramethyl-1,3,2-dioxaborolan-2-yl)imidazo[1,2-b]pyridazine (boronic ester 6-6) gave separately tert-butyl (3R,4R)-3-fluoro-4-[7-(8-methoxy-2-methyl-imidazo[1,2-b]pyridazin-6-yl)-5-oxo-thiazolo[3,2-a]pyrimidin-2-yl]piperidine-1-carboxylate and tert-butyl (3S,4S)-3-fluoro-4-[7-(8-methoxy-2-methyl-imidazo[1,2-b]pyridazin-6-yl)-5-oxo-thiazolo[3,2-a]pyrimidin-2-yl]piperidine-1-carboxylate respectively.

Step 2: A deprotection using the general procedure 2, gave separately the title compounds 7-(8-methoxy-2-methyl-imidazo[1,2-b]pyridazin-6-yl)-2-[(3R,4R)-3-fluoro-4-piperidyl]thiazolo[3,2-a]pyrimidin-5-one and 7-(8-methoxy-2-methyl-imidazo[1,2-b]pyridazin-6-yl)-2-[(3S,4S)-3-fluoro-4-piperidyl]thiazolo[3,2-a]pyrimidin-5-one respectively. MS (ES+) m/z: 415.2 [$(M+H)^+$] for each enantiomer. Optical rotation for the two enantiomers was measured in MeOH (20° C., 589 nm): Example 34 is (−)-enantiomer, optical rotation: −43°; Example 35 is (+)-enantiomer, optical rotation: +47°.

Examples 36 & 37

7-(2,8-dimethylimidazo[1,2-b]pyridazin-6-yl)-2-[(7S)-4-azaspiro[2.5]octan-7-yl]thiazolo[3,2-a]pyrimidin-5-one and 7-(2,8-dimethylimidazo[1,2-b]pyridazin-6-yl)-2-[(7R)-4-azaspiro[2.5]octan-7-yl]thiazolo[3,2-a]pyrimidin-5-one

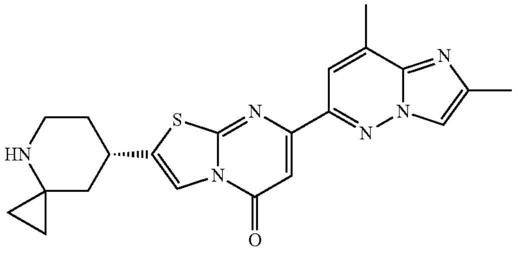

and

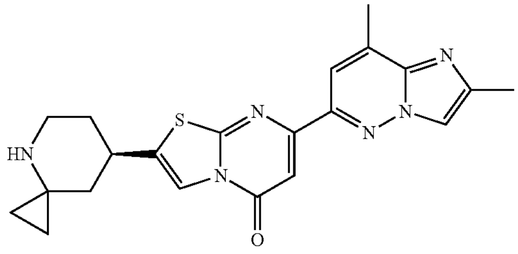

Step 1: Using the general procedure 1, separately, a cross coupling reaction between tert-butyl (7S)-7-[5-oxo-7-(p-tolylsulfonyloxy)thiazolo[3,2-a]pyrimidin-2-yl]-4-azaspiro[2.5]octane-4-carboxylatecarboxylate or tert-butyl (7R)-7-[5-oxo-7-(p-tolylsulfonyloxy)thiazolo[3,2-a]pyrimidin-2-yl]-4-azaspiro[2.5]octane-4-carboxylatecarboxylate (intermediates 5-19) and 2,8-dimethyl-6-(4,4,5,5-tetramethyl-1,3,2-dioxaborolan-2-yl)imidazo[1,2-b]pyridazine (boronic ester 6-1) gave separately tert-butyl (7S)-7-[7-(2,8-dimethylimidazo[1,2-b]pyridazin-6-yl)-5-oxo-thiazolo[3,2-a]pyrimidin-2-yl]-4-azaspiro[2.5]octane-4-carboxylate and tert-butyl (7S)-7-[7-(2,8-dimethylimidazo[1,2-b]pyridazin-6-yl)-5-oxo-thiazolo[3,2-a]pyrimidin-2-yl]-4-azaspiro[2.5]octane-4-carboxylate respectively.

Step 2: A deprotection using the general procedure 2, gave separately the title compounds 7-(2,8-dimethylimidazo[1,2-b]pyridazin-6-yl)-2-[(7S)-4-azaspiro[2.5]octan-7-yl]thiazolo[3,2-a]pyrimidin-5-one and 7-(2,8-dimethylimidazo[1,2-b]pyridazin-6-yl)-2-[(7R)-4-azaspiro[2.5]octan-7-yl]thiazolo[3,2-a]pyrimidin-5-one respectively. MS (ES+) m/z: 407.1 [$(M+H)^+$] for each enantiomer. Optical rotation for the two enantiomers was measured in MeOH (20° C., 589 nm): Example 36 is (−)-enantiomer, optical rotation: −39°; Example 37 is (+)-enantiomer, optical rotation: +39°.

Examples 38 & 39

7-(2,8-dimethylimidazo[1,2-b]pyridazin-6-yl)-2-[(3S,4R)-3-fluoro-4-piperidyl]thiazolo[3,2-a]pyrimidin-5-one and 7-(2,8-dimethylimidazo[1,2-b]pyridazin-6-yl)-2-[(3R,4S)-3-fluoro-4-piperidyl]thiazolo[3,2-a]pyrimidin-5-one

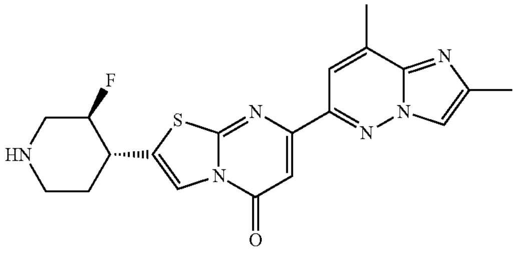

and

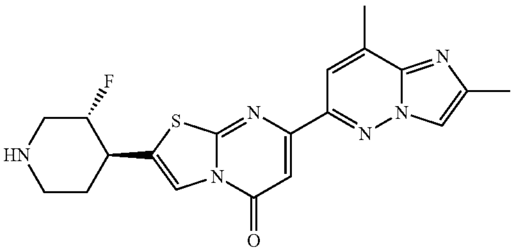

Step 1: Using the general procedure 1, separately, a cross coupling reaction between tert-butyl (3S,4R)-3-fluoro-4-[5-oxo-7-(p-tolylsulfonyloxy)thiazolo[3,2-a]pyrimidin-2-yl]piperidine-1-carboxylate or tert-butyl (3R,4S)-3-fluoro-4-[5-oxo-7-(p-tolylsulfonyloxy)thiazolo[3,2-a]pyrimidin-2-yl]piperidine-1-carboxylate (intermediates 5-18) and 2,8-dimethyl-6-(4,4,5,5-tetramethyl-1,3,2-dioxaborolan-2-yl)imidazo[1,2-b]pyridazine (boronic ester 6-1) gave separately tert-butyl (3S,4R)-4-[7-(2,8-dimethylimidazo[1,2-b]pyridazin-6-yl)-5-oxo-thiazolo[3,2-a]pyrimidin-2-yl]-3-fluoro-piperidine-1-carboxylate and tert-butyl (3R,4S)-4-[7-(2,8-dimethylimidazo[1,2-b]pyridazin-6-yl)-5-oxo-thiazolo[3,2-a]pyrimidin-2-yl]-3-fluoro-piperidine-1-carboxylate respectively.

Step 2: A deprotection using the general procedure 2, gave separately the title compounds 7-(2,8-dimethylimidazo[1,2-b]pyridazin-6-yl)-2-[(3S,4R)-3-fluoro-4-piperidyl]thiazolo[3,2-a]pyrimidin-5-one and 7-(2,8-dimethylimidazo[1,2-b]pyridazin-6-yl)-2-[(3R,4S)-3-fluoro-4-piperidyl]thiazolo[3,2-a]pyrimidin-5-one respectively. MS (ES+) m/z: 399.2 [$(M+H)^+$] for each enantiomer. Optical rotation for the two enantiomers was measured in MeOH (20° C., 589 nm): Example 38 is (−)-enantiomer, optical rotation: −12°; Example 39 is (+)-enantiomer, optical rotation: +7°.

Examples 40 & 41

7-(8-methoxy-2-methyl-imidazo[1,2-b]pyridazin-6-yl)-2-[(7S)-4-azaspiro[2.5]octan-7-yl]thiazolo[3,2-a]pyrimidin-5-one and 7-(8-methoxy-2-methyl-imidazo[1,2-b]pyridazin-6-yl)-2-[(7R)-4-azaspiro[2.5]octan-7-yl]thiazolo[3,2-a]pyrimidin-5-one

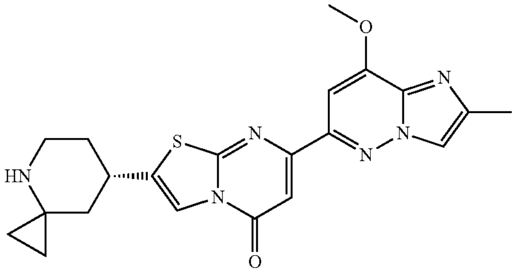

and

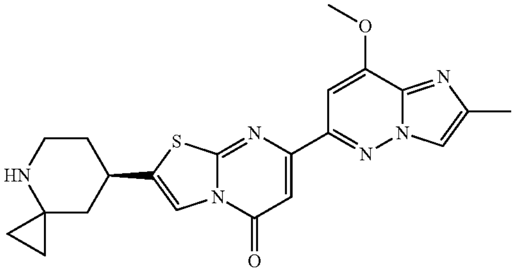

Step 1: Using the general procedure 1, separately, a cross coupling reaction between tert-butyl (7S)-7-[5-oxo-7-(p-tolylsulfonyloxy)thiazolo[3,2-a]pyrimidin-2-yl]-4-azaspiro[2.5]octane-4-carboxylatecarboxylate or tert-butyl (7R)-7-[5-oxo-7-(p-tolylsulfonyloxy)thiazolo[3,2-a]pyrimidin-2-yl]-4-azaspiro[2.5]octane-4-carboxylatecarboxylate (intermediates 5-19) and 8-methoxy-2-methyl-6-(4,4,5,5-tetramethyl-1,3,2-dioxaborolan-2-yl)imidazo[1,2-b]pyridazine (boronic ester 6-6) gave tert-butyl (7S)-7-[7-(8-methoxy-2-methyl-imidazo[1,2-b]pyridazin-6-yl)-5-oxo-thiazolo[3,2-a]pyrimidin-2-yl]-4-azaspiro[2.5]octane-4-carboxylate and tert-butyl (7R)-7-[7-(8-methoxy-2-methyl-imidazo[1,2-b]pyridazin-6-yl)-5-oxo-thiazolo[3,2-a]pyrimidin-2-yl]-4-azaspiro[2.5]octane-4-carboxylate respectively.

Step 2: A deprotection using the general procedure 2, gave separately the title compounds 7-(8-methoxy-2-methyl-imidazo[1,2-b]pyridazin-6-yl)-2-[(7S)-4-azaspiro[2.5]octan-7-yl]thiazolo[3,2-a]pyrimidin-5-one and 7-(8-methoxy-2-methyl-imidazo[1,2-b]pyridazin-6-yl)-2-[(7R)-4-azaspiro[2.5]octan-7-yl]thiazolo[3,2-a]pyrimidin-5-one respectively. MS (ES+) m/z: 423.2 [$(M+H)^+$] for each enantiomer. Optical rotation for the two enantiomers in MeOH (20° C., 589 nm): −65° and +30° respectively. Optical rotation for the two enantiomers was measured in MeOH (20° C., 589 nm): Example 40 is (−)-enantiomer, optical rotation: −65°; Example 41 is (+)-enantiomer, optical rotation: +30°.

Example 42

2-(4-fluoro-4-piperidyl)-7-(8-methoxy-2-methyl-imidazo[1,2-b]pyridazin-6-yl)thiazolo[3,2-a]pyrimidin-5-one

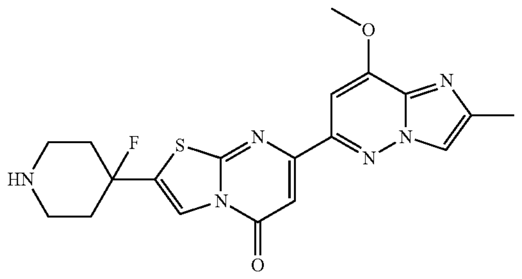

Step 1: Using the general procedure 1, a cross coupling reaction between tert-butyl 4-hydroxy-4-[5-oxo-7-(p-tolylsulfonyloxy)thiazolo[3,2-a]pyrimidin-2-yl]piperidine-1-carboxylate (intermediate 5-16) and 8-methoxy-2-methyl-6-(4,4,5,5-tetramethyl-1,3,2-dioxaborolan-2-yl)imidazo[1,2-b]pyridazine (boronic ester 6-6) gave tert-butyl 4-hydroxy-4-[7-(8-methoxy-2-methyl-imidazo[1,2-b]pyridazin-6-yl)-5-oxo-thiazolo[3,2-a]pyrimidin-2-yl]piperidine-1-carboxylate (775 mg, 79% yield). MS (ES+) m/z: 513.3 [(M+H)+].

Step 2: In analogy to example 26, step 2, from tert-butyl 4-hydroxy-4-[7-(8-methoxy-2-methyl-imidazo[1,2-b]pyridazin-6-yl)-5-oxo-thiazolo[3,2-a]pyrimidin-2-yl]piperidine-1-carboxylate was prepared tert-butyl 4-fluoro-4-[7-(8-methoxy-2-methyl-imidazo[1,2-b]pyridazin-6-yl)-5-oxo-thiazolo[3,2-a]pyrimidin-2-yl]piperidine-1-carboxylate as a white solid (23 mg, 30% yield). MS (ES+) m/z: 515.2 [(M+H)+].

Step 3: A deprotection using the general procedure 2, gave the title compound 2-(4-fluoro-4-piperidyl)-7-(8-methoxy-2-methyl-imidazo[1,2-b]pyridazin-6-yl)thiazolo[3,2-a]pyrimidin-5-one. MS (ES+) m/z: 415.1 [(M+H)+].

Example 43

7-(2-chloro-8-methyl-imidazo[1,2-b]pyridazin-6-yl)-2-[(3R,4R)-3-fluoro-4-piperidyl]thiazolo[3,2-a]pyrimidin-5-one

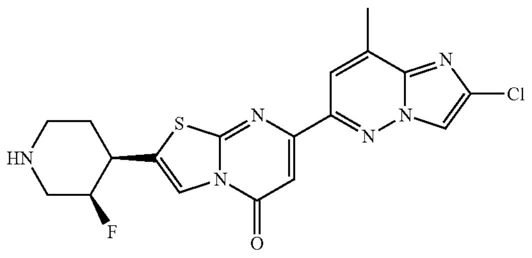 [SMILES: Cc1cc(-c2cc(=O)n3cc([C@@H]4CCNC[C@@H]4F)sc3n2)nn2cc(Cl)nc12]

Step 1: Using the general procedure 1, a cross coupling reaction between tert-butyl (3R,4R)-3-fluoro-4-[5-oxo-7-(p-tolylsulfonyloxy)thiazolo[3,2-a]pyrimidin-2-yl]piperidine-1-carboxylate (intermediate 5) and 2-chloro-8-methyl-6-(4,4,5,5-tetramethyl-1,3,2-dioxaborolan-2-yl)imidazo[1,2-b]pyridazine (boronic ester 6-13) gave tert-butyl ((3R,4R)-4-[7-(2-chloro-8methyl-imidazo[1,2-b]pyridazin-6-yl)-5-oxo-thiazolo[3,2-a]pyrimidin-2-yl]-]-3-fluoro-piperidine-1-carboxylate.

Step 2: A deprotection using the general procedure 2, gave the title compound 7-(2-chloro-8-methyl-imidazo[1,2-b]pyridazin-6-yl)-2-[(3R,4R)-3-fluoro-4-piperidyl]thiazolo[3,2-a]pyrimidin-5-one. MS (ES+) m/z: 419.2 [(M+H)+].

Example 44

7-(2,7-dimethyloxazolo[5,4-b]pyridin-5-yl)-2-[(3R,4R)-3-fluoro-4-piperidyl]thiazolo[3,2-a]pyrimidin-5-one

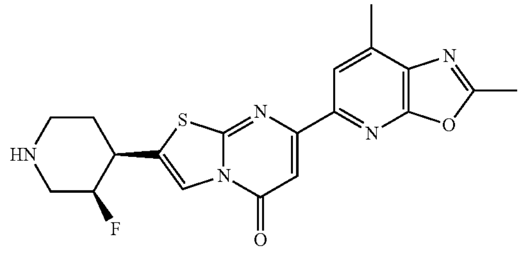 [SMILES: Cc1nc2c(C)cc(-c3cc(=O)n4cc([C@@H]5CCNC[C@@H]5F)sc4n3)nc2o1]

Step 1: Using the general procedure 1, a cross coupling reaction between tert-butyl (3R,4R)-3-fluoro-4-[5-oxo-7-(p-tolylsulfonyloxy)thiazolo[3,2-a]pyrimidin-2-yl]piperidine-1-carboxylate (intermediate 5) and 2,7-dimethyl-5-(4,4,5,5-tetramethyl-1,3,2-dioxaborolan-2-yl)oxazolo[5,4-b]pyridine (boronic ester 6-9) gave tert-butyl ((3R,4R)-4-[7-(7-dimethyloxazolo[5,4-b]pyridinpyridin-5-yl)-5-oxo-thiazolo[3,2-a]pyrimidin-2-yl]-]-3-fluoro-piperidine-1-carboxylate.

Step 2: A deprotection using the general procedure 2, gave the title compound 7-(2,7-dimethyloxazolo[5,4-b]pyridin-5-yl)-2-[(3R,4R)-3-fluoro-4-piperidyl]]thiazolo[3,2-a]pyrimidin-5-one. MS (ES+) m/z: 400.2 [(M+H)+].

Examples 45 & 46

7-(8-methoxy-2-methyl-imidazo[1,2-b]pyridazin-6-yl)-2-[(3S,4R)-3-fluoro-4-piperidyl]thiazolo[3,2-a]pyrimidin-5-one and 7-(8-methoxy-2-methyl-imidazo[1,2-b]pyridazin-6-yl)-2-[(3R,4S)-3-fluoro-4-piperidyl]thiazolo[3,2-a]pyrimidin-5-one

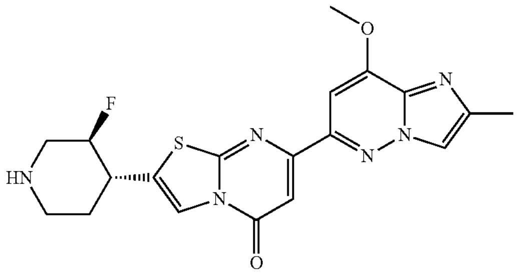

and

-continued

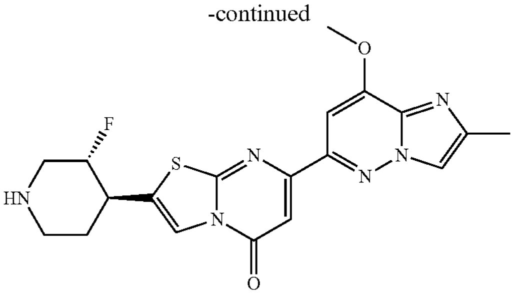

Step 1: Using the general procedure 1, separately, a cross coupling reaction between tert-butyl (3S,4R)-3-fluoro-4-[5-oxo-7-(p-tolylsulfonyloxy)thiazolo[3,2-a]pyrimidin-2-yl]piperidine-1-carboxylate or tert-butyl (3R,4S)-3-fluoro-4-[5-oxo-7-(p-tolylsulfonyloxy)thiazolo[3,2-a]pyrimidin-2-yl]piperidine-1-carboxylate (intermediates 5-18) and 8-methoxy-2-methyl-6-(4,4,5,5-tetramethyl-1,3,2-dioxaborolan-2-yl)imidazo[1,2-b]pyridazine (boronic ester 6-6) gave (3S,4R)-3-fluoro-4-[7-(8-methoxy-2-methyl-imidazo[1,2-b]pyridazin-6-yl)-5-oxo-thiazolo[3,2-a]pyrimidin-2-yl]piperidine-1-carboxylate and (3R,4S)-3-fluoro-4-[7-(8-methoxy-2-methyl-imidazo[1,2-b]pyridazin-6-yl)-5-oxo-thiazolo[3,2-a]pyrimidin-2-yl]piperidine-1-carboxylate respectively.

Step 2: A deprotection using the general procedure 2, gave separately the title compounds 7-(8-methoxy-2-methyl-imidazo[1,2-b]pyridazin-6-yl)-2-[(3S,4R)-3-fluoro-4-piperidyl]thiazolo[3,2-a]pyrimidin-5-one and 7-(8-methoxy-2-methyl-imidazo[1,2-b]pyridazin-6-yl)-2-[(3R,4S)-3-fluoro-4-piperidyl]thiazolo[3,2-a]pyrimidin-5-one respectively. MS (ES+) m/z: 415.2 [(M+H)+] for each enantiomer. Optical rotation for the two enantiomers was measured in MeOH (20° C., 589 nm): Example 45 is (−)-enantiomer, optical rotation: −15°; Example 46 is (+)-enantiomer, optical rotation: +39°.

Examples 47 & 48

7-(2,8-dimethylimidazo[1,2-b]pyridazin-6-yl)-2-[rac-(1R,5S)-9-oxa-3-azabicyclo[3.3.1]nonan-7-yl]thiazolo[3,2-a]pyrimidin-5-one and 7-(2,8-dimethylimidazo[1,2-b]pyridazin-6-yl)-2-[rac-(1S,5R)-9-oxa-3-azabicyclo[3.3.1]nonan-7-yl]thiazolo[3,2-a]pyrimidin-5-one

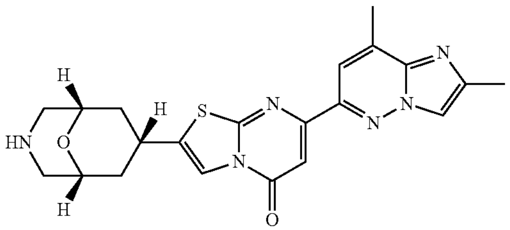

and

-continued

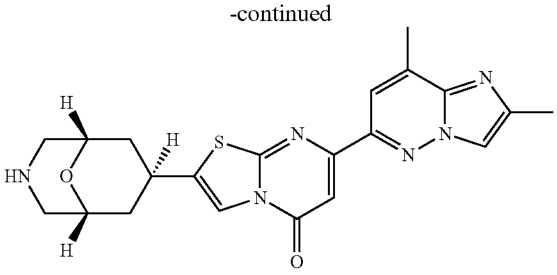

Using the general procedure 1, a cross coupling reaction between the intermediates 5-20 and 2,8-dimethyl-6-(4,4,5,5-tetramethyl-1,3,2-dioxaborolan-2-yl)imidazo[1,2-b]pyridazine (boronic ester 6-1) followed by a deprotection of the Boc protective group, gave separately after column chromatography the title compounds 7-(2,8-dimethylimidazo[1,2-b]pyridazin-6-yl)-2-[rac-(1R,5S)-9-oxa-3-azabicyclo[3.3.1]nonan-7-yl]thiazolo[3,2-a]pyrimidin-5-one (71 mg) as light yellow solid MS (ES+) m/z: 423.1 [(M+H)+] as the first compound to elute (relative structure assigned by 1H-NMR spectroscopy) and 7-(2,8-dimethylimidazo[1,2-b]pyridazin-6-yl)-2-[rac-(1S,5R)-9-oxa-3-azabicyclo[3.3.1]nonan-7-yl]thiazolo[3,2-a]pyrimidin-5-one (68 mg) (2nd compound to elute, relative stereochemistry assigned by 1H-NMR spectroscopy) as a light yellow solid. MS (ES+) m/z: 423.1 [(M+H)+].

Examples 49 & 50

7-(8-methoxy-2-methyl-imidazo[1,2-b]pyridazin-6-yl)-2-[rac-(1R,5S)-9-oxa-3-azabicyclo[3.3.1]nonan-7-yl]thiazolo[3,2-a]pyrimidin-5-one and 7-(8-methoxy-2-methyl-imidazo[1,2-b]pyridazin-6-yl)-2-[rac-(1S,5R)-9-oxa-3-azabicyclo[3.3.1]nonan-7-yl]thiazolo[3,2-a]pyrimidin-5-one

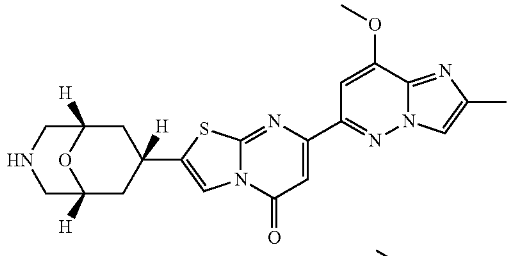

and

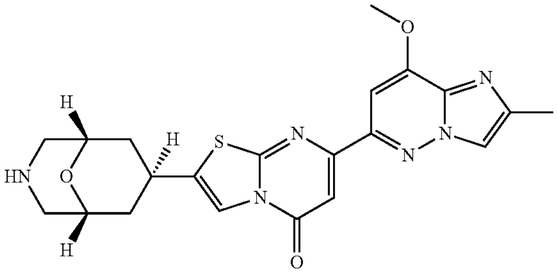

In analogy to the preparation of examples 47 and 48, from the intermediates 5-20 and 8-methoxy-2-methyl-6-(4,4,5,5-tetramethyl-1,3,2-dioxaborolan-2-yl)imidazo[1,2-b]pyridazine (boronic ester 6-6) the title compounds were obtained separately as an off white solid (96 mg and 86 mg respectively). MS (ES+) m/z: 439.1 [(M+H)+] for each of the meso compounds. Example 49 was the first one to elute from the column, and the relative stereochemistry was established by 1H NMR spectroscopy.

Examples 51 & 52

7-(8-methoxy-2-methyl-imidazo[1,2-b]pyridazin-6-yl)-2-[rac-(3R,4S)-3,4-difluoro-4-piperidyl]thiazolo[3,2-a]pyrimidin-5-one and 7-(8-methoxy-2-methyl-imidazo[1,2-b]pyridazin-6-yl)-2-[rac-(3S,4S)-3,4-difluoro-4-piperidyl]thiazolo[3,2-a]pyrimidin-5-one

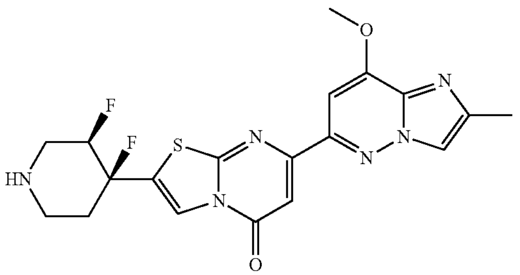

and

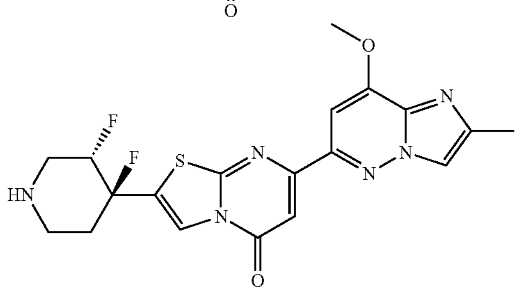

Step 1: Preparation of tert-butyl rac-(3R,4S)-4-(2-aminothiazol-5-yl)-3-fluoro-4-hydroxy-piperidine-1-carboxylate and tert-butyl rac-(3S,4S)-4-(2-aminothiazol-5-yl)-3-fluoro-4-hydroxy-piperidine-1-carboxylate

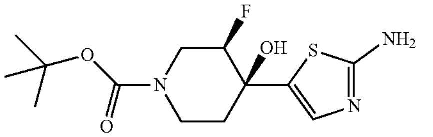

and

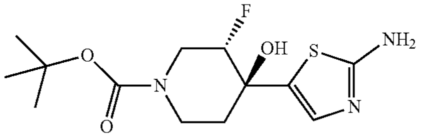

Thiazol-2-ylamine (2.4 g, 24 mmol, 1 eq.) were dissolved in dry THF (120 mL) and cooled to −75° C. A solution of n-BuLi (1.6 M in hexane, 30 mL, 48 mmol, 2 eq.) was added dropwise over 30 min and stirring was continued for 1 hour at −75° C. A solution of TMS-Cl (5.21 g, 6.13 mL, 48 mmol, 2 eq.) in dry THF (15 mL) was then added dropwise over 15 min. The dry-ice/bath was replaced by an ice-ethanol bath and stirred for 45 minutes between −30° C. and −20° C. The mixture was cooled to −75° C. again, and 1.6 M n-BuLi in hexane (15 mL, 24 mmol, 1 eq.) was added over 15 minutes and stirring continued for 15 min. at −75° C. A solution of 3-fluoro-4-keto-piperidine-1-carboxylic acid tert-butyl ester (5.21 g, 24 mmol, 1 eq) in THF (20 mL) was added over 20 min. After the addition, the dry-ice bath was removed and the reaction was allowed to warm over 45 minutes to 0° C. Stirred 30 minutes at 0-5° C. The reaction was quenched with sat.$NH_4Cl$-solution (150 mL) and diluted with water (100 mL) and extracted twice with Ethyl acetate (2×100 mL). The organic layers were washed with brine (1×100 mL), dried over $Na_2SO_4$, filtered off and concentrated in vacuo. The crude product was purified by silica gel chromatography with 2 M NH3/Methanol in DCM (gradient from 2-7%) to afford tert-butyl rac-(3R,4S)-4-(2-aminothiazol-5-yl)-3-fluoro-4-hydroxy-piperidine-1-carboxylate (3800 mg, 49.4%) as off-white solid. MS (ES+) m/z: 318.1 [$(M+H)^+$] and tert-butyl rac-(3S,4S)-4-(2-aminothiazol-5-yl)-3-fluoro-4-hydroxy-piperidine-1-carboxylate (1200 mg, 15.7%) as light brown foam. MS (ES+) m/z: 318.1 [$(M+H)^+$].

Step 2: Preparation of tert-butyl rac-(3R,4S)-3-fluoro-4-hydroxy-4-(7-hydroxy-5-oxo-thiazolo[3,2-a]pyrimidin-2-yl)piperidine-1-carboxylate

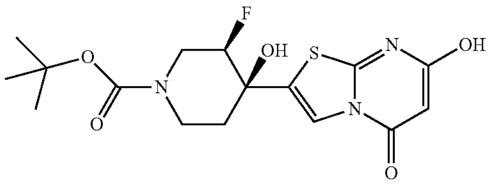 [SMILES: CC(C)(C)OC(=O)N1CC[C@@](O)(c2cn3c(=O)cc(O)nc3s2)[C@H](F)C1]

tert-butyl rac-(3R,4S)-4-(2-aminothiazol-5-yl)-3-fluoro-4-hydroxy-piperidine-1-carboxylate (1.2 g, 3.74 mmol, 1 eq) and malonic acid bis(2,4,6-trichlorophenyl)ester (1.91 g, 4.12 mmol, 1.1 eq.) were combined in toluene (20 mL). The suspension was stirred in an oil bath at 50° C. for 22 hours. The thick suspension was cooled in an ice-bath (0-5° C.) and diluted with tert. butyl methyl ether (20 mL). The resulting solid was collected by filtration and washed with cold tert. butyl methyl ether (3×10 mL). The filter cake was dried in vacuo at 45° C. to yield the title compound (1.23 g, 85.2%) as off-white solid. MS (ES−) m/z: 384.3 [$(M-H)^-$].

Step 3: Preparation of tert-butyl rac-(3R,4S)-3-fluoro-4-hydroxy-4-[5-oxo-7-(p-tolylsulfonyloxy)thiazolo[3,2-a]pyrimidin-2-yl]piperidine-1-carboxylate

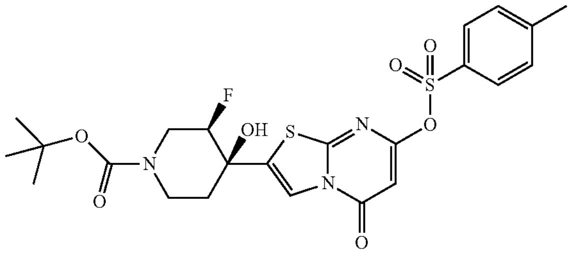 [SMILES: Cc1ccc(S(=O)(=O)Oc2cc(=O)n3cc([C@]4(O)CCN(C(=O)OC(C)(C)C)C[C@H]4F)sc3n2)cc1]

At room temperature, tert-butyl rac-(3R,4S)-3-fluoro-4-hydroxy-4-(7-hydroxy-5-oxo-thiazolo[3,2-a]pyrimidin-2-yl)piperidine-1-carboxylate (1.23 g, 3.19 mmol, 1 eq.) and trimethylamine (0.40 g, 3.99 mmol, 1.25 eq.) were combined with dichloromethane (15 mL) and Tosyl-Cl (0.67 g, 3.51 mmol, 1.1 eq.) was added and stirring was continued for 3 hours at RT, resulting in a suspension. Upon addition of DCM (100 mL) the solid was dissolved and washed with an aqueous solution of sat. $NaHCO_3$ (30 mL). The aqueous layer was back-extracted twice with DCM (50 mL). The combined organic layers were dried over $Na_2SO_4$, filtered off and concentrated in vacuo. The obtained solid residue was suspended in Heptane: tert. butyl methyl ether 3:1 (20 mL) for 10 minutes. Filtered off and washed with Heptane: tert. butyl methyl ether 3:1 (4×5 mL). The filter cake was dried in vacuo at 45° C. to yield the title compound (1.55 g, 90.0%) as an off-white solid. MS (ES+) m/z: 540.3 [(M+H)+].

Step 4: Preparation of tert-butyl rac-(3R,4S)-3-fluoro-4-hydroxy-4-[7-(8-methoxy-2-methyl-imidazo[1,2-b]pyridazin-6-yl)-5-oxo-thiazolo[3,2-a]pyrimidin-2-yl]piperidine-1-carboxylate

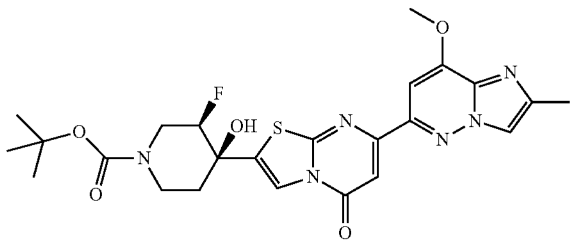 [SMILES: COc1cc(-c2cc(=O)n3cc([C@]4(O)CCN(C(=O)OC(C)(C)C)C[C@H]4F)sc3n2)nn2cc(C)nc12]

Using the general procedure 1, a cross coupling between tert-butyl rac-(3R,4S)-3-fluoro-4-hydroxy-4-[5-oxo-7-(p-tolylsulfonyloxy)thiazolo[3,2-a]pyrimidin-2-yl]piperidine-1-carboxylate and 8-methoxy-2-methyl-6-(4,4,5,5-tetramethyl-1,3,2-dioxaborolan-2-yl)imidazo[1,2-b]pyridazine (boronic ester 6-6) gave the title product (395 mg, 67%) as an off white solid. MS (ES+) m/z: 531.1 [$(M+H)^+$]

Step 5: Preparation of 7-(8-methoxy-2-methyl-imidazo[1,2-b]pyridazin-6-yl)-2-[rac-(3R,4S)-3,4-difluoro-4-piperidyl]thiazolo[3,2-a]pyrimidin-5-one 51 and 7-(8-methoxy-2-methyl-imidazo[1,2-b]pyridazin-6-yl)-2-[rac-(3S,4S)-3,4-difluoro-4-piperidyl]thiazolo[3,2-a]pyrimidin-5-one 52

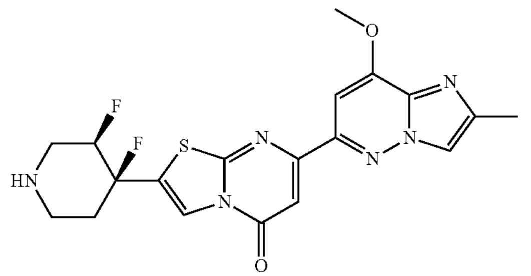

and

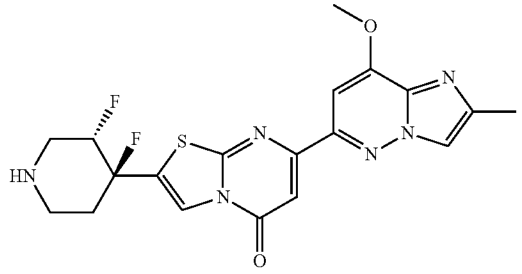

Step 5a) Fluorination: Dichloromethane, extra dry (5 mL) was placed and cooled in an ice-ethanol bath to ca. −10° C. Triethylamine trihydrofluoride (91 mg, 92 uL, 0.565 mmol, 1.5 eq.) was added and stirred for 2-3 min. XtalFluor-E® (172 mg, 0.754 mmol, 2 eq.; CAS Number: 63517-29-3) was added and stirred for 2-3 min. Then tert-butyl rac-(3R,4S)-3-fluoro-4-hydroxy-4-[7-(8-methoxy-2-methyl-imidazo[1,2-b]pyridazin-6-yl)-5-oxo-thiazolo[3,2-a]pyrimidin-2-yl]piperidine-1-carboxylate (200 mg, 0.377 mmol, 1 eq.) was added as solid and stirred for 10 minutes at −10° C. The ice-bath was removed and stirred overnight (17 hrs) at room temperature. The light yellowish solution was added to a stirred sat. $NaHCO_3$-solution (30 mL). The bi-layer mixture was stirred for 10 minutes. The organic layer was separated and the aqueous layer was back-extracted with DCM (2×20 mL). The combined organic layers were dried over $Na_2SO_4$, filtered off and concentrated in vacuo. The crude product was purified by $NH_2$-silica gel chromatography (20 g cartridge, Ethyl acetate in Heptane gradient from 15-100%). The obtained product (182 mg, 90%) as a mixture of diastereomers.

Step 5b) Deprotection: The previous mixture (step 5a) (374 mg, 0.702 mmol, 1 eq.) was dissolved in DCM (5 mL) and TFA (800 mg, 7.02 mmol, 10 eq) was added. After 2 hours at RT, the reaction mixture was evaporated in vacuo. The residue was dissolved in Methanol (5 mL) and purified by preparative HPLC. Column: AGILENT ECLIPSE XDB-C18, 250×30 mm, 7 micron. Eluent: Water (+0.05% HCOOH): Acetonitrile 85:15% to 50:50% in 8 min. Flow: 40 mL. (Triggered with UV 254 nm and ELSD). Product containing fractions were combined and evaporated in vacuo. The obtained products were dissolved in Methanol. Treated with 7 M $NH_3$/Methanol (3-4 mL) and aq. 28% $NH_{40}H$ (1 mL). Stirred for 10 minutes at room temperature. Addition of Isolute HM-N. Evaporated in vacuo to dryness and finally purified by silica gel chromatography with 2 M $NH_3$/Methanol in DCM increased the gradient from 2-7%.

51: 7-(8-methoxy-2-methyl-imidazo[1,2-b]pyridazin-6-yl)-2-[rac-(3R,4S)-3,4-difluoro-4-piperidyl]thiazolo[3,2-a]pyrimidin-5-one (53.7 mg, 17.7%). MS (ES+) m/z: 433.1 [$(M+H)^+$].

52: 7-(8-methoxy-2-methyl-imidazo[1,2-b]pyridazin-6-yl)-2-[rac-(3S,4S)-3,4-difluoro-4-piperidyl]thiazolo[3,2-a]pyrimidin-5-one (59.7 mg, 19.7%). MS (ES+) m z 433.1 [$(M+H)^+$].

Examples 53 & 54

7-(2,8-dimethylimidazo[1,2-b]pyridazin-6-yl)-2-[rac-(3R,4S)-3,4-difluoro-4-piperidyl]thiazolo[3,2-a]pyrimidin-5-one and 7-(2,8-dimethylimidazo[1,2-b]pyridazin-6-yl)-2-[rac-(3S,4S)-3,4-difluoro-4-piperidyl]thiazolo[3,2-a]pyrimidin-5-one

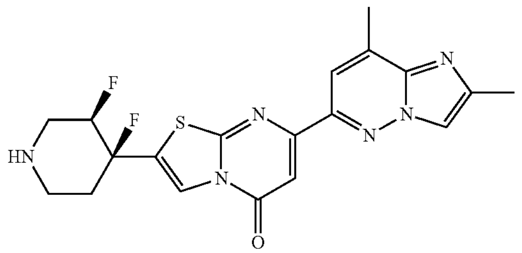

and

-continued

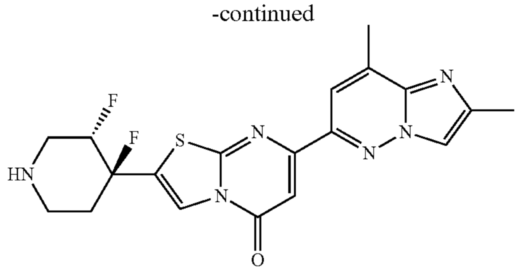

The compounds 53 and 54 were prepared in a similar manner as the compounds 51 and 52, with a difference on step 4, using 2,8-dimethyl-6-(4,4,5,5-tetramethyl-1,3,2-dioxaborolan-2-yl)imidazo[1,2-b]pyridazine as boronic ester (intermediate 6-1).

53: 7-(2,8-dimethylimidazo[1,2-b]pyridazin-6-yl)-2-[rac-(3R,4S)-3,4-difluoro-4-piperidyl]thiazolo[3,2-a]pyrimidin-5-one (69 mg) as light yellow solid. MS (ES+) m/z: 417.2 [(M+H)+].

54: 7-(2,8-dimethylimidazo[1,2-b]pyridazin-6-yl)-2-[rac-(3S,4S)-3,4-difluoro-4-piperidyl]thiazolo[3,2-a]pyrimidin-5-one (75 mg) as light yellow solid. MS (ES+) m/z: 417.2 [(M+H)+].

Example 55

7-(2,8-dimethylimidazo[1,2-b]pyridazin-6-yl)-2-[rac-(1S,5R)-3-azabicyclo[3.1.0]hexan-6-yl]thiazolo[3,2-a]pyrimidin-5-one

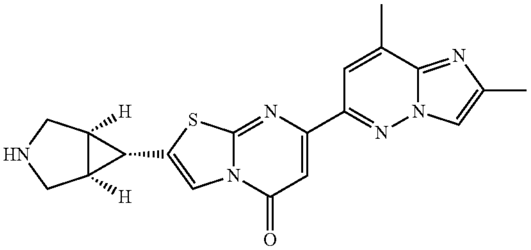 [SMILES: Cc1cn2nc(-c3cc(=O)n4cc([C@H]5[C@@H]6CNC[C@@H]65)sc4n3)cc(C)c2n1]

Step 1: Using the general procedure 1, a cross coupling reaction between (1R,5S)-6-(5-keto-7-tosyloxy-thiazolo[3,2-a]pyrimidin-2-yl)-3-azabicyclo[3.1.0]hexane-3-carboxylic acid benzyl ester (intermediate 5-21) and 2,8-dimethyl-6-(4,4,5,5-tetramethyl-1,3,2-dioxaborolan-2-yl)imidazo[1,2-b]pyridazine (boronic ester 1) gave tert-butyl 4-[7-(2,8-dimethylimidazo[1,2-b]pyridazin-6-yl)-5-oxo-thiazolo[3,2-a]pyrimidin-2-yl]-4-hydroxy-piperidine-1-carboxylate (76 mg, 59% yield) as a light yellow solid. MS (ES+) m/z: 513.4 $[(M+H)^+]$.

Step 2: A deprotection using the general procedure 3, gave 2-[(1R,5S)-3-azabicyclo[3.1.0]hexan-6-yl]-7-(2,8-dimethylimidazo[1,2-b]pyridazin-6-yl)thiazolo[3,2-a]pyrimidin-5-one (56 mg, 75% yield) as a white lyophilized powder. MS (ES+) m/z: 379.3 $[(M+H)^+]$.

Examples 56, 57, 58 and 59

7-(8-methoxy-2-methyl-imidazo[1,2-b]pyridazin-6-yl)-2-[(3R,4S)-3,4-difluoro-4-piperidyl]thiazolo[3,2-a]pyrimidin-5-one (56), 7-(8-methoxy-2-methyl-imidazo[1,2-b]pyridazin-6-yl)-2-[(3S,4S)-3,4-difluoro-4-piperidyl]thiazolo[3,2-a]pyrimidin-5-one (57), 7-(8-methoxy-2-methyl-imidazo[1,2-b]pyridazin-6-yl)-2-[(3R,4R)-3,4-difluoro-4-piperidyl]thiazolo[3,2-a]pyrimidin-5-one (58) and 7-(8-methoxy-2-methyl-imidazo[1,2-b]pyridazin-6-yl)-2-[(3S,4R)-3,4-difluoro-4-piperidyl]thiazolo[3,2-a]pyrimidin-5-one (59)

56

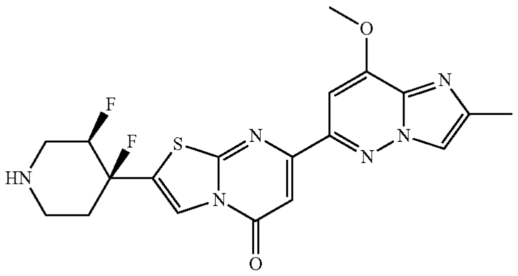

and

57

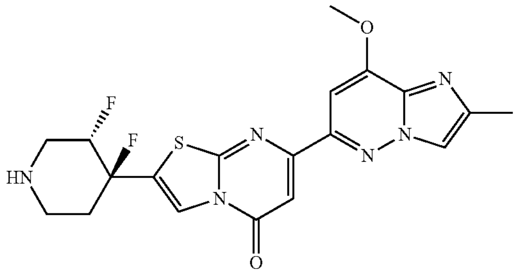

58

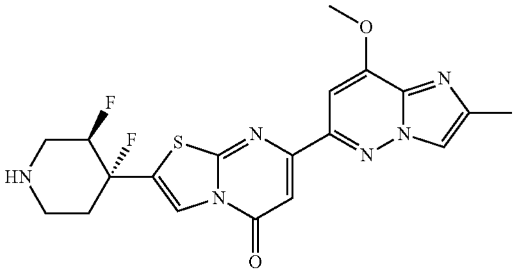

and

59

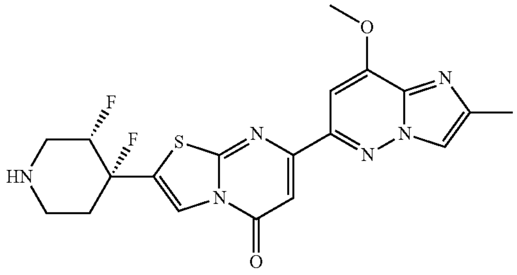

The four optically pure enantiomers 56-59 were obtained using similar procedures and sequences as for the preparation of the corresponding racemic compounds 51 and 52. Here we started from the optically pure tert-butyl (3R,4S)-

4-(2-aminothiazol-5-yl)-3-fluoro-4-hydroxy-piperidine-1-carboxylate and tert-butyl (3R,4R)-4-(2-aminothiazol-5-yl)-3-fluoro-4-hydroxy-piperidine-1-carboxylate (obtained from a chiral separation: Column chiral IG, 5 μm, 250×20 mm. SFC, 30% MeOH+0.2% DEA) Their absolute configuration was established upon derivatization to derivatives of known absolute stereochemistry. tert-Butyl (3R,4S)-4-(2-aminothiazol-5-yl)-3-fluoro-4-hydroxy-piperidine-1-carboxylate was used to produce the compounds 56 and 58 and tert-butyl (3R,4R)-4-(2-aminothiazol-5-yl)-3-fluoro-4-hydroxy-piperidine-1-carboxylate was used to produce compounds 57 and 59

56: 50 mg, off white solid. MS (ES+) m/z: 433.2 [$(M+H)^+$].

57: 40 mg, off white solid. MS (ES+) m/z: 433.2 [$(M+H)^+$].

58: 145 mg, off white solid. MS (ES+) m/z: 433.2 [$(M+H)^+$].

59: 125 mg, off white solid. MS (ES+) m/z: 433.2 [$(M+H)^+$].

Example 60

Homogeneous Time Resolved Fluorescence for HTT lowering

The HTRF assay was adapted from Weiss et al. (Analytical Biochemistry Volume 395, Issue 1, 1 Dec. 2009, Pages 8-15 and Analytical Biochemistry Volume 410, 2011, Pages 304-306) to cells from GENEAe020-A cell line (https://hpscreg.eu/cell-line/GENEAe020-A).

Compounds were tested for the effect of mutant HTT levels in Huntington patient human cells (GENEAe020-A cell line) using Homogeneous Time Resolved Fluorescence (HTRF) directed towards mutant HTT protein (mHTT). The GENEAe020-A cell line was derived by Genea Biocells from human blastocysts of HD donors. After assessing viability, cells were plated into 384 well collagen coated plates in growth media. Once cells adhered, media was removed and test compounds dissolved in DMSO were diluted with buffer solution and added to the adherent cells. Controls included experiments with no cells, DMSO with no compound, and Hsp90 inhibitor control. Cells were incubated with compounds and controls for 48 hours. Then, the cells were lysed and transferred to an assay plate containing HTRF labeled monoclonal antibodies developed by Paul Patterson (Ko et al., Brain Research Bulletin, Volume 56, Numbers 3 and 4, 2001, Pages 319-329) which recognize specific areas of the HTT protein. The terbium labeled "donor" antibody (2B7) binds to the N-terminus of the HTT protein and the Alexa488 labeled "acceptor" antibody (MW1) is specific for the polyglutamine region of the protein. Binding of the acceptor labeled antibody is more efficient for the extended polyglutamine repeats of mutant HTT protein which translates into a signal boost which enables the specific measurement of mutant HTT protein level. The HTRF donor and acceptor detection reagents were incubated with the cell lysate and the ratio between the signals of the two fluorophores is indicative of the relative quantities of mHTT.

The results of this assay are provided in Table 1. Table 1 provides the $EC_{50}$ (half maximal effective concentration) values for the reduction of mHTT obtained for particular examples of the present invention as measured by HTRF assay (data shown below is mean from three replicates).

TABLE 1

| Exam. | HTRF mHTT $EC_{50}$ (μM) | Exam. | HTRF mHTT $EC_{50}$ (μM) |
|---|---|---|---|
| 1 | 0.046 | 19 | 3.005 |
| 2 | 0.054 | 20 | 0.136 |
| 3 | 0.625 | 21 | 4.195 |
| 4 | 3.533 | 22 | 1.322 |
| 5 | 0.499 | 23 | 0.671 |
| 6 | 0.268 | 24 | 0.028 |
| 7 | 0.052 | 25 | 0.454 |
| 8 | 0.386 | 26 | 0.128 |
| 9 | 0.796 | 27 | 0.068 |
| 10 | 0.283 | 28 | 0.691 |
| 11 | 0.019 | 29 | 0.035 |
| 12 | 0.104 | 36 | 0.055 |
| 13 | 0.118 | 37 | 0.112 |
| 14 | 0.931 | 38 | 0.280 |
| 15 | 0.123 | 39 | 0.053 |
| 16 | 9.538 | 40 | 0.083 |
| 17 | 0.421 | 41 | 0.106 |
| 18 | 0.469 | 42- | 0.053 |
| 19 | 3.005 | 43 | 0.152 |
| 20 | 0.136 | 44 | 0.059 |
| 21 | 4.195 | 45 | 0.097 |
| 22 | 1.322 | 46 | 0.069 |
| 23 | 0.671 | 47 | 0.330 |
| 24 | 0.028 | 48 | 0.092 |
| 25 | 0.454 | 49 | 0.200 |
| 26 | 0.128 | 50 | 0.057 |
| 27 | 0.068 | 51 | 0.102 |
| 28 | 0.691 | 52 | 0.237 |
| 29 | 0.035 | 53 | 0.132 |
| 30 | 0.040 | 54 | 0.556 |
| 31 | 0.071 | 55 | 0.065 |
| 32 | 0.033 | 56 | 0.050 |
| 33 | 0.086 | 57 | 0.239 |
| 34 | 0.022 | 58 | 0.099 |
| 35 | 0.061 | 59 | 0.428 |

The invention claimed is:

1. A compound of formula (Ia)

(Ia)

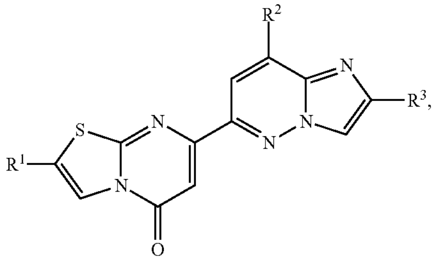

or a pharmaceutically acceptable salt thereof, wherein:

$R^1$ is selected from hydrogen, $C_{1-8}$ alkyl, $C_{3-10}$ cycloalkyl, $C_{6-10}$ aryl, 5-12 membered heteroaryl, and 3-12 membered heterocycloalkyl, wherein each of said $C_{3-10}$ cycloalkyl, $C_{6-10}$ aryl, 5-12 membered heteroaryl, and 3-12 membered heterocycloalkyl is optionally substituted with one, two, three, or four substituents independently selected from $R^4$;

$R^2$ is selected from hydrogen, halogen, cyano, amino, hydroxy, $C_{1-8}$ alkyl, $C_{2-8}$ alkenyl, $C_{1-8}$ alkoxy, $C_{1-8}$ haloalkyl, $C_{1-8}$ haloalkoxy, and $C_{3-10}$ cycloalkyl;

$R^3$ is selected from hydrogen, halogen, $C_{1-8}$ alkyl, and $C_{1-8}$ haloalkyl; and $R^4$ is selected from halogen, $C_{1-8}$ alkyl, 3-12 membered heterocycloalkyl, 3-12 membered heterocycloalkyl-$C_{1-8}$ alkyl, $C_{1-8}$ alkyl-3-12 membered heterocycloalkyl, 3-12 membered haloheterocycloalkyl, $C_{3-10}$ cycloalkyl, $C_{3-10}$ cycloalkyl-$C_{1-8}$ alkyl, $C_{1-8}$ alkyl-$C_{3-10}$ cycloalkyl, $C_{3-10}$ halocycloalkyl, $C_{3-10}$ cycloalkyl-amino, $C_{6-10}$ aryl, $C_{6-10}$ aryl-$C_{1-8}$ alkyl, $C_{1-8}$ alkyl-$C_{6-10}$ aryl, $C_{6-10}$ haloaryl, cyano, hydroxy, oxo, $C_{1-8}$ haloalkyl, $C_{1-8}$ alkyl-carbonyl, $C_{1-8}$ alkoxy, $C_{1-8}$ haloalkoxy, $C_{1-8}$ alkoxy-$C_{1-8}$ alkyl, $C_{1-8}$ alkoxy-carbonyl, amino, $C_{1-8}$ alkylamino, di ($C_{1-8}$ alkyl) amino, $C_{1-8}$ aminoalkyl, $C_{1-8}$ alkylamino-$C_{1-8}$ alkyl, di ($C_{1-8}$ alkyl) amino-$C_{1-8}$ alkyl, $C_{1-8}$ aminoalkyl-amino, $C_{1-8}$ alkoxy-$C_{1-8}$ alkylamino, $C_{1-8}$ alkyl-carbonyl-amino, $C_{1-8}$ alkoxy-carbonyl-amino, $C_{1-8}$ hydroxyalkyl, $C_{1-8}$ hydroxyalkoxy-$C_{1-8}$ alkyl, and $C_{1-8}$ hydroxyalkyl-amino;

provided that the compound of Formula (Ia) is not:

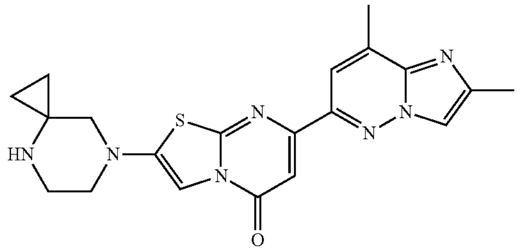 [SMILES: Cc1cn2nc(-c3cc(=O)n4cc(N5CCNC6(CC6)C5)sc4n3)cc(C)c2n1]

2-(4,7-diazaspiro[2.5]octan-7-yl)-7-(2,8-dimethylimidazo[1,2-b]pyridazin-6-yl)thiazolo[3,2-a]pyrimidin-5-one.

2. The compound of claim 1, wherein $R^1$ is 3-12 membered heterocycloalkyl optionally substituted with one or two substituents independently selected from $R^4$.

3. The compound of claim 1, wherein $R^1$ is selected from piperazin-1-yl, 1,2,3,6-tetrahydropyridin-4-yl, 4,7-diazaspiro[2.5]octan-7-yl, (8aS)-3,4,6,7,8,8a-hexahydro-1H-pyrrolo[1,2-a]pyrazin-2-yl, 3,8-diazabicyclo[3.2.1]octan-8-yl, (8aR)-3,4,6,7,8,8a-hexahydro-1H-pyrrolo[1,2-a]pyrazin-2-yl, (1S,4S)-2,5-diazabicyclo[2.2.1]heptan-2-yl, 2,3,3a,4,6,6a-hexahydro-1H-pyrrolo[3,4-c] pyrrol-5-yl, pyrrolidin-1-yl, 2,8-diazaspiro[4.5]decan-2-yl, (7R)-4-azaspiro[2.5]octan-7-yl, (7S)-4-azaspiro[2.5]octan-7-yl, 4-piperidyl, [rac-(1R,5S)-9-oxa-3-azabicyclo[3.3.1] nonan-7-yl], [rac-(1S,5R)-9-oxa-3-azabicyclo[3.3.1] nonan-7-yl, and [rac-(1S,5R)-3-azabicyclo[3.1.0]hexan-6-yl], each of which is optionally substituted with one or two substituents independently selected from $R^4$.

4. The compound of claim 1, wherein $R^1$ is selected from piperazin-1-yl, 4-piperidyl, pyrrolidin-1-yl, 1,2,3,6-tetrahydropyridin-4-yl, (7S)-4-azaspiro[2.5]octan-7-yl, (7R)-4-azaspiro[2.5]octan-7-yl, and (8aR)-3,4,6,7,8,8a-hexahydro-1H-pyrrolo[1,2-a]pyrazin-2-yl, each of which is optionally substituted with one or two substituents independently selected from $R^4$.

5. The compound of claim 1, wherein $R^2$ is selected from hydrogen, halogen, $C_{1-8}$ alkyl, $C_{2-8}$ alkenyl, $C_{1-8}$ alkoxy, $C_{1-8}$ haloalkyl, $C_{1-8}$ haloalkoxy, and $C_{3-10}$ cycloalkyl.

6. The compound of claim 1, wherein $R^2$ is selected from $C_{1-8}$ alkyl, $C_{1-8}$ haloalkyl, and $C_{1-8}$ alkoxy.

7. The compound of claim 1, wherein $R^2$ is selected from hydrogen, cyclopropyl, isopropenyl, fluoro, methyl, ethyl, isopropyl, trifluoromethyl, difluoromethoxy, and methoxy.

8. The compound of claim 1, wherein $R^2$ is selected from methyl, ethyl, trifluoromethyl, and methoxy.

9. The compound of claim 1, wherein $R^3$ is selected from $C_{1-8}$ alkyl and halogen.

10. The compound of claim 1, wherein $R^3$ is selected from methyl and chloro.

11. The compound of claim 1, wherein $R^4$ is selected from halogen, $C_{1-8}$ alkyl, and 3-12 membered heterocycloalkyl.

12. The compound of claim 1, wherein $R^4$ is selected from fluoro, methyl, and pyrrolidinyl.

13. The compound of claim 1, wherein the compound is selected from any one of the following compounds:

7-(2,8-dimethylimidazo[1,2-b]pyridazin-6-yl)-2-piperazin-1-yl-thiazolo[3,2-a]pyrimidin-5-one

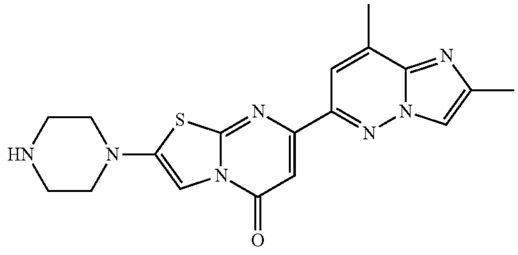 [SMILES: Cc1cn2nc(-c3cc(=O)n4cc(N5CCNCC5)sc4n3)cc(C)c2n1]

1

7-(2,8-dimethylimidazo[1,2-b]pyridazin-6-yl)-2-(1,2,3,6-tetrahydropyridin-4-yl)thiazolo[3,2-a]pyrimidin-5-one

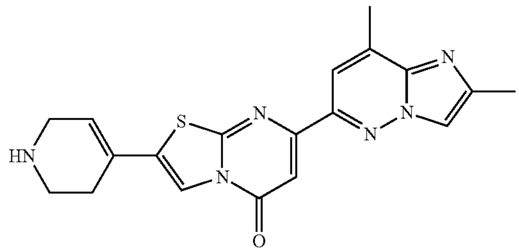 [SMILES: Cc1cn2nc(-c3cc(=O)n4cc(C5=CCNCC5)sc4n3)cc(C)c2n1]

2

-continued

| | | |
|---|---|---|
| 7-(2,8-dimethylimidazo[1,2-b]pyridazin-6-yl)-2-(3,3-dimethylpiperazin-1-yl)thiazolo[3,2-a]pyrimidin-5-one | 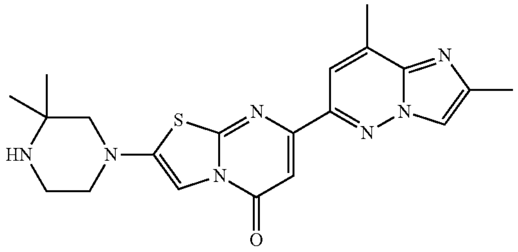 | 3 |
| 7-(2,8-dimethylimidazo[1,2-b]pyridazin-6-yl)-2-[(3S)-3-methylpiperazin-1-yl]thiazolo[3,2-a]pyrimidin-5-one | 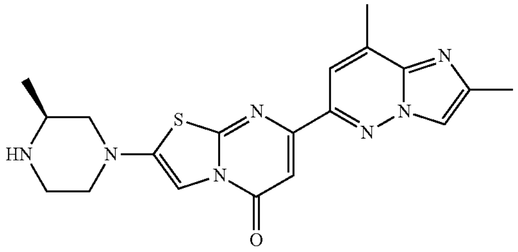 [SMILES: Cc1cn2nc(-c3cc(=O)n4cc(N5CCN[C@@H](C)C5)sc4n3)cc(C)c2n1] | 6 |
| 7-(2,8-dimethylimidazo[1,2-b]pyridazin-6-yl)-2-[(3R)-3-methylpiperazin-1-yl]thiazolo[3,2-a]pyrimidin-5-one | 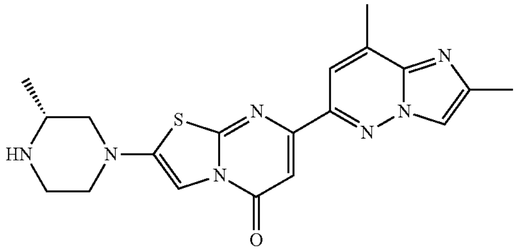 [SMILES: Cc1cn2nc(-c3cc(=O)n4cc(N5CCN[C@H](C)C5)sc4n3)cc(C)c2n1] | 7 |
| 7-(2,8-dimethylimidazo[1,2-b]pyridazin-6-yl)-2-(3,5-dimethylpiperazin-1-yl)thiazolo[3,2-a]pyrimidin-5-one | 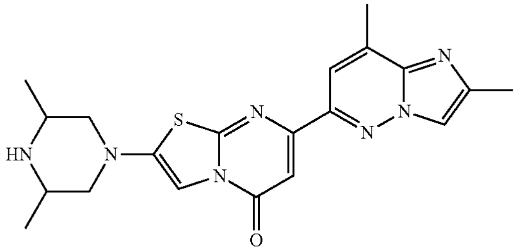 [SMILES: Cc1cn2nc(-c3cc(=O)n4cc(N5CC(C)NC(C)C5)sc4n3)cc(C)c2n1] | 8 |
| 7-(2,8-dimethylimidazo[1,2-b]pyridazin-6-yl)-2-[(8aS)-3,4,6,7,8,8a-hexahydro-1H-pyrrolo[1,2-a]pyrazin-2-yl]thiazolo[3,2-a]pyrimidin-5-one | 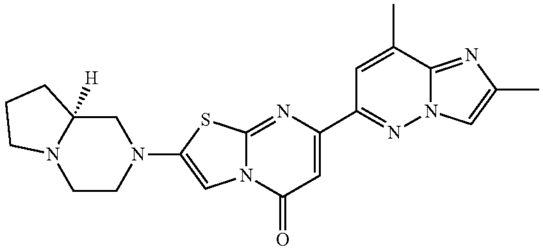 [SMILES: Cc1cn2nc(-c3cc(=O)n4cc(N5CCN6CCC[C@H]6C5)sc4n3)cc(C)c2n1] | 9 |
| 7-(2-methylimidazo[1,2-b]pyridazin-6-yl)-2-piperazin-1-yl-thiazolo[3,2-a]pyrimidin-5-one | 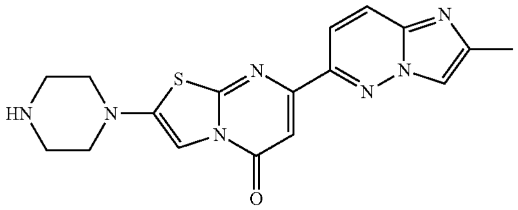 [SMILES: Cc1cn2nc(-c3cc(=O)n4cc(N5CCNCC5)sc4n3)ccc2n1] | 10 |

-continued

7-[2-methyl-8-(trifluoromethyl)imidazo[1,2-b]pyridazin-6-yl]-2-piperazin-1-yl-thiazolo[3,2-a]pyrimidin-5-one

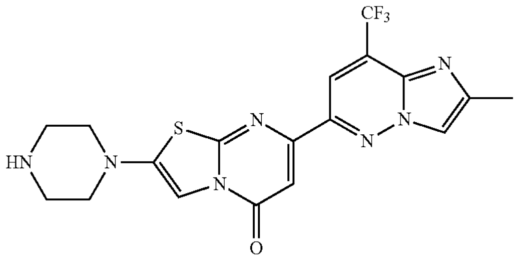 [SMILES: Cc1cn2nc(-c3cc(=O)n4cc(N5CCNCC5)sc4n3)cc(C(F)(F)F)c2n1]

11

7-(8-ethyl-2-methyl-imidazo[1,2-b]pyridazin-6-yl)-2-piperazin-1-yl-thiazolo[3,2-a]pyrimidin-5-one

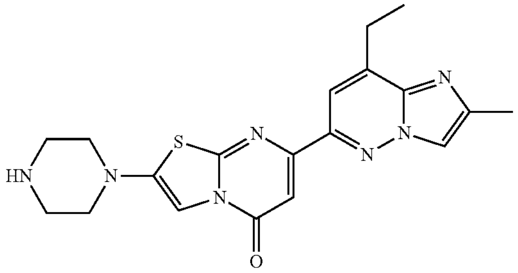

12

7-(8-methoxy-2-methyl-imidazo[1,2-b]pyridazin-6-yl)-2-piperazin-1-yl-thiazolo[3,2-a]pyrimidin-5-one

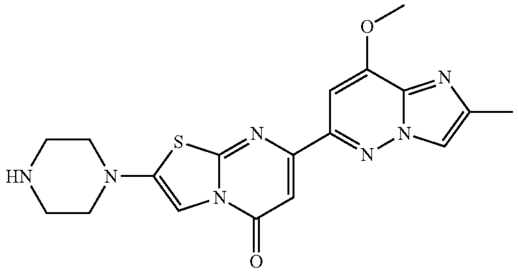 [SMILES: COc1cc(-c2cc(=O)n3cc(N4CCNCC4)sc3n2)nn2cc(C)nc12]

13

2-(3,8-diazabicyclo[3.2.1]octan-8-yl)-7-(2,8-dimethylimidazo[1,2-b]pyridazin-6-yl)thiazolo[3,2-a]pyrimidin-5-one

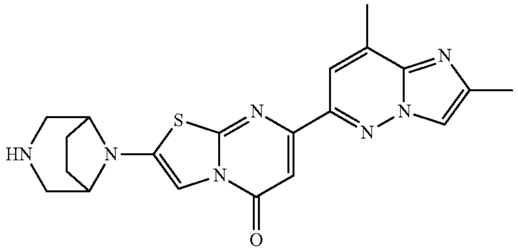 [SMILES: Cc1cn2nc(-c3cc(=O)n4cc(N5C6CCC5CNC6)sc4n3)cc(C)c2n1]

14

7-(2,8-dimethylimidazo[1,2-b]pyridazin-6-yl)-2-[(8aR)-3,4,6,7,8,8a-hexahydro-1H-pyrrolo[1,2-a]pyrazin-2-yl]thiazolo[3,2-a]pyrimidin-5-one

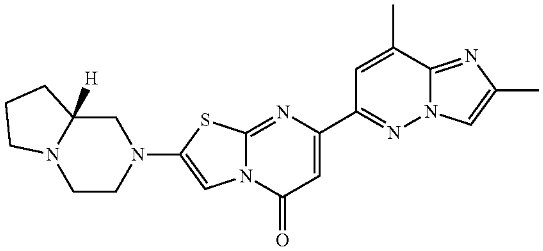 [SMILES: Cc1cn2nc(-c3cc(=O)n4cc(N5CCN6CCC[C@@H]6C5)sc4n3)cc(C)c2n1]

15

7-(2,8-dimethylimidazo[1,2-b]pyridazin-6-yl)-2-[(1S,4S)-2,5-diazabicyclo[2.2.1]heptan-2-yl]thiazolo[3,2-a]pyrimidin-5-one

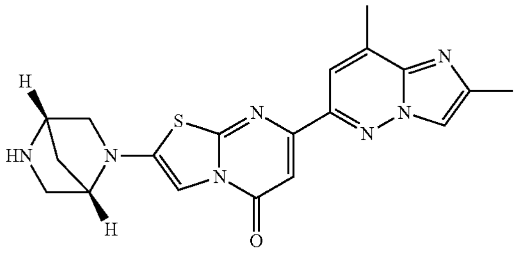 [SMILES: Cc1cn2nc(-c3cc(=O)n4cc(N5C[C@@H]6C[C@H]5CN6)sc4n3)cc(C)c2n1]

16

-continued 2-(2,3,3a,4,6,6a-hexahydro-1H-pyrrolo[3,4-c]pyrrol-5-yl)-7-(2,8-dimethylimidazo[1,2-b]pyridazin-6-yl)thiazolo[3,2-a]pyrimidin-5-one

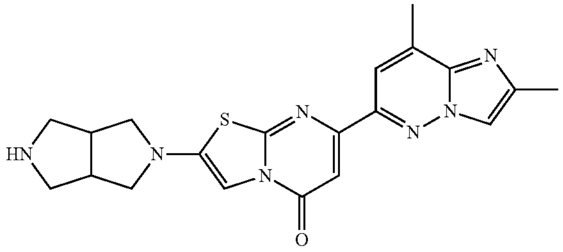 [SMILES: Cc1cn2nc(-c3cc(=O)n4cc(N5CC6CNCC6C5)sc4n3)cc(C)c2n1]

17

7-(8-cyclopropyl-2-methyl-imidazo[1,2-b]pyridazin-6-yl)-2-piperazin-1-yl-thiazolo[3,2-a]pyrimidin-5-one

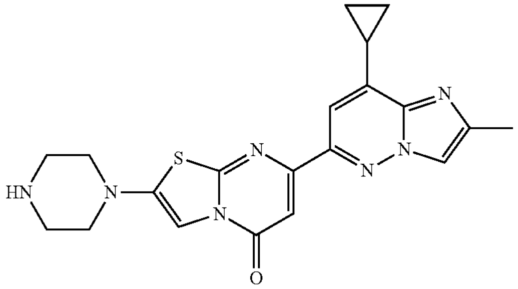 [SMILES: Cc1cn2nc(-c3cc(=O)n4cc(N5CCNCC5)sc4n3)cc(C3CC3)c2n1]

18

7-(8-isopropenyl-2-methyl-imidazo[1,2-b]pyridazin-6-yl)-2-piperazin-1-yl-thiazolo[3,2-a]pyrimidin-5-one

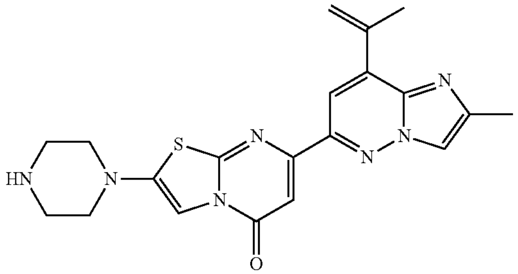 [SMILES: C=C(C)c1cc(-c2cc(=O)n3cc(N4CCNCC4)sc3n2)nn2cc(C)nc12]

19

7-(2,8-dimethylimidazo[1,2-b]pyridazin-6-yl)-2-[(3S)-3-pyrrolidin-1-ylpyrrolidin-1-yl]thiazolo[3,2-a]pyrimidin-5-one

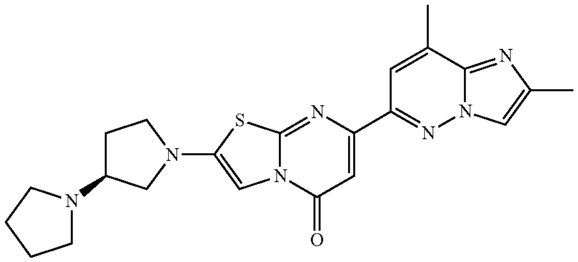 [SMILES: Cc1cn2nc(-c3cc(=O)n4cc(N5CC[C@H](N6CCCC6)C5)sc4n3)cc(C)c2n1]

21

2-(2,8-diazaspiro[4.5]decan-2-yl)-7-(2,8-dimethylimidazo[1,2-b]pyridazin-6-yl)thiazolo[3,2-a]pyrimidin-5-one

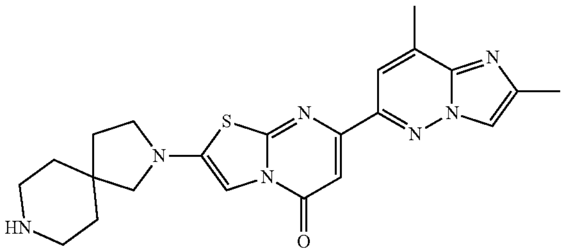 [SMILES: Cc1cn2nc(-c3cc(=O)n4cc(N5CCC6(CCNCC6)C5)sc4n3)cc(C)c2n1]

22

7-(8-isopropyl-2-methyl-imidazo[1,2-b]pyridazin-6-yl)-2-piperazin-1-yl-thiazolo[3,2-a]pyrimidin-5-one

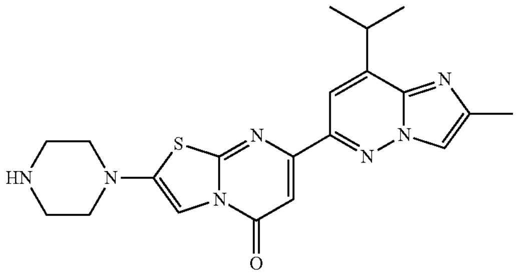 [SMILES: Cc1cn2nc(-c3cc(=O)n4cc(N5CCNCC5)sc4n3)cc(C(C)C)c2n1]

23

-continued 7-(2,8-dimethylimidazo[1,2-b]pyridazin-6-yl)-2-(4-piperidyl)thiazolo[3,2-a]pyrimidin-5-one

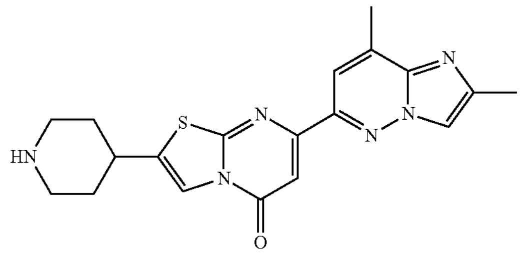

24

7-[2-methyl-8-(trifluoromethyl)imidazo[1,2-b]pyridazin-6-yl]-2-[(8aR)-3,4,6,7,8,8a-hexahydro-1H-pyrrolo[1,2-a]pyrazin-2-yl]thiazolo[3,2-a]pyrimidin-5-one

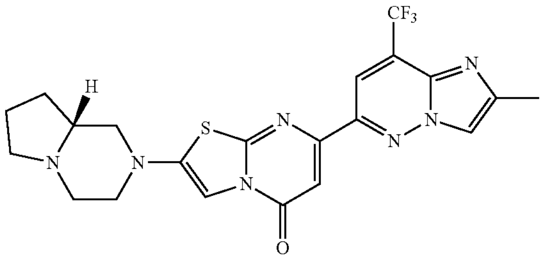 [SMILES: Cc1cn2nc(-c3cc(=O)n4cc(N5CCN6CCC[C@@H]6C5)sc4n3)cc(C(F)(F)F)c2n1]

25

7-(2,8-dimethylimidazo[1,2-b]pyridazin-6-yl)-2-(4-fluoro-4-piperidyl)thiazolo[3,2-a]pyrimidin-5-one

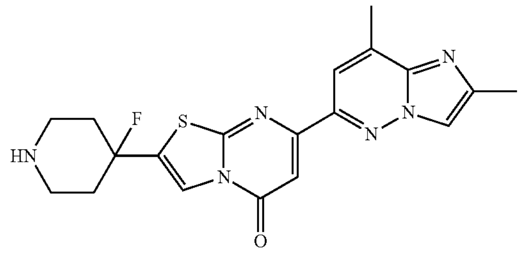 [SMILES: Cc1cn2nc(-c3cc(=O)n4cc(C5(F)CCNCC5)sc4n3)cc(C)c2n1]

26

7-[8-(difluoromethoxy)-2-methyl-imidazo[1,2-b]pyridazin-6-yl]-2-piperazin-1-yl-thiazolo[3,2-a]pyrimidin-5-one

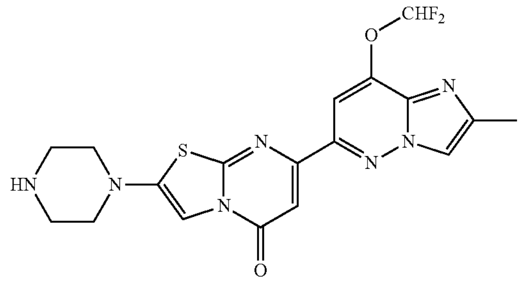 [SMILES: Cc1cn2nc(-c3cc(=O)n4cc(N5CCNCC5)sc4n3)cc(OC(F)F)c2n1]

27

7-(8-methoxy-2-methyl-imidazo[1,2-b]pyridazin-6-yl)-2-(4-piperidyl)thiazolo[3,2-a]pyrimidin-5-one

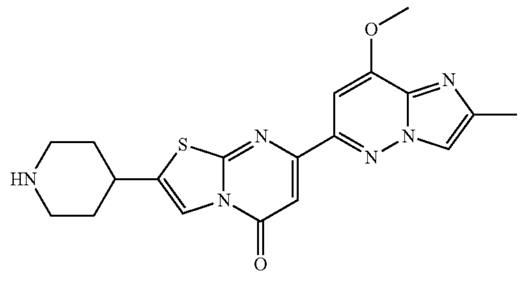

29

7-(2-chloro-8-methyl-imidazo[1,2-b]pyridazin-6-yl)-2-(4-piperidyl)thiazolo[3,2-a]pyrimidin-5-one

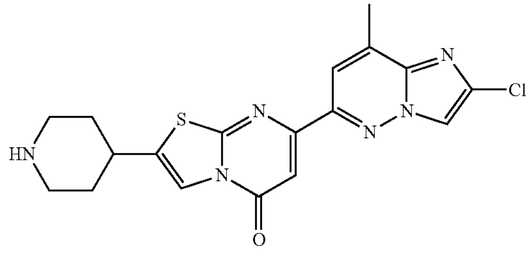 [SMILES: Cc1cc(-c2cc(=O)n3cc(C4CCNCC4)sc3n2)nn2cc(Cl)nc12]

31

-continued

| | | |
|---|---|---|
| 7-(2,8-dimethylimidazo[1,2-b]pyridazin-6-yl)-2-[(3R,4R)-3-fluoro-4-piperidyl]thiazolo[3,2-a]pyrimidin-5-one | 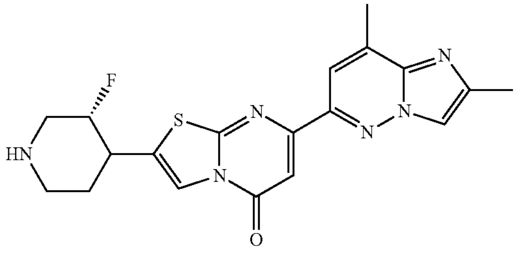 [SMILES: Cc1cn2nc(-c3cc(=O)n4cc(C5CCNC[C@@H]5F)sc4n3)cc(C)c2n1] | 32 |
| 7-(2,8-dimethylimidazo[1,2-b]pyridazin-6-yl)-2-[(3S,4S)-3-fluoro-4-piperidyl]thiazolo[3,2-a]pyrimidin-5-one | 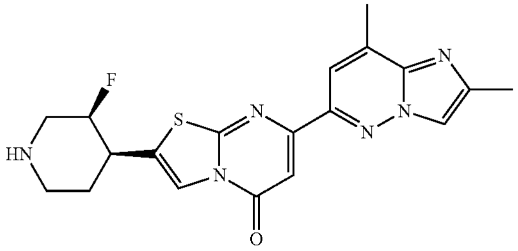 [SMILES: Cc1cn2nc(-c3cc(=O)n4cc([C@H]5CCNC[C@H]5F)sc4n3)cc(C)c2n1] | 33 |
| 7-(8-methoxy-2-methyl-imidazo[1,2-b]pyridazin-6-yl)-2-[(3R,4R)-3-fluoro-4-piperidyl]thiazolo[3,2-a]pyrimidin-5-one | 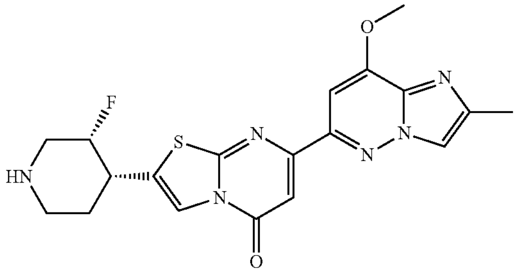 [SMILES: COc1cc(-c2cc(=O)n3cc([C@@H]4CCNC[C@@H]4F)sc3n2)nn2cc(C)nc12] | 34 |
| 7-(8-methoxy-2-methyl-imidazo[1,2-b]pyridazin-6-yl)-2-[(3S,4S)-3-fluoro-4-piperidyl]thiazolo[3,2-a]pyrimidin-5-one | 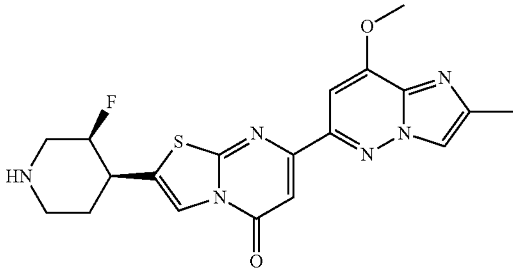 [SMILES: COc1cc(-c2cc(=O)n3cc([C@H]4CCNC[C@H]4F)sc3n2)nn2cc(C)nc12] | 35 |
| 7-(2,8-dimethylimidazo[1,2-b]pyridazin-6-yl)-2-[(7S)-4-azaspiro[2.5]octan-7-yl]thiazolo[3,2-a]pyrimidin-5-one | 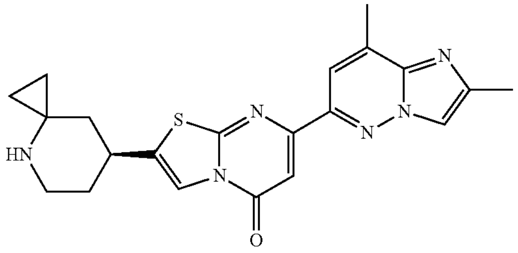 [SMILES: Cc1cn2nc(-c3cc(=O)n4cc([C@H]5CCNC6(CC6)C5)sc4n3)cc(C)c2n1] | 36 |
| 7-(2,8-dimethylimidazo[1,2-b]pyridazin-6-yl)-2-[(7R)-4-azaspiro[2.5]octan-7-yl]thiazolo[3,2-a]pyrimidin-5-one | 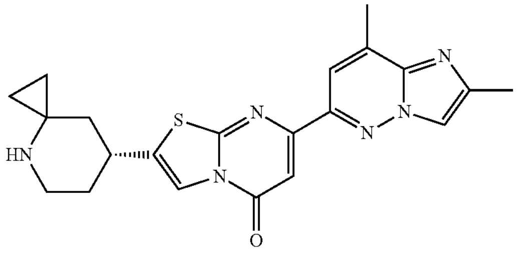 [SMILES: Cc1cn2nc(-c3cc(=O)n4cc([C@@H]5CCNC6(CC6)C5)sc4n3)cc(C)c2n1] | 37 |

-continued 7-(2,8-dimethylimidazo[1,2-b]pyridazin-6-yl)-2-[(3S,4R)-3-fluoro-4-piperidyl]thiazolo[3,2-a]pyrimidin-5-one

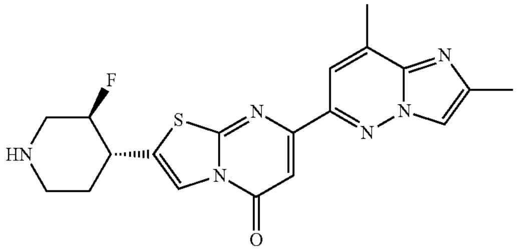 [SMILES: Cc1cn2nc(-c3cc(=O)n4cc([C@@H]5CCNC[C@H]5F)sc4n3)cc(C)c2n1]

38

7-(2,8-dimethylimidazo[1,2-b]pyridazin-6-yl)-2-[(3R,4S)-3-fluoro-4-piperidyl]thiazolo[3,2-a]pyrimidin-5-one

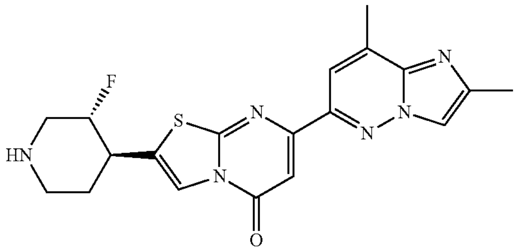 [SMILES: Cc1cn2nc(-c3cc(=O)n4cc([C@H]5CCNC[C@@H]5F)sc4n3)cc(C)c2n1]

39

7-(8-methoxy-2-methyl-imidazo[1,2-b]pyridazin-6-yl)-2-[(7R)-4-azaspiro[2.5]octan-7-yl]thiazolo[3,2-a]pyrimidin-5-one

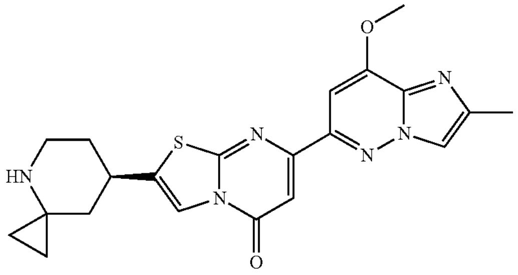 [SMILES: COc1cc(-c2cc(=O)n3cc([C@@H]4CCNC5(CC5)C4)sc3n2)nn2cc(C)nc12]

40

7-(8-methoxy-2-methyl-imidazo[1,2-b]pyridazin-6-yl)-2-[(7S)-4-azaspiro[2.5]octan-7-yl]thiazolo[3,2-a]pyrimidin-5-one

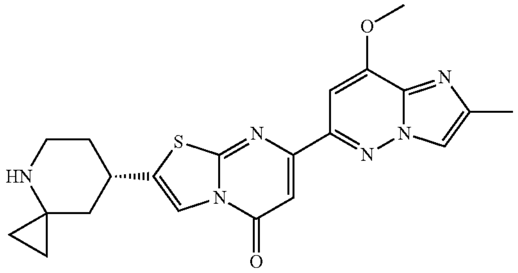 [SMILES: COc1cc(-c2cc(=O)n3cc([C@H]4CCNC5(CC5)C4)sc3n2)nn2cc(C)nc12]

41

2-(4-fluoro-4-piperidyl)-7-(8-methoxy-2-methyl-imidazo[1,2-b]pyridazin-6-yl)thiazolo[3,2-a]pyrimidin-5-one

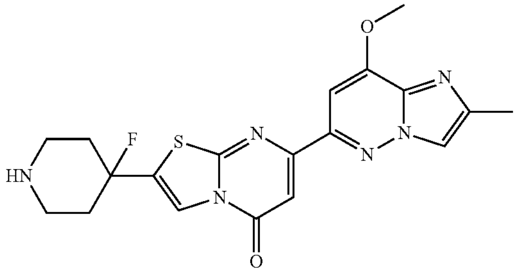 [SMILES: COc1cc(-c2cc(=O)n3cc(C4(F)CCNCC4)sc3n2)nn2cc(C)nc12]

42

7-(2-chloro-8-methyl-imidazo[1,2-b]pyridazin-6-yl)-2-[(3R,4R)-3-fluoro-4-piperidyl]thiazolo[3,2-a]pyrimidin-5-one

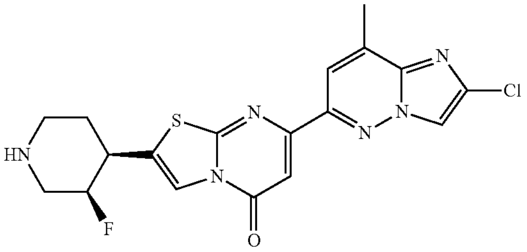 [SMILES: Cc1cc(-c2cc(=O)n3cc([C@@H]4CCNC[C@@H]4F)sc3n2)nn2cc(Cl)nc12]

43

-continued

| | | |
|---|---|---|
| 7-(8-methoxy-2-methyl-imidazo[1,2-b]pyridazin-6-yl)-2-[(3S,4R)-3-fluoro-4-piperidyl]thiazolo[3,2-a]pyrimidin-5-one | 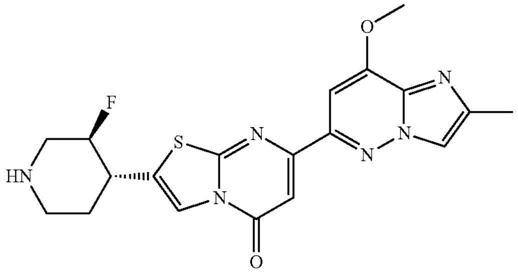 [SMILES: COc1cc(-c2cc(=O)n3cc([C@@H]4CCNC[C@H]4F)sc3n2)nn2cc(C)nc12] | 45 |
| 7-(8-methoxy-2-methyl-imidazo[1,2-b]pyridazin-6-yl)-2-[(3R,4S)-3-fluoro-4-piperidyl]thiazolo[3,2-a]pyrimidin-5-one | 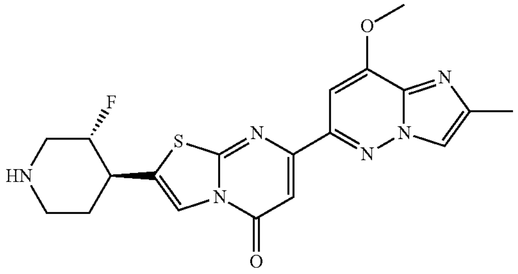 [SMILES: COc1cc(-c2cc(=O)n3cc([C@H]4CCNC[C@@H]4F)sc3n2)nn2cc(C)nc12] | 46 |

or a pharmaceutically acceptable salt thereof.

14. The compound of claim 1, wherein the compound is selected from any one of the following compounds:

| | | |
|---|---|---|
| 7-(2,8-dimethylimidazo[1,2-b]pyridazin-6-yl)-2-piperazin-1-yl-thiazolo[3,2-a]pyrimidin-5-one | 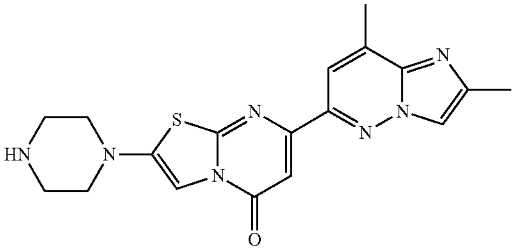 | 1 |
| 7-(2,8-dimethylimidazo[1,2-b]pyridazin-6-yl)-2-(1,2,3,6-tetrahydropyridin-4-yl)thiazolo[3,2-a]pyrimidin-5-one | 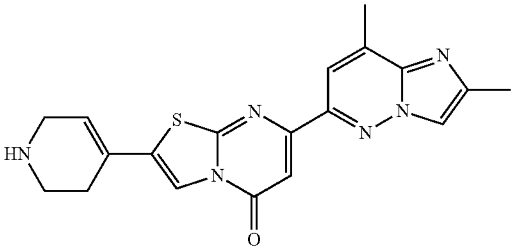 [SMILES: Cc1cn2nc(-c3cc(=O)n4cc(C5=CCNCC5)sc4n3)cc(C)c2n1] | 2 |
| 7-(2,8-dimethylimidazo[1,2-b]pyridazin-6-yl)-2-[(3R)-3-methylpiperazin-1-yl]thiazolo[3,2-a]pyrimidin-5-one | 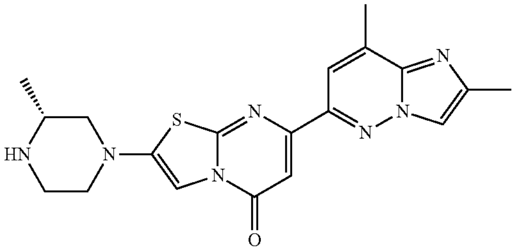 [SMILES: Cc1cn2nc(-c3cc(=O)n4cc(N5CCN[C@H](C)C5)sc4n3)cc(C)c2n1] | 7 |

-continued

| | | |
|---|---|---|
| 7-[2-methyl-8-(trifluoromethyl)imidazo[1,2-b]pyridazin-6-yl]-2-piperazin-1-yl-thiazolo[3,2-a]pyrimidin-5-one | 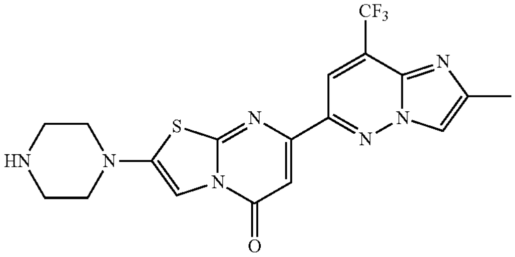 [SMILES: Cc1cn2nc(-c3cc(=O)n4cc(N5CCNCC5)sc4n3)cc(C(F)(F)F)c2n1] | 11 |
| 7-(8-ethyl-2-methyl-imidazo[1,2-b]pyridazin-6-yl)-2-piperazin-1-yl-thiazolo[3,2-a]pyrimidin-5-one | 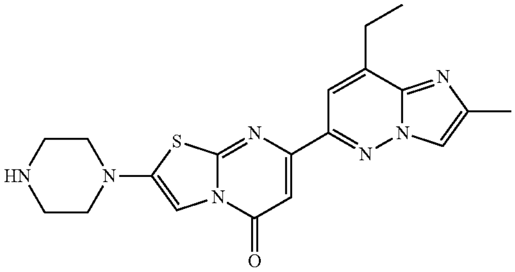 | 12 |
| 7-(8-methoxy-2-methyl-imidazo[1,2-b]pyridazin-6-yl)-2-piperazin-1-yl-thiazolo[3,2-a]pyrimidin-5-one | 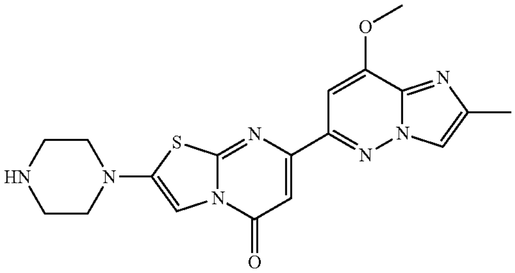 [SMILES: COc1cc(-c2cc(=O)n3cc(N4CCNCC4)sc3n2)nn2cc(C)nc12] | 13 |
| 7-(2,8-dimethylimidazo[1,2-b]pyridazin-6-yl)-2-[(8aR)-3,4,6,7,8,8a-hexahydro-1H-pyrrolo[1,2-a]pyrazin-2-yl]thiazolo[3,2-a]pyrimidin-5-one | 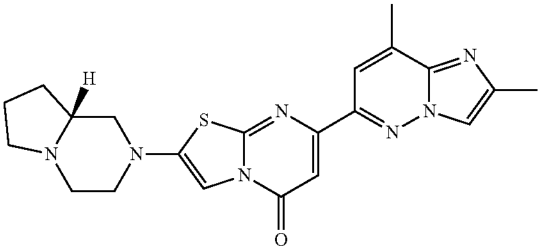 [SMILES: Cc1cn2nc(-c3cc(=O)n4cc(N5CCN6CCC[C@@H]6C5)sc4n3)cc(C)c2n1] | 15 |
| 7-(2,8-dimethylimidazo[1,2-b]pyridazin-6-yl)-2-(4-piperidyl)thiazolo[3,2-a]pyrimidin-5-one | 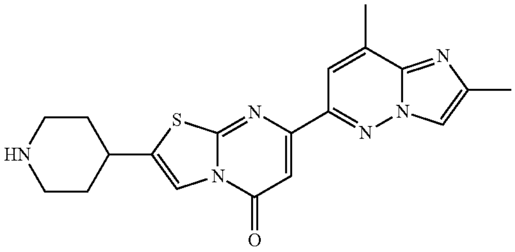 | 24 |
| 7-(2,8-dimethylimidazo[1,2-b]pyridazin-6-yl)-2-(4-fluoro-4-piperidyl)thiazolo[3,2-a]pyrimidin-5-one | 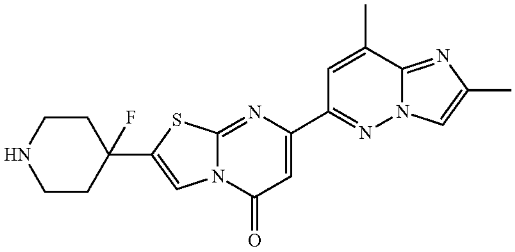 [SMILES: Cc1cn2nc(-c3cc(=O)n4cc(C5(F)CCNCC5)sc4n3)cc(C)c2n1] | 26 |

-continued

| | | |
|---|---|---|
| 7-[8-(difluoromethoxy)-2-methyl-imidazo[1,2-b]pyridazin-6-yl]-2-piperazin-1-yl-thiazolo[3,2-a]pyrimidin-5-one | 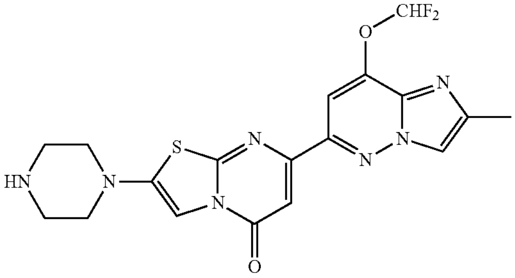 [SMILES: Cc1cn2nc(-c3cc(=O)n4cc(N5CCNCC5)sc4n3)cc(OC(F)F)c2n1] | 27 |
| 7-(8-methoxy-2-methyl-imidazo[1,2-b]pyridazin-6-yl)-2-(4-piperidyl)thiazolo[3,2-a]pyrimidin-5-one | 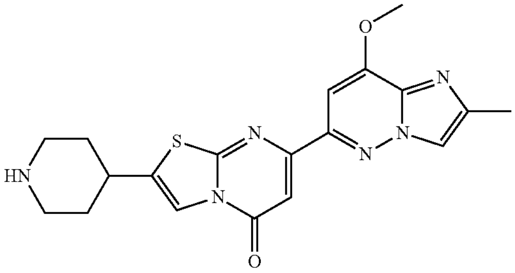 | 29 |
| 7-(2-chloro-8-methyl-imidazo[1,2-b]pyridazin-6-yl)-2-(4-piperidyl)thiazolo[3,2-a]pyrimidin-5-one | 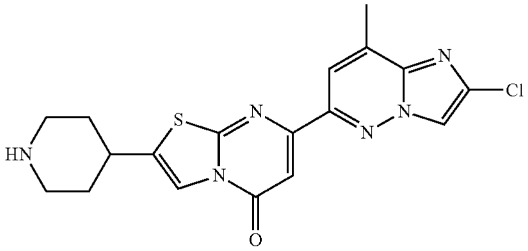 [SMILES: Cc1cc(-c2cc(=O)n3cc(C4CCNCC4)sc3n2)nn2cc(Cl)nc12] | 31 |
| 7-(2,8-dimethylimidazo[1,2-b]pyridazin-6-yl)-2-[(3R,4R)-3-fluoro-4-piperidyl]thiazolo[3,2-a]pyrimidin-5-one | 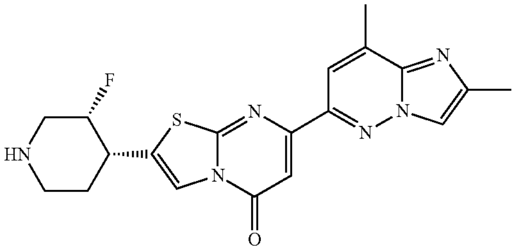 | 32 |
| 7-(2,8-dimethylimidazo[1,2-b]pyridazin-6-yl)-2-[(3S,4S)-3-fluoro-4-piperidyl]thiazolo[3,2-a]pyrimidin-5-one | 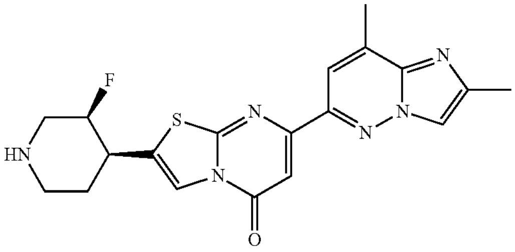 [SMILES: Cc1cn2nc(-c3cc(=O)n4cc([C@H]5CCNC[C@H]5F)sc4n3)cc(C)c2n1] | 33 |
| 7-(8-methoxy-2-methyl-imidazo[1,2-b]pyridazin-6-yl)-2-[(3R,4R)-3-fluoro-4-piperidyl]thiazolo[3,2-a]pyrimidin-5-one | 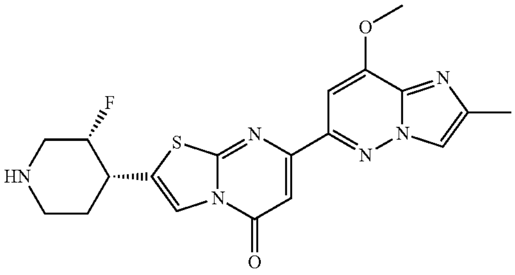 [SMILES: COc1cc(-c2cc(=O)n3cc([C@@H]4CCNC[C@@H]4F)sc3n2)nn2cc(C)nc12] | 34 |

-continued 7-(8-methoxy-2-methyl-imidazo[1,2-b]pyridazin-6-yl)-2-[(3S,4S)-3-fluoro-4-piperidyl]thiazolo[3,2-a]pyrimidin-5-one

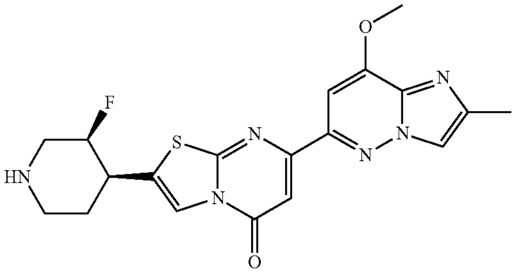 [SMILES: COc1cc(-c2cc(=O)n3cc([C@H]4CCNC[C@H]4F)sc3n2)nn2cc(C)nc12]

35

7-(2,8-dimethylimidazo[1,2-b]pyridazin-6-yl)-2-[(7S)-4-azaspiro[2.5]octan-7-yl]thiazolo[3,2-a]pyrimidin-5-one

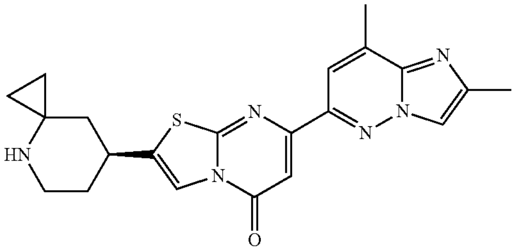 [SMILES: Cc1cn2nc(-c3cc(=O)n4cc([C@H]5CCNC6(CC6)C5)sc4n3)cc(C)c2n1]

36

7-(2,8-dimethylimidazo[1,2-b]pyridazin-6-yl)-2-[(7R)-4-azaspiro[2.5]octan-7-yl]thiazolo[3,2-a]pyrimidin-5-one

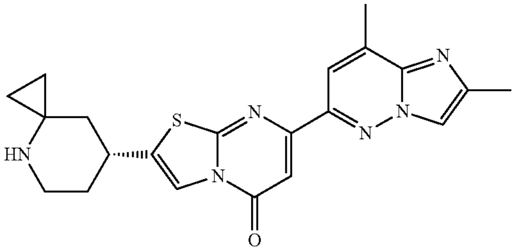

37

7-(2,8-dimethylimidazo[1,2-b]pyridazin-6-yl)-2-[(3S,4R)-3-fluoro-4-piperidyl]thiazolo[3,2-a]pyrimidin-5-one

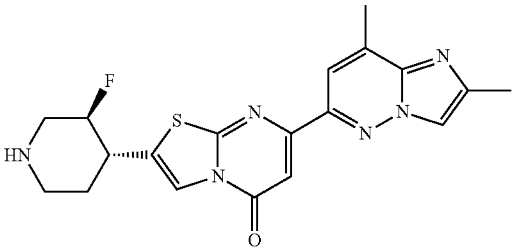 [SMILES: Cc1cn2nc(-c3cc(=O)n4cc([C@@H]5CCNC[C@H]5F)sc4n3)cc(C)c2n1]

38

7-(2,8-dimethylimidazo[1,2-b]pyridazin-6-yl)-2-[(3R,4S)-3-fluoro-4-piperidyl]thiazolo[3,2-a]pyrimidin-5-one

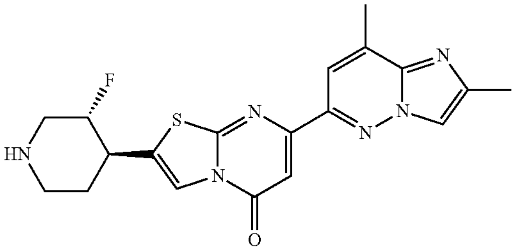 [SMILES: Cc1cn2nc(-c3cc(=O)n4cc([C@H]5CCNC[C@@H]5F)sc4n3)cc(C)c2n1]

39

7-(8-methoxy-2-methyl-imidazo[1,2-b]pyridazin-6-yl)-2-[(7S)-4-azaspiro[2.5]octan-7-yl]thiazolo[3,2-a]pyrimidin-5-one

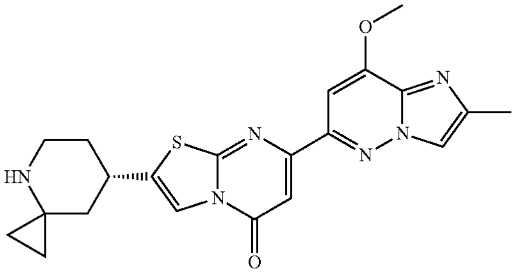 [SMILES: COc1cc(-c2cc(=O)n3cc([C@H]4CCNC5(CC5)C4)sc3n2)nn2cc(C)nc12]

40

-continued

| | | |
|---|---|---|
| 7-(8-methoxy-2-methyl-imidazo[1,2-b]pyridazin-6-yl)-2-[(7R)-4-azaspiro[2.5]octan-7-yl]thiazolo[3,2-a]pyrimidin-5-one | 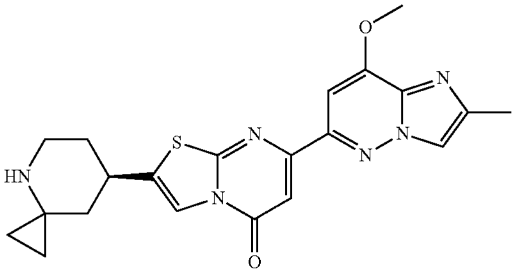 [SMILES: COc1cc(-c2cc(=O)n3cc([C@@H]4CCNC5(CC5)C4)sc3n2)nn2cc(C)nc12] | 41 |
| 2-(4-fluoro-4-piperidyl)-7-(8-methoxy-2-methyl-imidazo[1,2-b]pyridazin-6-yl)thiazolo[3,2-a]pyrimidin-5-one | 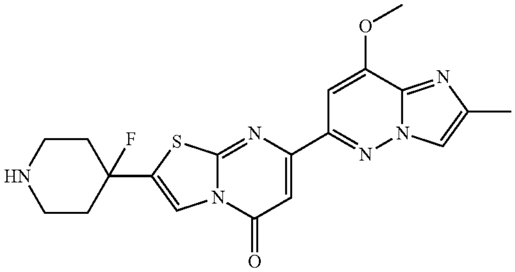 [SMILES: COc1cc(-c2cc(=O)n3cc(C4(F)CCNCC4)sc3n2)nn2cc(C)nc12] | 42 |
| 7-(8-methoxy-2-methyl-imidazo[1,2-b]pyridazin-6-yl)-2-[(3S,4R)-3-fluoro-4-piperidyl]thiazolo[3,2-a]pyrimidin-5-one | 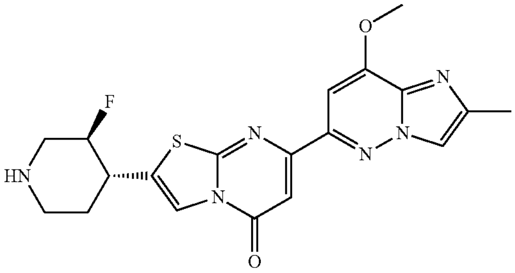 [SMILES: COc1cc(-c2cc(=O)n3cc([C@@H]4CCNC[C@H]4F)sc3n2)nn2cc(C)nc12] | 45 |
| 7-(8-methoxy-2-methyl-imidazo[1,2-b]pyridazin-6-yl)-2-[(3R,4S)-3-fluoro-4-piperidyl]thiazolo[3,2-a]pyrimidin-5-one | 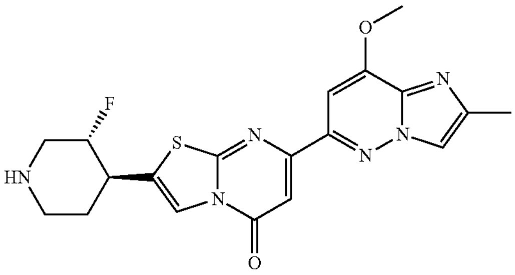 [SMILES: COc1cc(-c2cc(=O)n3cc([C@H]4CCNC[C@@H]4F)sc3n2)nn2cc(C)nc12] | 46 |

or a pharmaceutically acceptable salt thereof.

15. The compound of claim 1, selected from any one of the following compounds:

| | | |
|---|---|---|
| 7-(2,8-dimethylimidazo[1,2-b]pyridazin-6-yl)-2-[rac-(1R,5S)-9-oxa-3-azabicyclo[3.3.1]nonan-7-yl]thiazolo[3,2-a]pyrimidin-5-one | 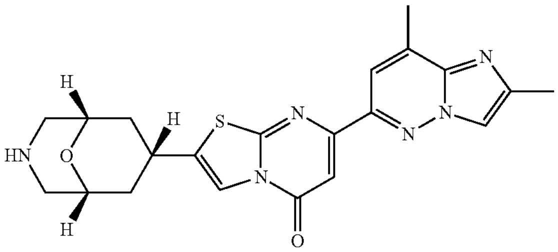 [SMILES: Cc1cn2nc(-c3cc(=O)n4cc([C@H]5C[C@H]6CNC[C@@H](C5)O6)sc4n3)cc(C)c2n1] | 47 |

-continued 7-(2,8-dimethylimidazo[1,2-b]pyridazin-6-yl)-2-[rac-(1S,5R)-9-oxa-3-azabicyclo[3.3.1]nonan-7-yl]thiazolo[3,2-a]pyrimidin-5-one

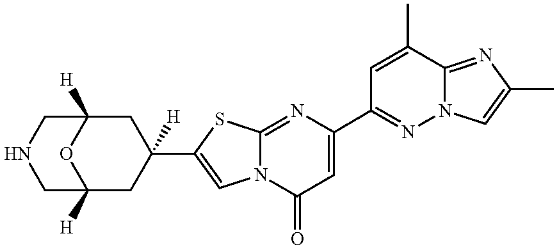 [SMILES: Cc1cn2nc(-c3cc(=O)n4cc([C@@H]5C[C@H]6CNC[C@@H](C5)O6)sc4n3)cc(C)c2n1]

48

7-(8-methoxy-2-methyl-imidazo[1,2-b]pyridazin-6-yl)-2-[rac-(1R,5S)-9-oxa-3-azabicyclo[3.3.1]nonan-7-yl]thiazolo[3,2-a]pyrimidin-5-one

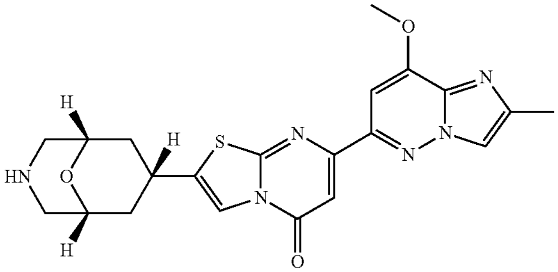 [SMILES: COc1cc(-c2cc(=O)n3cc([C@H]4C[C@H]5CNC[C@@H](C4)O5)sc3n2)nn2cc(C)nc12]

49

7-(8-methoxy-2-methyl-imidazo[1,2-b]pyridazin-6-yl)-2-[rac-(1S,5R)-9-oxa-3-azabicyclo[3.3.1]nonan-7-yl]thiazolo[3,2-a]pyrimidin-5-one

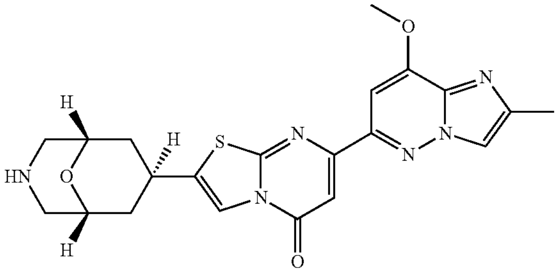 [SMILES: COc1cc(-c2cc(=O)n3cc([C@@H]4C[C@H]5CNC[C@@H](C4)O5)sc3n2)nn2cc(C)nc12]

50

7-(2,8-dimethylimidazo[1,2-b]pyridazin-6-yl)-2-[rac-(3R,4S)-3,4-difluoro-4-piperidyl]thiazolo[3,2-a]pyrimidin-5-one

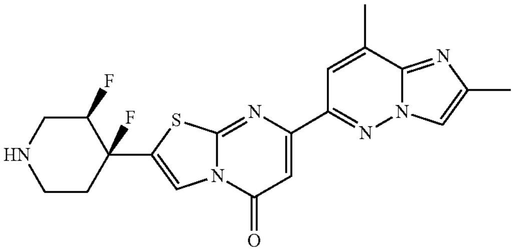 [SMILES: Cc1cn2nc(-c3cc(=O)n4cc([C@]5(F)CCNC[C@H]5F)sc4n3)cc(C)c2n1]

53

7-(2,8-dimethylimidazo[1,2-b]pyridazin-6-yl)-2-[rac-(3S,4S)-3,4-difluoro-4-piperidyl]thiazolo[3,2-a]pyrimidin-5-one

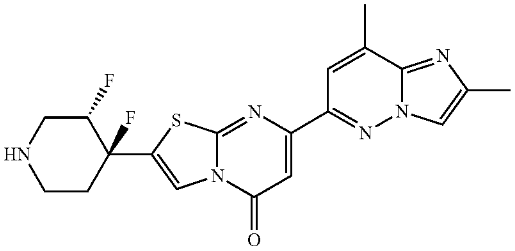 [SMILES: Cc1cn2nc(-c3cc(=O)n4cc([C@]5(F)CCNC[C@@H]5F)sc4n3)cc(C)c2n1]

54

7-(2,8-dimethylimidazo[1,2-b]pyridazin-6-yl)-2-[rac-(1S,5R)-3-azabicyclo[3.1.0]hexan-6-yl]thiazolo[3,2-a]pyrimidin-5-one

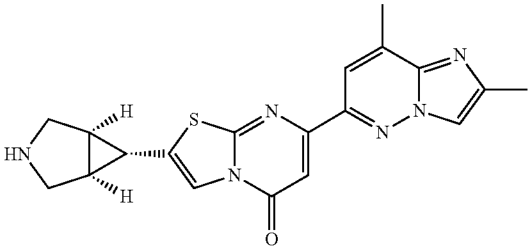 [SMILES: Cc1cn2nc(-c3cc(=O)n4cc([C@H]5[C@@H]6CNC[C@@H]65)sc4n3)cc(C)c2n1]

55

-continued

| | | |
|---|---|---|
| 7-(8-methoxy-2-methyl-imidazo[1,2-b]pyridazin-6-yl)-2-[(3R,4S)-3,4-difluoro-4-piperidyl]thiazolo[3,2-a]pyrimidin-5-one | 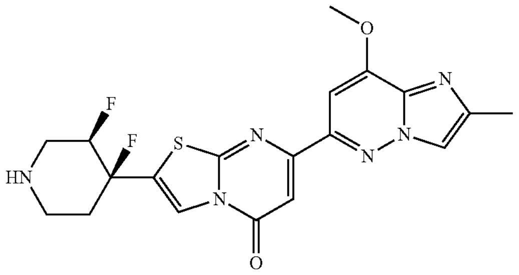 [SMILES: COc1cc(-c2cc(=O)n3cc([C@]4(F)CCNC[C@H]4F)sc3n2)nn2cc(C)nc12] | 56 |
| 7-(8-methoxy-2-methyl-imidazo[1,2-b]pyridazin-6-yl)-2-[(3S,4S)-3,4-difluoro-4-piperidyl]thiazolo[3,2-a]pyrimidin-5-one | 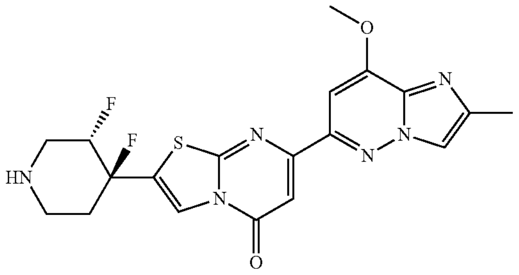 [SMILES: COc1cc(-c2cc(=O)n3cc([C@]4(F)CCNC[C@@H]4F)sc3n2)nn2cc(C)nc12] | 57 |
| 7-(8-methoxy-2-methyl-imidazo[1,2-b]pyridazin-6-yl)-2-[(3R,4R)-3,4-difluoro-4-piperidyl]thiazolo[3,2-a]pyrimidin-5-one | 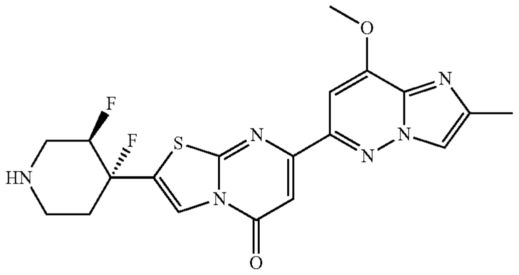 [SMILES: COc1cc(-c2cc(=O)n3cc([C@@]4(F)CCNC[C@H]4F)sc3n2)nn2cc(C)nc12] | 58 |
| 7-(8-methoxy-2-methyl-imidazo[1,2-b]pyridazin-6-yl)-2-[(3S,4R)-3,4-difluoro-4-piperidyl]thiazolo[3,2-a]pyrimidin-5-one | 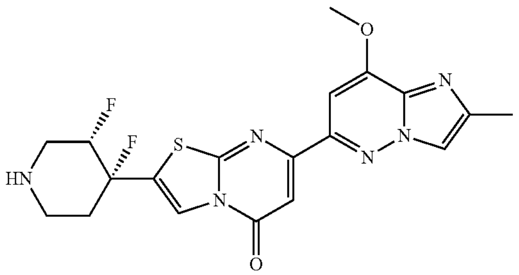 [SMILES: COc1cc(-c2cc(=O)n3cc([C@@]4(F)CCNC[C@@H]4F)sc3n2)nn2cc(C)nc12] | 59 |

or a pharmaceutically acceptable salt thereof.

16. A pharmaceutical composition comprising a compound of claim 1, or a pharmaceutically acceptable salt thereof, and a therapeutically inert carrier.

17. A method of reducing a protein level of huntingtin (HTT) in a brain of a subject, the method comprising administering to the subject in need thereof an effective amount of a compound of claim 1, or a pharmaceutically acceptable salt thereof.

18. A method of treating Huntington's disease, the method comprising administering to a subject in need thereof a therapeutically effective amount of a compound of claim 1, or a pharmaceutically acceptable salt thereof.

19. A compound of formula (Ib):

(Ib)

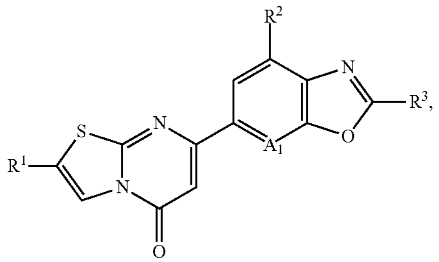

or a pharmaceutically acceptable salt thereof, wherein:

$A_1$ is selected from —N— and —CH—;

$R^1$ is selected from hydrogen, $C_{1-8}$ alkyl, $C_{3-10}$ cycloalkyl, $C_{6-10}$ aryl, 5-12 membered heteroaryl, and 3-12 membered heterocycloalkyl, wherein each of said $C_{3-10}$ cycloalkyl, $C_{6-10}$ aryl, 5-12 membered heteroaryl, and 3-12 membered heterocycloalkyl is optionally substituted with one, two, three, or four substituents independently selected from $R^4$;

$R^2$ is selected from hydrogen, halogen, cyano, amino, hydroxy, $C_{1-8}$ alkyl, $C_{2-8}$ alkenyl, $C_{1-8}$ alkoxy, $C_{1-8}$ haloalkyl, $C_{1-8}$ haloalkoxy, and $C_{3-10}$ cycloalkyl;

$R^3$ is selected from hydrogen, halogen, $C_{1-8}$ alkyl, and $C_{1-8}$ haloalkyl; and $R^4$ is selected from halogen, $C_{1-8}$ alkyl, 3-12 membered heterocycloalkyl, 3-12 membered heterocycloalkyl-$C_{1-8}$ alkyl, $C_{1-8}$ alkyl-3-12 membered heterocycloalkyl, 3-12 membered haloheterocycloalkyl, $C_{3-10}$ cycloalkyl, $C_{3-10}$ cycloalkyl-$C_{1-8}$ alkyl, $C_{1-8}$ alkyl-$C_{3-10}$ cycloalkyl, $C_{3-10}$ halocycloalkyl, $C_{3-10}$ cycloalkyl-amino, $C_{6-10}$ aryl, $C_{6-10}$ aryl-$C_{1-8}$ alkyl, $C_{1-8}$ alkyl-$C_{6-10}$ aryl, $C_{6-10}$ haloaryl, cyano, hydroxy, oxo, $C_{1-8}$ haloalkyl, $C_{1-8}$ alkyl-carbonyl, $C_{1-8}$ alkoxy, $C_{1-8}$ haloalkoxy, $C_{1-8}$ alkoxy-$C_{1-8}$ alkyl, $C_1$-8 alkoxy-carbonyl, amino, $C_{1-8}$ alkylamino, di ($C_{1-8}$ alkyl) amino, $C_{1-8}$ aminoalkyl, $C_{1-8}$ alkylamino-$C_{1-8}$ alkyl, di ($C_{1-8}$ alkyl) amino-$C_{1-8}$ alkyl, $C_{1-8}$ aminoalkyl-amino, $C_{1-8}$ alkoxy-$C_{1-8}$ alkylamino, $C_{1-8}$ alkyl-carbonyl-amino, $C_{1-8}$ alkoxy-carbonyl-amino, $C_{1-8}$ hydroxyalkyl, $C_{1-8}$ hydroxyalkoxy-$C_{1-8}$ alkyl, and $C_{1-8}$ hydroxyalkyl-amino.

20. A method of reducing a protein level of huntingtin (HTT) in a brain of a subject, the method comprising administering to the subject in need thereof an effective amount of a compound of claim 19, or a pharmaceutically acceptable salt thereof.

21. A method of treating Huntington's disease, the method comprising administering to a subject in need thereof a therapeutically affective amount of a compound of claim 19, or a pharmaceutically acceptable salt thereof.

22. A method of making a compound of Formula (I):

(I)

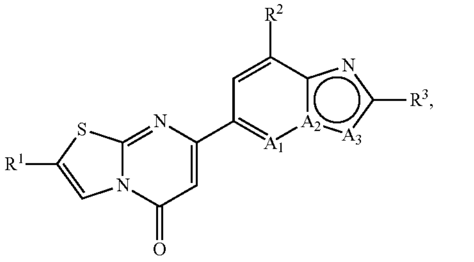

or a pharmaceutically acceptable salt thereof, wherein:

$R^1$ is selected from hydrogen, $C_{1-8}$ alkyl, $C_{3-10}$ cycloalkyl, $C_{6-10}$ aryl, 5-12 membered heteroaryl, and 3-12 membered heterocycloalkyl, wherein each of said $C_{3-10}$ cycloalkyl, $C_{6-10}$ aryl, 5-12 membered heteroaryl, and 3-12 membered heterocycloalkyl is optionally substituted with one, two, three, or four substituents independently selected from $R^4$;

$R^2$ is selected from hydrogen, halogen, cyano, amino, hydroxy, $C_{1-8}$ alkyl, $C_{2-8}$ alkenyl, $C_{1-8}$ alkoxy, $C_{1-8}$ haloalkyl, $C_{1-8}$ haloalkoxy, and $C_{3-10}$ cycloalkyl;

$R^3$ is selected from hydrogen, halogen, $C_{1-8}$ alkyl, and $C_{1-8}$ haloalkyl;

$R^4$ is selected from halogen, $C_{1-8}$ alkyl, 3-12 membered heterocycloalkyl, 3-12 membered heterocycloalkyl-$C_{1-8}$ alkyl, $C_{1-8}$ alkyl-3-12 membered heterocycloalkyl, 3-12 membered haloheterocycloalkyl, $C_{3-10}$ cycloalkyl, $C_{3-10}$ cycloalkyl-$C_{1-8}$ alkyl, $C_{1-8}$ alkyl-$C_{3-10}$ cycloalkyl, $C_{3-10}$ halocycloalkyl, $C_{3-10}$ cycloalkyl-amino, $C_{6-10}$ aryl, $C_{6-10}$ aryl-$C_{1-8}$ alkyl, $C_{1-8}$ alkyl-$C_{6-10}$ aryl, $C_{6-10}$ haloaryl, cyano, hydroxy, oxo, $C_{1-8}$ haloalkyl, $C_{1-8}$ alkyl-carbonyl, $C_{1-8}$ alkoxy, $C_{1-8}$ haloalkoxy, $C_{1-8}$ alkoxy-$C_{1-8}$ alkyl, $C_{1-8}$ alkoxy-carbonyl, amino, $C_{1-8}$ alkylamino, di ($C_{1-8}$ alkyl) amino, $C_{1-8}$ aminoalkyl, $C_{1-8}$ alkylamino-$C_{1-8}$ alkyl, di ($C_{1-8}$ alkyl) amino-$C_{1-8}$ alkyl, $C_{1-8}$ aminoalkyl-amino, $C_{1-8}$ alkoxy-$C_{1-8}$ alkylamino, $C_{1-8}$ alkyl-carbonyl-amino, $C_{1-8}$ alkoxy-carbonyl-amino, $C_{1-8}$ hydroxyalkyl, $C_{1-8}$ hydroxyalkoxy-$C_{1-8}$ alkyl, and $C_{1-8}$ hydroxyalkyl-amino; and (i) $A_1$ is —N—, $A_2$ is —N— and $A_3$ is —CH—;

(ii) $A_1$ is —N—, $A_2$ is —C— and $A_3$ is —O—; or (iii) $A_1$ is —CH—, $A_2$ is —C— and $A_3$ is —O—;

the method comprising at least one step selected from:

(a) reacting a compound of formula (B1)

(B1)

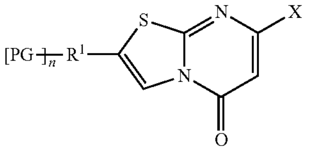

with a compound of formula (B2)

(B2)

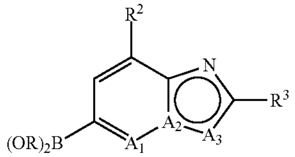

in a suitable solvent in the presence of a base and a suitable palladium catalyst, wherein:

n is 0 or 1,

X is selected from O-tosylate, O-triflate, O-mesylate, and halogen, each R in —$B(OR)_2$ of the compound formula (B2) is independently selected from hydrogen and $C_{1-8}$ alkyl, or —$B(OR)_2$ is optionally substituted dioxaborolanyl, PG is a protecting group; and $R^1$ in formula (B1) and $R^2$, $R^3$, $A_1$, $A_2$, and $A_3$ in formula (B2) are as defined for formula (I) and when n is 1, $R^1$ is not hydrogen;

to arrive at a compound of formula (B3):
(B3)
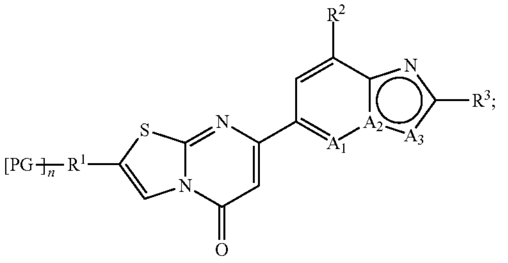
and
(b) reacting a compound of formula (B3), wherein n is 1, in a suitable solvent and in presence of an acid, to yield the compound of formula (I).
* * * * *